US011592368B2

(12) United States Patent
Biadillah et al.

(10) Patent No.: US 11,592,368 B2
(45) Date of Patent: Feb. 28, 2023

(54) METHOD FOR COLLECTING AND PRESERVING A BIOLOGICAL SAMPLE

(71) Applicant: DNA GENOTEK, INC., Ottawa (CA)

(72) Inventors: Youssef Biadillah, Geneva (CH); Stephen D. Andrews, Falmouth, ME (US)

(73) Assignee: DNA Genotek, INC., Ottawa (CA)

(*) Notice: Subject to any disclaimer, the term of this patent is extended or adjusted under 35 U.S.C. 154(b) by 0 days.

(21) Appl. No.: 17/509,961

(22) Filed: Oct. 25, 2021

(65) Prior Publication Data

US 2022/0042883 A1    Feb. 10, 2022

Related U.S. Application Data

(63) Continuation of application No. 16/023,772, filed on Jun. 29, 2018, which is a continuation of application
(Continued)

(51) Int. Cl.
*G01N 1/30* (2006.01)
*A61B 10/00* (2006.01)
(Continued)

(52) U.S. Cl.
CPC ............ *G01N 1/30* (2013.01); *A61B 10/007* (2013.01); *A61B 10/0051* (2013.01);
(Continued)

(58) Field of Classification Search
CPC ...... G01N 1/30; G01N 1/10; G01N 2001/002; G01N 2001/305; A61B 10/0051;
(Continued)

(56) References Cited

U.S. PATENT DOCUMENTS

| 718,127 A | 1/1903 | Holmgren |
| 2,275,567 A | 3/1942 | Smith |

(Continued)

FOREIGN PATENT DOCUMENTS

| AU | 2006324337 B2 | 6/2007 |
| CA | 2 072 331 A1 | 12/1992 |

(Continued)

OTHER PUBLICATIONS

Exhibit 1 of Declaration of Brian M. Kramer in Support of DNA Genotek Inc.'s Opposition to Defendants' "Unopposed" Motion for Leave to File Surreply and DNA Genotek Inc.'s Motion to Strike Unauthorized Expert Declaration, filed Nov. 20, 2015: a true and correct copy of an email chain between attorneys for Spectrum and attorneys for DNA Genotek, with dates ranging from Nov. 17, 2015, to Nov. 18, 2015, bearing the subject line "Re: *DNA Genotek v.Spectrum*; Case No. 15-CV-00661-SLR." (4 pages).

(Continued)

*Primary Examiner* — Samuel P Siefke
(74) *Attorney, Agent, or Firm* — Cooley LLP

(57) ABSTRACT

The disclosure relates to devices, solutions and methods for collecting and processing samples of bodily fluids containing cells (as well as embodiments for the collection, and processing and/or analysis of other fluids including toxic and/or hazardous substances/fluids). In addition, the disclosure relates generally to function genomic studies and to the isolation and preservation of cells from saliva and other bodily fluids (e.g., urine), for cellular analysis. With respect to devices for collection of bodily fluids, some embodiments include two mating bodies, a cap and a tube (for example), where, in some embodiments, the cap includes a closed interior space for holding a sample preservative solution and mates with the tube to constitute the (closed) sample collection device. Upon mating, the preservation solution flows (Continued)

into the closed interior space to preserve cells in the bodily fluid. The tube is configured to receive a donor sample of bodily fluid (e.g., saliva, urine), which can then be subjected to processing to extract a plurality of cells. The plurality of cells can be further processed to isolate one and/or another cell type therefrom. The plurality of cells, as well as the isolated cell type(s), can be analyzed for functional genomic and epigenetic studies, as well as biomarker discovery.

19 Claims, 9 Drawing Sheets

Related U.S. Application Data

No. 15/227,693, filed on Aug. 3, 2016, now abandoned, which is a continuation of application No. 14/127,832, filed as application No. PCT/US2012/043176 on Jun. 19, 2012, now Pat. No. 9,442,046.

(60) Provisional application No. 61/598,618, filed on Feb. 14, 2012, provisional application No. 61/598,601, filed on Feb. 14, 2012, provisional application No. 61/498,584, filed on Jun. 19, 2011.

(51) Int. Cl.
    *B01L 3/00*     (2006.01)
    *G01N 1/10*     (2006.01)
    *G01N 1/00*     (2006.01)

(52) U.S. Cl.
    CPC .......... *A61B 10/0096* (2013.01); *B01L 3/502* (2013.01); *G01N 1/10* (2013.01); *B01L 3/5021* (2013.01); *B01L 3/50825* (2013.01); *B01L 2200/025* (2013.01); *B01L 2200/0689* (2013.01); *B01L 2200/085* (2013.01); *B01L 2300/042* (2013.01); *B01L 2300/047* (2013.01); *B01L 2300/049* (2013.01); *B01L 2300/0832* (2013.01); *B01L 2400/0683* (2013.01); *G01N 2001/002* (2013.01); *G01N 2001/305* (2013.01)

(58) Field of Classification Search
    CPC ... A61B 10/007; A61B 10/0096; B01L 3/502; B01L 3/5021; B01L 3/50825; B01L 2200/025; B01L 2200/0689; B01L 2200/085; B01L 2300/042; B01L 2300/047; B01L 2300/049; B01L 2300/0832; B01L 2400/0683
    See application file for complete search history.

(56) References Cited

U.S. PATENT DOCUMENTS

| | | |
|---|---|---|
| 2,631,521 A | 3/1953 | Atkins |
| D169,994 S | 7/1953 | Soffer et al. |
| 2,653,611 A | 9/1953 | Smith |
| D175,257 S | 8/1955 | Hopkins |
| 2,764,157 A | 9/1956 | Oliva et al. |
| 2,764,983 A | 10/1956 | Barasch |
| 2,773,591 A | 12/1956 | Jensen |
| 2,793,776 A | 5/1957 | Ipari |
| 2,958,439 A | 11/1960 | Yochem |
| D196,112 S | 8/1963 | Esser |
| 3,199,704 A | 8/1965 | Davidson |
| 3,321,097 A | 5/1967 | Solowey |
| 3,340,873 A | 9/1967 | Solowey |
| 3,347,410 A | 12/1967 | Schwartzman |
| 3,419,179 A | 12/1968 | Deuschle et al. |
| D213,292 S | 2/1969 | Arsenault |
| 3,441,179 A | 4/1969 | Ragan |
| 3,464,414 A | 9/1969 | Sponnoble |
| 3,518,164 A | 6/1970 | Andelin et al. |
| 3,536,191 A | 10/1970 | Williams |
| 3,537,606 A | 11/1970 | Solowey |
| D221,751 S | 9/1971 | Kronish et al. |
| 3,603,484 A | 9/1971 | Ogle |
| 3,651,990 A | 3/1972 | Cernei |
| 3,674,028 A | 7/1972 | Ogle |
| 3,694,455 A | 9/1972 | Dunn |
| 3,731,853 A | 5/1973 | Baumann |
| 3,799,426 A | 3/1974 | Pates et al. |
| 3,815,580 A | 6/1974 | Oster |
| 3,831,742 A | 8/1974 | Gardella et al. |
| D233,138 S | 10/1974 | Vogel |
| 3,846,077 A | 11/1974 | Ohringer |
| 3,968,872 A | 7/1976 | Cavazza |
| D241,416 S | 9/1976 | Aul |
| D244,555 S | 5/1977 | Wiedmann |
| D246,600 S | 12/1977 | Kurata |
| D246,698 S | 12/1977 | Morris |
| 4,081,356 A | 3/1978 | Zierdt |
| 4,089,432 A | 5/1978 | Crankshaw |
| 4,102,451 A | 7/1978 | Clarke et al. |
| 4,131,016 A | 12/1978 | Layton |
| 4,140,489 A | 2/1979 | Lee et al. |
| 4,150,950 A | 4/1979 | Takeguchi et al. |
| D252,612 S | 8/1979 | Mull |
| 4,170,798 A | 10/1979 | Krumdieck |
| 4,175,008 A | 11/1979 | White |
| 4,184,483 A | 1/1980 | Greenspan |
| 4,195,730 A | 4/1980 | Hunt |
| 4,200,100 A | 4/1980 | Willis |
| D255,092 S | 5/1980 | Wong |
| D256,053 S | 7/1980 | Steigerwald |
| 4,217,798 A | 8/1980 | McCarthy et al. |
| 4,221,291 A | 9/1980 | Hunt |
| 4,258,032 A | 3/1981 | Mehl |
| 4,301,812 A | 11/1981 | Layton et al. |
| 4,312,950 A | 1/1982 | Snyder et al. |
| 4,324,859 A | 4/1982 | Saxholm |
| 4,340,147 A | 7/1982 | McIntosh |
| 4,386,696 A | 6/1983 | Goncalves |
| 4,418,702 A | 12/1983 | Brown et al. |
| D274,132 S | 6/1984 | Nightingale, III |
| 4,465,183 A | 8/1984 | Saito et al. |
| D277,736 S | 2/1985 | Long |
| 4,505,433 A | 3/1985 | Selenke |
| 4,583,971 A | 4/1986 | Bocquet et al. |
| 4,589,548 A | 5/1986 | Fay |
| 4,591,050 A | 5/1986 | Finke et al. |
| D285,115 S | 8/1986 | Proud et al. |
| 4,615,437 A | 10/1986 | Finke et al. |
| D286,546 S | 11/1986 | Funashashi |
| D287,570 S | 1/1987 | Olsen |
| 4,634,003 A | 1/1987 | Ueda et al. |
| 4,663,161 A | 5/1987 | Mannino et al. |
| 4,678,559 A | 7/1987 | Szabados |
| 4,726,950 A | 2/1988 | Desai et al. |
| 4,727,985 A | 3/1988 | McNeirney et al. |
| 4,741,346 A | 5/1988 | Wong et al. |
| D296,241 S | 6/1988 | Miskinis |
| 4,753,358 A | 6/1988 | Virca et al. |
| 4,761,379 A | 8/1988 | Williams et al. |
| 4,785,931 A | 11/1988 | Weir et al. |
| 4,832,917 A | 5/1989 | Elliott |
| D303,710 S | 9/1989 | Neill |
| 4,914,023 A | 4/1990 | Philo |
| 4,918,178 A | 4/1990 | Hurley et al. |
| 4,927,605 A | 5/1990 | Dorn et al. |
| 4,932,081 A | 6/1990 | Burns |
| 4,935,342 A | 6/1990 | Seligson et al. |
| D310,264 S | 8/1990 | Leoncavallo et al. |
| 4,950,237 A | 8/1990 | Henault et al. |
| 4,961,516 A | 10/1990 | Nakamura |
| 4,982,553 A | 1/1991 | Itoh |
| 4,982,875 A | 1/1991 | Pozzi |
| 4,999,288 A | 3/1991 | deCastro et al. |
| D318,727 S | 7/1991 | Spike |
| 5,029,718 A | 7/1991 | Rizzardi |

(56) References Cited

U.S. PATENT DOCUMENTS

| | | |
|---|---|---|
| 5,066,463 A | 11/1991 | Chang |
| 5,091,316 A | 2/1992 | Monthony et al. |
| D325,444 S | 4/1992 | Murashita et al. |
| 5,128,104 A | 7/1992 | Murphy et al. |
| 5,140,043 A | 8/1992 | Darr et al. |
| D330,011 S | 10/1992 | Miller et al. |
| 5,152,965 A | 10/1992 | Fisk et al. |
| 5,196,182 A | 3/1993 | Ryan |
| D338,956 S | 8/1993 | Hadaway et al. |
| 5,234,809 A | 8/1993 | Boom et al. |
| 5,268,148 A | 12/1993 | Seymour |
| 5,283,038 A | 2/1994 | Seymour |
| D344,804 S | 3/1994 | Muniz |
| 5,291,991 A | 3/1994 | Meyer |
| 5,330,048 A | 7/1994 | Haber et al. |
| 5,335,673 A | 8/1994 | Goldstein et al. |
| 5,353,961 A | 10/1994 | Debush |
| 5,364,591 A | 11/1994 | Green et al. |
| 5,364,763 A | 11/1994 | Kacian |
| 5,376,527 A | 12/1994 | Robson et al. |
| 5,380,492 A | 1/1995 | Seymour |
| 5,384,096 A | 1/1995 | Burns |
| D355,606 S | 2/1995 | Manera |
| 5,393,496 A | 2/1995 | Seymour |
| 5,396,986 A | 3/1995 | Fountain et al. |
| D357,985 S | 5/1995 | Burns |
| 5,422,273 A | 6/1995 | Garrison et al. |
| 5,425,921 A | 6/1995 | Coakley et al. |
| D362,184 S | 9/1995 | Carr |
| D362,623 S | 9/1995 | Ma |
| 5,477,863 A | 12/1995 | Grant |
| 5,478,722 A | 12/1995 | Caldwell |
| D367,114 S | 2/1996 | Wilson et al. |
| 5,490,971 A | 2/1996 | Gifford et al. |
| 5,494,646 A | 2/1996 | Seymour |
| 5,496,562 A | 3/1996 | Burgoyne |
| 5,512,440 A | 4/1996 | Down et al. |
| D372,093 S | 7/1996 | Sampson et al. |
| 5,540,326 A | 7/1996 | Arnold et al. |
| 5,556,544 A | 9/1996 | Didier |
| D375,160 S | 10/1996 | Sampson et al. |
| 5,567,309 A | 10/1996 | Classon et al. |
| 5,624,554 A | 4/1997 | Faulkner et al. |
| D379,663 S | 6/1997 | Pearson et al. |
| 5,643,767 A | 7/1997 | Fischetti et al. |
| 5,658,531 A | 8/1997 | Cope et al. |
| D383,214 S | 9/1997 | Brennan |
| D383,851 S | 9/1997 | Wong |
| D385,793 S | 11/1997 | Marsal |
| D388,519 S | 12/1997 | Skiffington et al. |
| 5,692,644 A | 12/1997 | Gueret |
| 5,707,860 A | 1/1998 | Collis et al. |
| 5,714,341 A | 2/1998 | Thieme et al. |
| D392,187 S | 3/1998 | King |
| 5,736,322 A | 4/1998 | Goldstein |
| 5,736,355 A | 4/1998 | Dyke et al. |
| 5,756,126 A | 5/1998 | Burgoyne |
| 5,786,208 A | 7/1998 | Clark et al. |
| 5,786,228 A | 7/1998 | Charlton |
| 5,788,652 A | 8/1998 | Rahn |
| 5,807,527 A | 9/1998 | Burgoyne |
| 5,814,442 A | 9/1998 | Natarajan et al. |
| 5,817,630 A | 10/1998 | Hofmann et al. |
| 5,827,675 A | 10/1998 | Skiffington et al. |
| D401,697 S | 11/1998 | Cloonan et al. |
| 5,829,696 A | 11/1998 | DeStefano et al. |
| 5,830,154 A | 11/1998 | Goldstein et al. |
| 5,830,410 A | 11/1998 | Thieme et al. |
| 5,837,452 A | 11/1998 | Clark et al. |
| D402,766 S | 12/1998 | Smith et al. |
| 5,843,654 A | 12/1998 | Heisler et al. |
| 5,849,890 A | 12/1998 | Gold et al. |
| 5,869,328 A | 2/1999 | Antoci et al. |
| 5,871,905 A | 2/1999 | Thieme et al. |
| 5,909,753 A | 6/1999 | Rossi et al. |
| 5,910,407 A | 6/1999 | Vogelstein et al. |
| D412,107 S | 7/1999 | Bosshardt |
| 5,921,396 A | 7/1999 | Brown |
| 5,927,549 A | 7/1999 | Wood |
| 5,933,498 A | 8/1999 | Schneck et al. |
| 5,935,804 A | 8/1999 | Laine et al. |
| 5,935,864 A | 8/1999 | Schramm et al. |
| 5,939,262 A | 8/1999 | Pasloske et al. |
| 5,941,380 A | 8/1999 | Rothman |
| 5,950,819 A | 9/1999 | Sellars |
| 5,967,309 A | 10/1999 | Robles-Gonzalez et al. |
| 5,968,746 A | 10/1999 | Schneider |
| 5,976,829 A | 11/1999 | Birnboim |
| 5,980,834 A | 11/1999 | Bruno |
| 5,984,141 A | 11/1999 | Gibler |
| 5,992,693 A | 11/1999 | Albisetti |
| 5,973,137 A | 12/1999 | Heath |
| 6,003,728 A | 12/1999 | Elliott |
| 6,020,186 A | 2/2000 | Henco et al. |
| 6,020,196 A | 2/2000 | Hu et al. |
| 6,048,091 A | 4/2000 | McIntyre et al. |
| D424,440 S | 5/2000 | Wilkinson et al. |
| D425,618 S | 5/2000 | Niermann et al. |
| D425,625 S | 5/2000 | Niermann |
| D426,313 S | 6/2000 | Woolston et al. |
| 6,071,745 A | 6/2000 | Lin et al. |
| 6,076,570 A | 6/2000 | Byrne |
| 6,084,091 A | 7/2000 | Muller et al. |
| 6,090,793 A | 7/2000 | Zimmermann et al. |
| 6,113,257 A | 9/2000 | Sharon et al. |
| 6,121,055 A | 9/2000 | Hargreaves |
| D432,245 S | 10/2000 | Stevens et al. |
| 6,135,275 A | 10/2000 | Kelders et al. |
| 6,138,821 A | 10/2000 | Hsu |
| 6,148,996 A | 11/2000 | Morini |
| 6,149,866 A | 11/2000 | Luotola et al. |
| 6,152,296 A | 11/2000 | Shih |
| 6,168,922 B1 | 1/2001 | Harvey et al. |
| 6,170,719 B1 | 1/2001 | Wilkinson et al. |
| 6,176,836 B1 | 1/2001 | Trudil et al. |
| D437,786 S | 2/2001 | van Swieten et al. |
| 6,182,845 B1 | 2/2001 | Wolfe et al. |
| 6,187,546 B1 | 2/2001 | O'Neill et al. |
| 6,190,875 B1 | 2/2001 | Ben-Artzi et al. |
| 6,204,375 B1 | 3/2001 | Lader |
| D442,090 S | 5/2001 | Jackson et al. |
| 6,224,922 B1 | 5/2001 | Fonte |
| 6,228,323 B1 | 5/2001 | Asgharian et al. |
| 6,235,010 B1 | 5/2001 | Wilkinson et al. |
| 6,235,466 B1 | 5/2001 | Branch et al. |
| 6,242,188 B1 | 6/2001 | Dattagupta et al. |
| 6,247,586 B1 | 6/2001 | Herzog et al. |
| D445,908 S | 7/2001 | Conway |
| 6,270,970 B1 | 8/2001 | Smith et al. |
| 6,277,646 B1 | 8/2001 | Guirguis et al. |
| D447,812 S | 9/2001 | Conway |
| 6,291,178 B1 | 9/2001 | Schneider |
| 6,309,827 B1 | 10/2001 | Goldstein et al. |
| 6,310,195 B1 | 10/2001 | Colucci et al. |
| 6,313,286 B1 | 11/2001 | Brown et al. |
| 6,350,578 B1 | 2/2002 | Stark et al. |
| D455,908 S | 4/2002 | Liu |
| 6,379,315 B1 | 4/2002 | Claren et al. |
| D457,247 S | 5/2002 | Iheme et al. |
| 6,383,393 B1 | 5/2002 | Colpan et al. |
| 6,471,069 B2 | 5/2002 | Colpan et al. |
| 6,409,528 B1 | 6/2002 | Bodnar |
| 6,428,962 B1 | 8/2002 | Naegele |
| 6,448,002 B1 | 9/2002 | Hillebrand et al. |
| 6,458,546 B1 | 10/2002 | Baker |
| D465,731 S | 11/2002 | Brant et al. |
| D467,665 S | 12/2002 | Niedbala et al. |
| 6,489,172 B1 | 12/2002 | Bachand et al. |
| 6,503,716 B1 | 1/2003 | Lai et al. |
| D470,240 S | 2/2003 | Niedbala et al. |
| 6,524,530 B1 | 2/2003 | Igarashi et al. |
| D471,234 S | 3/2003 | Okutani |
| D471,639 S | 3/2003 | McMichael et al. |
| 6,527,110 B2 | 3/2003 | Moscovitz |

(56) References Cited

U.S. PATENT DOCUMENTS

| | | |
|---|---|---|
| 6,528,641 B2 | 3/2003 | Lader |
| 6,533,113 B2 | 3/2003 | Moscovitz |
| 6,539,817 B2 | 4/2003 | Kozak et al. |
| 6,543,612 B2 | 4/2003 | Lee et al. |
| 6,548,256 B2 | 4/2003 | Lienau et al. |
| 6,551,777 B1 | 4/2003 | Shuber et al. |
| D474,280 S | 5/2003 | Niedbala et al. |
| 6,562,300 B2 | 5/2003 | Rosen et al. |
| 6,582,415 B1 | 6/2003 | Fowles et al. |
| 6,602,718 B1 | 8/2003 | Augello et al. |
| 6,617,170 B2 | 9/2003 | Augello et al. |
| 6,627,152 B1 | 9/2003 | Wong |
| 6,630,585 B2 | 10/2003 | Kojima |
| 6,632,662 B1 | 10/2003 | Broyer et al. |
| 6,634,234 B1 | 10/2003 | Haas |
| 6,634,243 B1 | 10/2003 | Wickstead et al. |
| 6,664,379 B1 | 12/2003 | Kudlicki et al. |
| 6,667,053 B1 | 12/2003 | Ahmad et al. |
| 6,716,392 B1 | 4/2004 | Putcha et al. |
| 6,777,210 B1 | 8/2004 | Pasloske et al. |
| 6,786,330 B2 | 9/2004 | Mollstam et al. |
| 6,815,541 B1 | 11/2004 | Mitsugu et al. |
| 6,825,340 B2 | 11/2004 | Pasloske et al. |
| 6,832,994 B2 | 12/2004 | Niedospial, Jr. et al. |
| 6,849,403 B1 | 2/2005 | Shuber |
| 6,852,495 B2 | 2/2005 | Kojima |
| 6,858,224 B2 | 2/2005 | Wheeler et al. |
| 6,869,769 B2 | 3/2005 | Burgoyne |
| 6,880,771 B2 | 4/2005 | Deppermann |
| 6,893,612 B2 | 5/2005 | Kacian |
| D507,351 S | 7/2005 | Birnboim |
| 6,913,932 B2 | 7/2005 | Maples et al. |
| 6,939,672 B2 | 9/2005 | Lentrichia et al. |
| D513,181 S | 12/2005 | Bloom et al. |
| 6,979,449 B1 | 12/2005 | Mock |
| 6,989,249 B2 | 1/2006 | Libragen |
| 6,992,182 B1 | 1/2006 | Muller et al. |
| D515,435 S | 2/2006 | Muehlhausen |
| 7,001,724 B1 | 2/2006 | Greenfield |
| 7,005,109 B2 | 2/2006 | Husar |
| 7,005,266 B2 | 2/2006 | Sprenger-Haussels |
| D519,030 S | 4/2006 | Matsuda et al. |
| 7,029,840 B2 | 4/2006 | McMillian |
| 7,041,484 B1 | 5/2006 | Baga et al. |
| 7,055,685 B1 | 6/2006 | Patterson et al. |
| D529,817 S | 10/2006 | Francavilla et al. |
| D537,416 S | 2/2007 | Fortin et al. |
| 7,178,683 B2 | 2/2007 | Birkmayer et al. |
| 7,214,484 B2 | 5/2007 | Weber et al. |
| 7,244,828 B2 | 7/2007 | Alam |
| 7,267,980 B1 | 9/2007 | Mortari et al. |
| 7,270,953 B2 | 9/2007 | Hollander et al. |
| D555,802 S | 11/2007 | Coulling et al. |
| 7,297,485 B2 | 11/2007 | Bornar et al. |
| 7,300,632 B2 | 11/2007 | Sugiyama et al. |
| 7,303,876 B2 | 12/2007 | Greenfield et al. |
| D562,462 S | 2/2008 | Muir et al. |
| 7,338,634 B2 | 3/2008 | Chang |
| D566,555 S | 4/2008 | Berman |
| D573,465 S | 7/2008 | Kogure et al. |
| D574,507 S | 8/2008 | Muir et al. |
| D580,070 S | 11/2008 | Riley |
| 7,464,811 B2 | 12/2008 | Patterson et al. |
| D584,357 S | 1/2009 | Oka |
| 7,482,116 B2 | 1/2009 | Birnboim |
| D586,856 S | 2/2009 | Yagyu |
| 7,507,374 B2 | 3/2009 | Gould et al. |
| 7,521,213 B2 | 4/2009 | Hantash |
| D592,954 S | 5/2009 | Capretta et al. |
| 7,537,132 B2 | 5/2009 | Marple et al. |
| 7,544,468 B2 | 6/2009 | Goldstein et al. |
| D599,032 S | 8/2009 | Bucholtz et al. |
| 7,589,184 B2 | 9/2009 | Hogan et al. |
| D604,612 S | 11/2009 | Germann |
| 7,638,307 B2 | 12/2009 | Hantash |
| 7,645,424 B2 | 1/2010 | O'Donovan |
| 7,666,609 B1 | 2/2010 | Guo et al. |
| D612,730 S | 3/2010 | Rushe |
| 7,748,550 B2 | 7/2010 | Cho |
| 7,749,757 B1 | 7/2010 | Mortari et al. |
| D626,249 S | 10/2010 | Wang et al. |
| D627,081 S | 11/2010 | Giraud et al. |
| 7,850,043 B2 | 12/2010 | Foster |
| 7,854,104 B2 | 12/2010 | Cronin et al. |
| 7,854,895 B2 | 12/2010 | Gallager et al. |
| 7,858,396 B2 | 12/2010 | Corstjens et al. |
| D631,169 S | 1/2011 | Cheeley et al. |
| D631,350 S | 1/2011 | Beach et al. |
| D631,553 S | 1/2011 | Niedbala et al. |
| D631,554 S | 1/2011 | Jackson et al. |
| 7,927,611 B2 | 4/2011 | Campos-Neto et al. |
| 7,935,483 B2 | 5/2011 | Kamata et al. |
| D640,794 S | 6/2011 | Sunstrum et al. |
| D640,795 S | 6/2011 | Jackson et al. |
| D640,797 S | 6/2011 | Wilkinson |
| 7,998,757 B2 | 8/2011 | Darrigrand et al. |
| 8,034,272 B2 | 10/2011 | Pavlovic |
| 8,038,668 B2 | 10/2011 | Scott et al. |
| 8,062,908 B2 | 11/2011 | Mink et al. |
| 8,084,443 B2 | 12/2011 | Fischer et al. |
| D656,236 S | 3/2012 | Marechal et al. |
| 8,158,357 B2 | 4/2012 | Birnboim et al. |
| D659,254 S | 5/2012 | Miyashita et al. |
| D660,960 S | 5/2012 | Gronberg |
| 8,221,381 B2 | 7/2012 | Muir et al. |
| D667,960 S | 9/2012 | Wilkinson |
| D673,265 S | 12/2012 | Nonnemacher et al. |
| 8,405,379 B1 | 3/2013 | Montagnier |
| 8,470,536 B2 | 6/2013 | Birnboim et al. |
| 8,486,909 B2 | 7/2013 | Rennard et al. |
| 8,551,016 B2 | 10/2013 | Slowey et al. |
| D693,682 S | 11/2013 | Bahri et al. |
| 8,673,239 B2 | 3/2014 | Niedbala et al. |
| 8,728,414 B2 | 5/2014 | Beach et al. |
| 8,738,297 B2 | 5/2014 | Sorenson et al. |
| 8,796,028 B2 | 8/2014 | Hollander |
| 8,855,935 B2 | 10/2014 | Myres et al. |
| 8,881,988 B2 | 11/2014 | Miceli |
| 9,040,675 B2 | 5/2015 | Bales et al. |
| 9,072,499 B2 | 7/2015 | Birnboim et al. |
| 9,079,181 B2 | 7/2015 | Curry et al. |
| D743,044 S | 11/2015 | Jackson et al. |
| D743,571 S | 11/2015 | Jackson et al. |
| 9,207,164 B2 | 12/2015 | Muir et al. |
| 9,442,046 B2 | 9/2016 | Biadillah et al. |
| 9,523,115 B2 | 12/2016 | Birnboim |
| 9,757,179 B2 | 9/2017 | Formica |
| 10,000,795 B2 | 6/2018 | Birnboim et al. |
| D850,647 S | 6/2019 | Jackson et al. |
| 10,435,735 B2 | 10/2019 | Birnboim et al. |
| 10,576,468 B2 | 3/2020 | Biadillah et al. |
| 10,619,187 B2 | 4/2020 | Birnboim |
| D890,359 S | 7/2020 | Jackson et al. |
| 10,767,215 B2 | 9/2020 | Birnboim |
| 11,002,646 B2 | 5/2021 | Biadillah et al. |
| 11,046,949 B2 | 6/2021 | Birnboim et al. |
| 2001/0008614 A1 | 7/2001 | Aronowitz |
| 2001/0023072 A1 | 9/2001 | Crawford et al. |
| 2001/0039058 A1 | 11/2001 | Iheme et al. |
| 2002/0004206 A1 | 1/2002 | Berger et al. |
| 2002/0026046 A1 | 2/2002 | Pasloske et al. |
| 2002/0037512 A1 | 3/2002 | Baker |
| 2002/0064802 A1 | 5/2002 | Raschke et al. |
| 2002/0081575 A1 | 6/2002 | Small et al. |
| 2002/0092852 A1 | 7/2002 | Stewart et al. |
| 2002/0102580 A1 | 8/2002 | Baker |
| 2002/0146677 A1 | 10/2002 | Augello et al. |
| 2002/0185389 A1 | 12/2002 | Kelders et al. |
| 2002/0197275 A1 | 12/2002 | Sunvold et al. |
| 2002/0197631 A1 | 12/2002 | Lawrence et al. |
| 2003/0008379 A1 | 1/2003 | Bhosle et al. |
| 2003/0013112 A1 | 1/2003 | Sprenger Haussels |
| 2003/0049675 A1 | 3/2003 | Libragen |
| 2003/0064526 A1 | 4/2003 | Niedbala et al. |

(56) References Cited

U.S. PATENT DOCUMENTS

| | | |
|---|---|---|
| 2003/0073830 A1 | 4/2003 | Heath et al. |
| 2003/0089627 A1 | 5/2003 | Chelles et al. |
| 2003/0091989 A1 | 5/2003 | Davis et al. |
| 2003/0104424 A1 | 6/2003 | Tuggle et al. |
| 2003/0109548 A1 | 6/2003 | Royt et al. |
| 2003/0113705 A1 | 6/2003 | McMillian et al. |
| 2003/0114430 A1 | 6/2003 | MacLeod et al. |
| 2003/0119077 A1 | 6/2003 | Ts'o et al. |
| 2003/0132244 A1 | 7/2003 | Birkmayer et al. |
| 2003/0170694 A1 | 9/2003 | Wall et al. |
| 2003/0172065 A1 | 9/2003 | Sorenson et al. |
| 2003/0181826 A1 | 9/2003 | Smith et al. |
| 2003/0215954 A1 | 11/2003 | Cockerill, III et al. |
| 2003/0229222 A1 | 12/2003 | Kojima |
| 2004/0014104 A1 | 1/2004 | Shuber |
| 2004/0018120 A1 | 1/2004 | Rappin et al. |
| 2004/0018575 A1 | 1/2004 | Rappin et al. |
| 2004/0019196 A1 | 1/2004 | Bair, Jr. et al. |
| 2004/0038269 A1 | 2/2004 | Birnboim |
| 2004/0038424 A1 | 2/2004 | Maples |
| 2004/0043453 A1 | 3/2004 | Drocourt |
| 2004/0049805 A1 | 3/2004 | Lerchl et al. |
| 2004/0050700 A1 | 3/2004 | Lopez-Canovas et al. |
| 2004/0062785 A1 | 4/2004 | Parker |
| 2004/0105917 A1 | 6/2004 | Mannion et al. |
| 2004/0111763 A1 | 6/2004 | Heinz et al. |
| 2004/0132091 A1 | 7/2004 | Ramsey et al. |
| 2004/0137422 A1 | 7/2004 | Golabek et al. |
| 2004/0157219 A1 | 8/2004 | Lou et al. |
| 2004/0157223 A1 | 8/2004 | Lou et al. |
| 2004/0161788 A1 | 8/2004 | Chen et al. |
| 2004/0197845 A1 | 10/2004 | Hassibi et al. |
| 2004/0200740 A1 | 10/2004 | Cho |
| 2004/0200741 A1 | 10/2004 | Cho |
| 2004/0200742 A1 | 10/2004 | Cho |
| 2004/0209332 A1 | 10/2004 | Marciacq |
| 2004/0226835 A1 | 11/2004 | Takahashi et al. |
| 2004/0229264 A1 | 11/2004 | Crossman et al. |
| 2004/0245125 A1 | 12/2004 | Trkulja |
| 2005/0019814 A1 | 1/2005 | Laugharn et al. |
| 2005/0040052 A1 | 2/2005 | Dixon |
| 2005/0059163 A1 | 3/2005 | Dastane et al. |
| 2005/0070109 A1 | 3/2005 | Feller et al. |
| 2005/0091706 A1 | 4/2005 | Klimyuk |
| 2005/0112024 A1 | 5/2005 | Gou et al. |
| 2005/0142031 A1 | 6/2005 | Wickstead et al. |
| 2005/0181363 A1 | 8/2005 | Kamata et al. |
| 2005/0191685 A1 | 9/2005 | Vanmechelen et al. |
| 2005/0227292 A1 | 10/2005 | Sunderasan |
| 2005/0227303 A1 | 10/2005 | Guo et al. |
| 2005/0239045 A1 | 10/2005 | Okamoto et al. |
| 2005/0277121 A1 | 12/2005 | Pasloske et al. |
| 2005/0282202 A1 | 12/2005 | Brolaski et al. |
| 2006/0018799 A1 | 1/2006 | Wong et al. |
| 2006/0029972 A1 | 2/2006 | Lorenz |
| 2006/0122534 A1 | 6/2006 | Matsumura et al. |
| 2006/0139631 A1 | 6/2006 | Feldsine et al. |
| 2006/0154307 A1 | 7/2006 | Milligan |
| 2006/0201948 A1 | 9/2006 | Ellson et al. |
| 2006/0206946 A1 | 9/2006 | Hamza |
| 2006/0210448 A1 | 9/2006 | Wang et al. |
| 2006/0210450 A1 | 9/2006 | O'Donovan |
| 2006/0260959 A1 | 11/2006 | Patterson et al. |
| 2006/0275801 A1 | 12/2006 | Henkin |
| 2006/0280650 A1 | 12/2006 | Wong et al. |
| 2006/0292035 A1 | 12/2006 | Gould et al. |
| 2007/0006390 A1 | 1/2007 | Clamen |
| 2007/0009390 A1 | 1/2007 | Giusti |
| 2007/0015177 A1 | 1/2007 | Maron et al. |
| 2007/0031880 A1 | 2/2007 | Lou et al. |
| 2007/0087369 A1 | 4/2007 | Chen et al. |
| 2007/0111206 A1 | 5/2007 | Tyagi |
| 2007/0134134 A1 | 6/2007 | Watts et al. |
| 2007/0135515 A1 | 6/2007 | Bringmann et al. |
| 2007/0141582 A1 | 6/2007 | Li et al. |
| 2007/0166198 A1 | 7/2007 | Sangha et al. |
| 2007/0170142 A1 | 7/2007 | Cho |
| 2007/0178508 A1 | 8/2007 | Kamata et al. |
| 2007/0218512 A1 | 9/2007 | Strongin et al. |
| 2007/0231852 A1 | 10/2007 | Oppedahl et al. |
| 2007/0249961 A1 | 10/2007 | Morrison et al. |
| 2007/0272689 A1 | 11/2007 | Mitsuhashi |
| 2007/0280042 A1 | 12/2007 | Yamanaka |
| 2007/0287149 A1 | 12/2007 | Shomi et al. |
| 2007/0299363 A1 | 12/2007 | Wong |
| 2008/0003574 A1 | 1/2008 | Michalik et al. |
| 2008/0026375 A1 | 1/2008 | Chen |
| 2008/0067084 A1 | 3/2008 | Patterson et al. |
| 2008/0124714 A1 | 5/2008 | Shuber et al. |
| 2008/0154566 A1 | 6/2008 | Myres et al. |
| 2008/0156674 A1 | 7/2008 | Correale et al. |
| 2008/0187979 A1 | 9/2008 | Mori |
| 2008/0213877 A1 | 9/2008 | Hicks |
| 2008/0226506 A1 | 9/2008 | Ohashi et al. |
| 2008/0261229 A1 | 10/2008 | Oppedahl et al. |
| 2008/0293156 A1 | 11/2008 | Smith et al. |
| 2008/0311214 A1 | 12/2008 | Rao |
| 2009/0005705 A1 | 1/2009 | Wan et al. |
| 2009/0022631 A1 | 1/2009 | Ohashi et al. |
| 2009/0024060 A1 | 1/2009 | Darrigrand et al. |
| 2009/0054809 A1 | 2/2009 | Morishita et al. |
| 2009/0075289 A1 | 3/2009 | Zhang et al. |
| 2009/0100944 A1 | 4/2009 | Newby |
| 2009/0123976 A1 | 5/2009 | Birnboim et al. |
| 2009/0133366 A1 | 5/2009 | Cronin et al. |
| 2009/0162866 A1 | 6/2009 | Birnboim |
| 2009/0162924 A1 | 6/2009 | Birnboim |
| 2009/0205506 A1 | 8/2009 | Lin |
| 2009/0216213 A1 | 8/2009 | Muir et al. |
| 2009/0253127 A1 | 10/2009 | Gaudreau et al. |
| 2009/0258411 A1 | 10/2009 | Petithory et al. |
| 2009/0280479 A1 | 11/2009 | Hoon et al. |
| 2009/0297558 A1 | 12/2009 | Raviv et al. |
| 2009/0312285 A1 | 12/2009 | Fischer et al. |
| 2010/0081279 A1 | 4/2010 | Palmer |
| 2010/0099149 A1 | 4/2010 | Birnboim et al. |
| 2010/0120078 A1 | 5/2010 | Baker |
| 2010/0121046 A1 | 5/2010 | Ahlquist et al. |
| 2010/0137741 A1 | 6/2010 | Slowey et al. |
| 2010/0178210 A1 | 7/2010 | Hogan et al. |
| 2010/0179072 A1 | 7/2010 | Yount |
| 2010/0184069 A1 | 7/2010 | Fernando et al. |
| 2010/0209930 A1 | 8/2010 | Fernando |
| 2010/0248250 A1 | 9/2010 | Tanigami et al. |
| 2010/0248363 A1 | 9/2010 | Hogan et al. |
| 2010/0255481 A1 | 10/2010 | Akesaka et al. |
| 2010/0255484 A1 | 10/2010 | Halverson et al. |
| 2010/0258457 A1 | 10/2010 | Seelhofer |
| 2010/0273218 A1 | 10/2010 | Birnboim et al. |
| 2011/0014658 A1 | 1/2011 | Birnboim et al. |
| 2011/0020195 A1 | 1/2011 | Luotola |
| 2011/0060137 A1 | 3/2011 | Tanigami et al. |
| 2011/0081363 A1 | 4/2011 | Whitney et al. |
| 2011/0085951 A1 | 4/2011 | Nakahana et al. |
| 2011/0127294 A1 | 6/2011 | Pearcy et al. |
| 2011/0152851 A1 | 6/2011 | Formica |
| 2011/0183328 A1 | 7/2011 | Taylor et al. |
| 2011/0183332 A1 | 7/2011 | Nagaoka et al. |
| 2011/0189673 A1 | 8/2011 | Tanigami et al. |
| 2011/0207621 A1 | 8/2011 | Montagu et al. |
| 2011/0212002 A1 | 9/2011 | Curry et al. |
| 2011/0236895 A1 | 9/2011 | Tanigami et al. |
| 2011/0239717 A1 | 10/2011 | Fuentes |
| 2011/0244461 A1 | 10/2011 | Tanigami et al. |
| 2011/0300550 A1 | 12/2011 | Tanigami |
| 2012/0024861 A1 | 2/2012 | Otsuka et al. |
| 2012/0024862 A1 | 2/2012 | Otsuka et al. |
| 2012/0028296 A1 | 2/2012 | Poll et al. |
| 2012/0046574 A1 | 2/2012 | Skakoon |
| 2012/0048827 A1 | 3/2012 | Levin |
| 2012/0052572 A1 | 3/2012 | Whitney |
| 2012/0058553 A1 | 3/2012 | Haywood et al. |
| 2012/0061392 A1 | 3/2012 | Beach et al. |
| 2012/0064525 A1 | 3/2012 | Asakura et al. |

(56) References Cited

U.S. PATENT DOCUMENTS

| | | |
|---|---|---|
| 2012/0064535 A1 | 3/2012 | Tanigami et al. |
| 2012/0070830 A1 | 3/2012 | Eshoo et al. |
| 2012/0083597 A1 | 4/2012 | Okamoto et al. |
| 2012/0100529 A1 | 4/2012 | Fischer et al. |
| 2012/0141341 A1 | 6/2012 | Bartfeld et al. |
| 2012/0164648 A1 | 6/2012 | Han et al. |
| 2012/0285844 A1 | 11/2012 | Jones |
| 2012/0288956 A1 | 11/2012 | Ahlquist et al. |
| 2012/0325721 A1 | 12/2012 | Plante |
| 2013/0026691 A1 | 1/2013 | Cahill et al. |
| 2013/0053254 A1 | 2/2013 | Hollander |
| 2013/0071847 A1 | 3/2013 | Burnett et al. |
| 2013/0092690 A1 | 4/2013 | Skakoon |
| 2013/0164738 A1 | 6/2013 | Becker |
| 2013/0344615 A1 | 12/2013 | Bodner et al. |
| 2014/0054508 A1 | 2/2014 | Fernando |
| 2014/0067355 A1 | 3/2014 | Noto et al. |
| 2014/0080112 A1 | 3/2014 | Ryan et al. |
| 2014/0217197 A1 | 8/2014 | Selby et al. |
| 2014/0228233 A1 | 8/2014 | Pawlowski et al. |
| 2014/0278138 A1 | 9/2014 | Barber et al. |
| 2014/0316302 A1 | 10/2014 | Nonnemacher et al. |
| 2014/0329251 A1 | 11/2014 | Moerman et al. |
| 2014/0336159 A1 | 11/2014 | Clark et al. |
| 2015/0056716 A1 | 2/2015 | Oyler et al. |
| 2015/0100243 A1 | 4/2015 | Myres et al. |
| 2015/0104803 A1 | 4/2015 | Birnboim |
| 2017/0016807 A1 | 1/2017 | Biadillah et al. |
| 2017/0072393 A1 | 3/2017 | Jackson et al. |
| 2017/0130219 A1 | 5/2017 | Birnboim et al. |
| 2017/0226469 A1 | 8/2017 | Birnboim et al. |
| 2018/0031543 A1 | 2/2018 | Andrews et al. |
| 2018/0313726 A1 | 11/2018 | Biadillah et al. |
| 2019/0210778 A1 | 7/2019 | Muir et al. |
| 2019/0358628 A1 | 11/2019 | Curry et al. |
| 2020/0239931 A1 | 7/2020 | Birnboim et al. |
| 2020/0316493 A1 | 10/2020 | Birnboim et al. |
| 2020/0354769 A1 | 11/2020 | Birnboim |
| 2020/0362395 A1 | 11/2020 | Birnboim |
| 2020/0398267 A1 | 12/2020 | Biadillah et al. |
| 2021/0198717 A1 | 7/2021 | Birnboim et al. |

FOREIGN PATENT DOCUMENTS

| | | |
|---|---|---|
| CA | 1326809 C | 2/1994 |
| CA | 2 315 257 A1 | 7/1999 |
| CA | 2 236 240 A1 | 10/1999 |
| CA | 2 384 368 A1 | 3/2001 |
| CA | 2 142 910 C | 8/2002 |
| CA | 2 488 769 A1 | 12/2003 |
| CA | 101498 S | 1/2004 |
| CA | 2 515 039 A1 | 8/2004 |
| CA | 2 522 446 A1 | 11/2004 |
| CA | 2 567 720 A1 | 12/2005 |
| CA | 2 567 599 A1 | 7/2006 |
| CA | 2 632 614 A1 | 6/2007 |
| CA | 113861 S | 8/2007 |
| CA | 118249 S | 8/2007 |
| CA | 2 664 696 A1 | 4/2008 |
| CA | 2 703 884 A1 | 5/2009 |
| CA | 2 806 670 A1 | 2/2012 |
| CA | 2 806 734 A1 | 2/2012 |
| CA | 2 807 242 A1 | 2/2012 |
| CN | 2598551 Y | 1/2004 |
| CN | 1856570 A | 11/2006 |
| CN | 101153263 A | 4/2008 |
| CN | 101175853 A | 5/2008 |
| CN | 101253273 A | 8/2008 |
| CN | 101370425 B | 2/2009 |
| CN | 101509041 A | 8/2009 |
| CN | 201348573 Y | 11/2009 |
| CN | 102032998 A | 4/2011 |
| CN | 103890163 A | 6/2014 |
| DE | 25 54 379 | 6/1976 |
| DE | 197 20 153 A1 | 12/1997 |
| DE | 199 50 884 A1 | 4/2001 |
| DE | 102 19 117 C1 | 10/2003 |
| DE | 203 13 316 | 10/2003 |
| DE | 10219117 C1 | 10/2003 |
| EM | 000522339-0001 | 4/2006 |
| EM | 000522339-0002 | 4/2006 |
| EP | 0 013 803 A2 | 8/1980 |
| EP | 0 215 735 A1 | 3/1987 |
| EP | 0 240 341 A2 | 10/1987 |
| EP | 0 273 015 A2 | 6/1988 |
| EP | 0 285 439 A2 | 10/1988 |
| EP | 0 338 591 A2 | 10/1989 |
| EP | 0 487 028 A2 | 5/1992 |
| EP | 0 586 024 B1 | 3/1994 |
| EP | 0 265 519 B1 | 9/1995 |
| EP | 0 734 684 A1 | 10/1996 |
| EP | 0 939 118 A1 | 9/1999 |
| EP | 1 207 208 A2 | 5/2002 |
| EP | 1 362 927 A1 | 11/2003 |
| EP | 1 391 520 A1 | 2/2004 |
| EP | 1 527 172 B1 | 11/2008 |
| EP | 1 238 103 B1 | 1/2009 |
| EP | 2 075 824 A1 | 7/2009 |
| EP | 1 506 995 B1 | 10/2009 |
| EP | 2 110 442 A1 | 10/2009 |
| EP | 2 196 803 A1 | 6/2010 |
| EP | 2 214 830 A1 | 8/2010 |
| EP | 2 218 791 A1 | 8/2010 |
| EP | 2 218 792 A1 | 8/2010 |
| EP | 2 287 331 A1 | 2/2011 |
| EP | 2 314 677 A1 | 4/2011 |
| EP | 2 338 989 A1 | 6/2011 |
| EP | 2 392 670 A1 | 12/2011 |
| EP | 2 535 428 A2 | 12/2012 |
| FR | 2279378 A1 | 2/1976 |
| GB | 1 403 274 A | 8/1975 |
| GB | 725784 A | 3/1995 |
| GB | 2457654 B | 5/2012 |
| JP | S60-4433 U | 1/1985 |
| JP | S62-253395 A | 11/1987 |
| JP | S63-070954 U | 5/1988 |
| JP | 2-42972 A | 2/1990 |
| JP | H05-99923 A | 4/1993 |
| JP | S62-153725 A | 4/1993 |
| JP | 5-94765 U | 12/1993 |
| JP | H6-78282 | 11/1994 |
| JP | H09-500723 A | 1/1997 |
| JP | H09168399 A | 6/1997 |
| JP | 09-193977 | 7/1997 |
| JP | H10-132824 A | 5/1998 |
| JP | H10-273161 A | 10/1998 |
| JP | H10-512140 A | 11/1998 |
| JP | 10-332734 | 12/1998 |
| JP | 11183468 A | 7/1999 |
| JP | 2000-501191 A | 2/2000 |
| JP | 2000-501931 A1 | 2/2000 |
| JP | 2000-508171 A | 7/2000 |
| JP | 2001-524321 A | 12/2001 |
| JP | 2002-156317 A | 5/2002 |
| JP | 2002-514084 A | 5/2002 |
| JP | 2003-344232 A | 12/2003 |
| JP | 2004008094 A | 1/2004 |
| JP | 2004008107 A | 1/2004 |
| JP | 2004222795 A | 8/2004 |
| JP | 2005-536550 A | 12/2005 |
| JP | 2006115983 A | 5/2006 |
| JP | 2007-248170 A | 9/2007 |
| JP | 4092139 B | 5/2008 |
| JP | 4092141 B | 5/2008 |
| JP | 2009-051555 A | 3/2009 |
| JP | 2009-518244 A | 5/2009 |
| JP | 2009-522542 A | 6/2009 |
| JP | 2010-008106 A | 1/2010 |
| JP | 2010-505396 A | 2/2010 |
| JP | 2010-213660 A | 9/2010 |
| JP | 2011-36247 A | 2/2011 |
| JP | 2012-523572 A | 10/2012 |
| JP | 2014-531902 A | 12/2014 |
| JP | 2015-500988 A | 1/2015 |

(56) References Cited

FOREIGN PATENT DOCUMENTS

| | | |
|---|---|---|
| JP | 58-96365 B2 | 3/2016 |
| JP | 59-66756 B2 | 8/2016 |
| RU | 2101354 C1 | 1/1998 |
| RU | 2241004 C2 | 11/2004 |
| WO | WO 87/06706 A1 | 11/1987 |
| WO | WO 89/006704 A1 | 7/1989 |
| WO | WO 91/002740 A1 | 3/1991 |
| WO | WO 92/17110 A1 | 10/1992 |
| WO | WO 93/20235 A1 | 10/1993 |
| WO | WO 94/12657 A1 | 6/1994 |
| WO | WO 94/12881 A2 | 6/1994 |
| WO | WO 94/29691 A | 12/1994 |
| WO | WO 96/00228 A1 | 1/1996 |
| WO | WO 96/14017 A1 | 5/1996 |
| WO | WO 96/20403 A1 | 7/1996 |
| WO | WO 97/005248 A2 | 2/1997 |
| WO | WO 97/019191 A1 | 5/1997 |
| WO | WO 97/21 102 A1 | 6/1997 |
| WO | WO 97/21605 A1 | 6/1997 |
| WO | WO 97/24979 A1 | 7/1997 |
| WO | WO 97/38313 A1 | 10/1997 |
| WO | WO 97/48492 A1 | 12/1997 |
| WO | WO 98/03265 A1 | 1/1998 |
| WO | WO 98/04899 A1 | 2/1998 |
| WO | WO 1998/012351 A1 | 3/1998 |
| WO | WO 98/38917 A1 | 9/1998 |
| WO | WO 98/044158 A1 | 10/1998 |
| WO | WO 98/53075 A2 | 11/1998 |
| WO | WO 98/58081 A1 | 12/1998 |
| WO | WO 99/000521 A1 | 1/1999 |
| WO | WO 99/27139 A1 | 6/1999 |
| WO | WO 99/029904 A2 | 6/1999 |
| WO | WO 00/008136 A1 | 2/2000 |
| WO | WO 00/10884 A1 | 3/2000 |
| WO | WO 00/029618 A1 | 5/2000 |
| WO | WO 00/031303 A2 | 6/2000 |
| WO | WO 00/50640 A1 | 8/2000 |
| WO | WO 00/66606 A1 | 11/2000 |
| WO | WO 00/78150 A1 | 12/2000 |
| WO | WO 01/034844 A1 | 5/2001 |
| WO | WO 01/40277 A2 | 6/2001 |
| WO | WO 01/42503 A2 | 6/2001 |
| WO | WO 01/060517 A2 | 8/2001 |
| WO | WO 02/044691 A2 | 6/2002 |
| WO | WO 02/056030 A2 | 7/2002 |
| WO | WO 02/059379 A2 | 8/2002 |
| WO | WO 02/088296 A1 | 11/2002 |
| WO | WO 03/033739 A1 | 4/2003 |
| WO | WO 03/104251 A2 | 12/2003 |
| WO | WO 2004/017895 A2 | 3/2004 |
| WO | WO 2004/033336 A1 | 4/2004 |
| WO | WO 2004/033470 A2 | 4/2004 |
| WO | WO 2004/046348 A1 | 6/2004 |
| WO | WO 2004/072229 A2 | 8/2004 |
| WO | WO 2004/094635 A2 | 11/2004 |
| WO | WO 2004/107985 A1 | 12/2004 |
| WO | WO 2004/108205 A1 | 12/2004 |
| WO | WO 2005/010186 A1 | 2/2005 |
| WO | WO 2005/023667 A1 | 3/2005 |
| WO | WO 2005/051775 A2 | 6/2005 |
| WO | WO 2005/090189 A1 | 9/2005 |
| WO | WO 2005/113769 A1 | 12/2005 |
| WO | WO 2005/123960 A1 | 12/2005 |
| WO | WO 2006/035558 A1 | 4/2006 |
| WO | WO 2006/072803 A2 | 7/2006 |
| WO | WO 2006/073472 A2 | 7/2006 |
| WO | WO 2006/076820 A1 | 7/2006 |
| WO | WO 2006/082419 A1 | 8/2006 |
| WO | WO 2006/096973 A1 | 9/2006 |
| WO | WO 2006/133701 A2 | 12/2006 |
| WO | WO 2007/050327 A2 | 5/2007 |
| WO | WO 2007/051303 A1 | 5/2007 |
| WO | WO 2007/057744 A2 | 5/2007 |
| WO | WO 2007/068094 A1 | 6/2007 |
| WO | WO 2007/109586 A2 | 9/2007 |
| WO | WO 2008/021995 A1 | 2/2008 |
| WO | WO 2008/040126 A1 | 4/2008 |
| WO | WO 2008/089198 A1 | 7/2008 |
| WO | WO 2008/152980 A1 | 12/2008 |
| WO | WO 2009/067518 A1 | 5/2009 |
| WO | WO 2009/070638 A1 | 6/2009 |
| WO | WO 2009/139632 A1 | 11/2009 |
| WO | WO 2010/027283 A1 | 3/2010 |
| WO | WO 2010/028382 A2 | 3/2010 |
| WO | WO 2010/031007 A2 | 3/2010 |
| WO | WO 2010/064634 A1 | 6/2010 |
| WO | WO 2010/089102 A1 | 8/2010 |
| WO | WO 2010/090030 A1 | 8/2010 |
| WO | WO 2010/114101 A1 | 10/2010 |
| WO | WO 2010/120818 A2 | 10/2010 |
| WO | WO 2010/122981 | 10/2010 |
| WO | WO2010/123908 A1 | 10/2010 |
| WO | WO2011/116481 A1 | 9/2011 |
| WO | WO 2011/157683 A1 | 12/2011 |
| WO | WO 2012/016287 A2 | 2/2012 |
| WO | WO 2012/018638 A2 | 2/2012 |
| WO | WO 2012/018639 A2 | 2/2012 |
| WO | WO 2012/098254 A1 | 7/2012 |
| WO | WO 2012/145390 A1 | 10/2012 |
| WO | WO 2012/177656 A2 | 12/2012 |
| WO | WO 2012/177656 A3 | 12/2012 |
| WO | WO 2013/041854 A1 | 3/2013 |
| WO | WO 2013/045457 A1 | 4/2013 |
| WO | WO 2013/067353 A1 | 5/2013 |
| WO | WO 2013/083687 A1 | 6/2013 |
| WO | WO 2013/188740 A1 | 12/2013 |
| WO | WO 2014/049022 A1 | 4/2014 |
| WO | WO 2015/017701 A1 | 2/2015 |
| WO | WO 2015/112496 A2 | 7/2015 |

OTHER PUBLICATIONS

Exhibit 1 of Declaration of DeForest McDuff, Ph.D., dated and filed Aug. 24, 2015: Curriculum vitae of DeForest McDuff, Ph.D., filed Aug. 24, 2015 (12 pages).

Exhibit 1 of Declaration of John M. Collins in Support of DNA Genotek's Reply in Support of the Motion for Preliminary Injunction, filed Nov. 5, 2015: Curriculum vitae of John M. Collins, Ph.D., filed Nov. 5, 2015 (5 pages).

Exhibit 1 of Redacted Declaration of Brian M. Kramer in Support of Plaintiff DNA Genotek Inc.'s Reply Brief in Support of Its Motion for Preliminary Injunction, filed Nov. 11, 2015: a true and correct copy of excerpted pages from the deposition of Terry Layton, dated Oct. 14, 2015 (40 pages).

Exhibit 1 of Redacted Public Version of the Declaration of Brian M. Kramer in Support of DNA Genotek Inc.'s Answering Brief in Response to Defendant's Motion to Dismiss, filed Oct. 7, 2015: a true and correct copy of excerpted pages from the deposition of Gregg Williams, taken on Sep. 22, 2015 Redacted Version in its Entirety (2 pages).

Exhibit 1 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct copy of WO 2015/017701, published on Feb. 5, 2015 (23 pages).

Exhibit 1 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct copy of a compilation of web pages retrieved from the website http://dna.ancestry.com/that were printed Oct. 15, 2015 (4 pages).

Exhibit 10 of Declaration of John M. Collins in Support of DNA Genotek's Reply in Support of the Motion for Preliminary Injunction, filed Nov. 5, 2015: Reply to Office Action for U.S. Appl. No. 12/096,767, dated Feb. 2, 2012 (7 pages).

Exhibit 10 of Redacted Public Version of the Declaration of Brian M. Kramer in Support of DNA Genotek Inc.'s Answering Brief in Response to Defendant's Motion to Dismiss, filed Oct. 7, 2015: are true and correct copies of documents produced by Spectrum,

(56) References Cited

OTHER PUBLICATIONS bearing Bates Nos. SPEC00000035, SPEC00000043, SPEC00000053, and SPEC00000067, filed Oct. 7, 2015 Redacted Version in its Entirety (2 pages).
Exhibit 1001 of Resubmitted Petition for Inter Partes Review of U.S. Pat. No. 8,221,381, Inter Partes Review No. IPR 2016-00060, dated Nov. 5, 2015: U.S. Pat. No. 8,221,381 (Muir et al.) (25 pages).
Exhibit 1002 of Resubmitted Petition for Inter Partes Review of U.S. Pat. No. 8,221,381, Inter Partes Review No. IPR 2016-00060, dated Nov. 5, 2015: File History of U.S. Pat. No. 8,221,381 (401 pages).
Exhibit 1003 of Resubmitted Petition for Inter Partes Review of U.S. Pat. No. 8,221,381, Inter Partes Review No. IPR 2016-00060, dated Nov. 5, 2015: Declaration of Terry N. Layton, Ph.D. (130 pages).
Exhibit 1004 of Resubmitted Petition for Inter Partes Review of U.S. Pat. No. 8,221,381, Inter Partes Review No. IPR 2016-00060, dated Nov. 5, 2015: Curriculum Vitae of Terry N. Layton, Ph.D. (4 pages).
Exhibit 1005 of Resubmitted Petition for Inter Partes Review of U.S. Pat. No. 8,221,381, Inter Partes Review No. IPR 2016-00060, dated Nov. 5, 2015: Plaintiff DNA Genotek Inc.'s Opening Brief in Support of Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Aug. 24, 2015 (26 pages).
Exhibit 1006 of Resubmitted Petition for Inter Partes Review of U.S. Pat. No. 8,221,381, Inter Partes Review No. IPR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015 (15 pages).
Exhibit 1007 of Resubmitted Petition for Inter Partes Review of U.S. Pat. No. 8,221,381, Inter Partes Review No. IPR 2016-00060, dated Nov. 5, 2015: U.S. Pat. No. 7,645,424 (O'Donovan) (8 pages).
Exhibit 1008 of Resubmitted Petition for Inter Partes Review of U.S. Pat. No. 8,221,381, Inter Partes Review No. IPR 2016-00060, dated Nov. 5, 2015: WO-2003/104251-A2 (DNA Genotek Inc) (50 pages).
Exhibit 1009 of Resubmitted Petition for Inter Partes Review of U.S. Pat. No. 8,221,381, Inter Partes Review No. IPR 2016-00060, dated Nov. 5, 2015: U.S. Pat. No. 6,152,296 (Shih) (9 pages).
Exhibit 1010 of Resubmitted Petition for Inter Partes Review of U.S. Pat. No. 8,221,381, Inter Partes Review No. IPR 2016-00060, dated Nov. 5, 2015: WO-98/03265-A1 (Kyoritsu Chemical—check Lab., Corp) (44 pages).
Exhibit 1011 of Resubmitted Petition for Inter Partes Review of U.S. Pat. No. 8,221,381, Inter Partes Review No. IPR 2016-00060, dated Nov. 5, 2015: (Certified English Translation) WO-98/03265-A1 (Kyoritsu Chemical—check Lab., Corp) (30 pages).
Exhibit 1012 of Resubmitted Petition for Inter Partes Review of U.S. Pat. No. 8,221,381, Inter Partes Review No. IPR 2016-00060, dated Nov. 5, 2015: DE-199 50 884-A1 (Wella Ag) (16 pages).
Exhibit 1013 of Resubmitted Petition for Inter Partes Review of U.S. Pat. No. 8,221,381, Inter Partes Review No. IPR 2016-00060, dated Nov. 5, 2015: (Certified English Translation) DE-199 50884-A1 (Wella Ag) (8 pages).
Exhibit 1014 of Resubmitted Petition for Inter Partes Review of U.S. Pat. No. 8,221,381, Inter Partes Review No. IPR 2016-00060, dated Nov. 5, 2015: U.S. Pat. No. 6,228,323 (Asgharian et al.) (23 pages).
Exhibit 1015 of Resubmitted Petition for Inter Partes Review of U.S. Pat. No. 8,221,381, Inter Partes Review No. IPR 2016-00060, dated Nov. 5, 2015: The American Heritage Dictionary of the English Language, Fourth Edition (2000) (definitions of: "corner"; "fastener"; "inert"; "reservoir"; "vial") (8 pages).
Exhibit 1016: Defendants' Brief in Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015 (37 pages).

Exhibit 1017 of Resubmitted Petition for Inter Partes Review of U.S. Pat. No. 8,221,381, Inter Partes Review No. IPR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015 (38 pages).
Exhibit 1018 of Resubmitted Petition for Inter Partes Review of U.S. Pat. No. 8,221,381, Inter Partes Review No. IPR 2016-00060, dated Nov. 5, 2015: U.S. Appl. No. 60/523,104, filed Nov. 19, 2003 by Michael O'Donovan (9 pages).
Exhibit 1019 of Resubmitted Petition for Inter Partes Review of U.S. Pat. No. 8,221,381, Inter Partes Review No. IPR 2016-00060, dated Nov. 5, 2015: Numerical Designation of U.S. Pat. No. 8,221,381 Claim Element or Limitation, dated Nov. 5, 2015 (4 pages).
Exhibit 11 of Declaration of John M. Collins in Support of DNA Genotek's Reply in Support of the Motion for Preliminary Injunction, dated Nov. 5, 2015, filed Nov. 5, 2015: Notice of Allowability for U.S. Appl. No. 12/096,767, dated Apr. 1, 2012 (4 pages).
Exhibit 11 of Redacted Public Version of the Declaration of Brian M. Kramer in Support of DNA Genotek Inc.'s Answering Brief in Response to Defendant's Motion to Dismiss, filed Oct. 7, 2015: a true and correct copy of a document retrieved from the Delaware Division of Corporations showing Ancestry.com DNA, LLC is a Delaware corporation, filed Oct. 7, 2015 (2 pages).
Exhibit 2 of Declaration of Brian M. Kramer in Support of DNA Genotek Inc.'s Opposition to Defendants' "Unopposed" Motion for Leave to File Surreply and DNA Genotek Inc.'s Motion to Strike Unauthorized Expert Declaration, filed Nov. 20, 2015: a true and correct copy of an email chain between attorneys for Spectrum and attorneys for DNA Genotek, dated Nov. 19, 2015, bearing the subject line "RE: PAC-#1209828-v1 Draft Unopposed motion for leave to file surreplv.DOCX." (2 pages).
Exhibit 2 of Declaration of DeForest McDuff, Ph.D., dated and filed Aug. 24, 2015: Spectrum Website, Who We Are, http://www.spectrum-dna.com/about-us/, filed Aug. 24, 2015 (5 pages).
Exhibit 2 of Declaration of John M. Collins in Support of DNA Genotek's Reply in Support of the Motion for Preliminary Injunction, filed Nov. 5, 2015: U.S. Pat. No. 8,221,381 82, Jul. 17, 2012 (25 pages).
Exhibit 2 of Redacted Declaration of Brian M. Kramer in Support of Plaintiff DNA Genotek Inc.'s Reply Brief in Support of Its Motion for Preliminary Injunction, filed Nov. 11, 2015: a true and correct copy of the excerpted pages from the deposition of Thomas R. Varner, dated Oct. 14, 2015 (20 pages).
Exhibit 2 of Redacted Public Version of the Declaration of Brian M. Kramer in Support of DNA Genotek Inc.'s Answering Brief in Response to Defendant's Motion to Dismiss, filed Oct. 7, 2015: a true and correct copy of compilation of web pages retrieved from Spectrum DNA website, http://www.spectrum-dna.com/, filed Oct. 7, 2015(3 pages).
Exhibit 2 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct copy of the list of the PTO's publicly-searchable assignment database to determine the number of U.S. patent and U.S. published patent applications currently assigned to the defendant in this case, Ancestry.com DNA, LLC, filed Sep. 14, 2015 (29 pages).
Exhibit 2 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct copy of the fully executed Manufacturing Agreement between Spectrum Packaging, L.L.C. and Ancestry.com DNA, LLC, which was produced by Spectrum in this action with Bates Nos. SPEC00000015-34, filed Oct. 26, 2015 Redacted Version in its Entirety (2 pages).
Exhibit 3 of Declaration of DeForest McDuff, Ph.D., dated and filed Aug. 24, 2015: Spectrum Website, Saliva DNA Collection Device, http://www.sgectrum-dna.com/saliva-dnacollectiondevice/, filed Aug. 24, 2015 (4 pages).

(56) References Cited

OTHER PUBLICATIONS

Exhibit 3 of Declaration of John M. Collins in Support of DNA Genotek's Reply in Support of the Motion for Preliminary Injunction, filed Nov. 5, 2015: U.S. Pat. No. 7,645,424 B2, Jan. 12, 2010 (9 pages).
Exhibit 3 of Redacted Declaration of Brian M. Kramer in Support of Plaintiff DNA Genotek Inc.'s Reply Brief in Support of Its Motion for Preliminary Injunction, filed Nov. 11, 2015: a true and correct copy of excerpted pages from the deposition of Ian Curry, dated Sep. 4, 2015 (6 pages).
Exhibit 3 of Redacted Public Version of the Declaration of Brian M. Kramer in Support of DNA Genotek Inc.'s Answering Brief in Response to Defendant's Motion to Dismiss, filed Oct. 7, 2015: a true and correct copy of excerpt pages from the Court's Hearing Transcript, dated Sep. 10, 2015 (3 pages).
Exhibit 3 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct copy of Product Design—Customization Requirements Documents between Ancestry and DNA Genotek, dated Feb. 13, 2012, and signed by Mr. Ken Chahine (8 pages).
Exhibit 3 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct copy of the fully executed Amendment to the Manufacturing Agreement between Ancestry.com DNA, LLC and Spectrum Packaging, L.L.C., which was produced by Spectrum in this action with BatesNos. SPEC0000000?-14, filed Oct. 26, 2015 Redacted Version in its Entirety (2 pages).
Exhibit 3: a true and correct copy of the file attached to the e-mail appearing as Exhibit 2, which bears the file name "MoFo edits Draft_Unopposed_motion_for_leave_to_file_surreply(2).docx.", filed Nov. 20, 2015 (3 pages).
Exhibit 4 of Declaration of DeForest McDuff, Ph.D., dated and filed Aug. 24, 2015: Spectrum, Marketing Sheet, http://spectrum-dna.com/wg-content/ugloads/2015/08/Marketing-Sheet-for-Saliva-Kit.pdf, filed Aug. 24, 2015 (2 pages).
Exhibit 4 of Declaration of John M. Collins in Support of DNA Genotek's Reply in Support of the Motion for Preliminary Injunction, filed Nov. 5, 2015: English translation of WO 98/03265, published Jan. 29, 1998 (30 pages).
Exhibit 4 of Redacted Declaration of Brian M. Kramer in Support of Plaintiff DNA Genotek Inc.'s Reply Brief in Support of Its Motion for Preliminary Injunction, filed Nov. 11, 2015: a true and correct copy of Deposition Exhibit DX-4 to the deposition of Ian Curry, dated Sep. 4, 2015, Redacted Version in its Entirety (2 pages).
Exhibit 4 of Redacted Public Version of the Declaration of Brian M. Kramer in Support of DNA Genotek Inc.'s Answering Brief in Response to Defendant's Motion to Dismiss, filed Oct. 7, 2015: a true and correct copy of Ancestry.corn's webpage Delaware Genealogy & Delaware Family History Resources, http://search.ancestry.com/Places/US/Delaware/, filed on Oct. 7, 2015 (3 pages).
Exhibit 4 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: US 2009/0216213, Aug. 27, 2009 (25 pages).
Exhibit 4 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct copy of the fully executed Purchase and Sales Commission Agreement between Ancestry.com DNA, LLC and Spectrum Packaging, L.L.C., which was produced by Spectrum in this action with BatesNos. SPEC00000097-109, filed Oct. 26, 2015 Redacted Version in its Entirety (2 pages).
Exhibit 5 of Declaration of DeForest McDuff, Ph.D., dated and filed Aug. 24, 2015: Spectrum Website, Custom Packaging, http://www.spectrum-dna.com/custom-gackaging/, filed Aug. 24, 2015 (9 pages).

Exhibit 5 of Declaration of John M. Collins in Support of DNA Genotek's Reply in Support of the Motion for Preliminary Injunction, filed Nov. 5, 2015: U.S. Pat. No. 7,537,132 82, May 26, 2009 (6 pages).
Exhibit 5 of Redacted Declaration of Brian M. Kramer in Support of Plaintiff DNA Genotek Inc.'s Reply Brief in Support of Its Motion for Preliminary Injunction, filed Nov. 11, 2015: a true and correct copy of excerpted pages from the deposition of DeForest McDuff, dated Sep. 10, 2015 (8 pages).
Exhibit 5 of Redacted Public Version of the Declaration of Brian M. Kramer in Support of DNA Genotek Inc.'s Answering Brief in Response to Defendant's Motion to Dismiss, filed Oct. 7, 2015: a true and correct copy of a document titled, "Saliva DNA Collection," which was retrieved from http://www.spectrum-dna.com/saliva-dnacollection-device, filed Oct. 7, 2015 (3 pages).
Exhibit 5 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct copy of Product Design—Customization Requirements Documents between Ancestry and DNA Genotek, dated Sep. 20, 2012, and signed by Mr. Kenneth Chahine (9 pages).
Exhibit 5 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct copy of excerpts taken from the transcript of the deposition of Gregg Williams, which was taken on Sep. 22, 2015, filed Oct. 26, 2015 Redacted Version in its Entirety (2 pages).
Exhibit 6 of Declaration of DeForest McDuff, Ph.D., dated and filed Aug. 24, 2015: Spectrum, Clinical Data Sheet, http://spectrum-dna.com/wg-content/ugloads/2015/06/Sgectrum-Clinical-Data-Sheet.pdf, filed Aug. 24, 2015 (2 pages).
Exhibit 6 of Declaration of John M. Collins in Support of DNA Genotek's Reply in Support of the Motion for Preliminary Injunction, filed Nov. 5, 2015: substitute pp. 1 and 22 for WO 2007/068094 (PCT/CA2006/002009), filed with Declaration on Nov. 5, 2015 (3 pages).
Exhibit 6 of Redacted Public Version of the Declaration of Brian M. Kramer in Support of DNA Genotek Inc.'s Answering Brief in Response to Defendant's Motion to Dismiss, filed Oct. 7, 2015: a true and correct copy of a document titled, "Saliva Kit for DNA Collection," which was retrieved from http://www.spectrum-dna.com/wpcontent/uploads/2015/09/Spectrum-Clinical-Data-Sheet.pdf, filed October/, 2015 (2 pages).
Exhibit 6 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct copy of DNA Genotek's legal notice, filed Sep. 14, 2015 (3 pages).
Exhibit 7 of Declaration of DeForest McDuff, Ph.D., dated and filed Aug. 24, 2015: Saliva Collection Instructions, http://spectrum-dna.com/wgcontent/ uploads/2015/06/Saliva-CollectionInstructions.pdf, filed Aug. 24, 2015 (2 pages).
Exhibit 7 of Declaration of John M. Collins in Support of DNA Genotek's Reply in Support of the Motion for Preliminary Injunction, filed Nov. 5, 2015: Preliminary Amendment for U.S. Appl. No. 12/096,767, dated Jun. 9, 2008 (4 pages).
Exhibit 7 of Redacted Public Version of the Declaration of Brian M. Kramer in Support of DNA Genotek Inc.'s Answering Brief in Response to Defendant's Motion to Dismiss, filed Oct. 7, 2015: a true and correct copy of a document produced by Spectrum, bearing Bates Nos. SPEC00000015-SPEC00000034, filed Oct. 1, 2015 Redacted Version in its Entirety (2 pages).
Exhibit 7 of Redacted Public Version of the Declaration of Brian M. Kramer in Support of Plaintiff DNA Genotek Inc.'s Opposition to Ancestry.com DNA, LLC's Motion to Dismiss, dated Sep. 3, 2015, filed Sep. 14, 2015: a true and correct copy of the Written Opinion of the International Searching Authority for PCT patent application publication WO 2015/017701 A 1, dated Nov. 14, 2014 (8 pages).
Exhibit 8 of Declaration of John M. Collins in Support of DNA Genotek's Reply in Support of the Motion for Preliminary Injunction, filed Nov. 5, 2015: Non-Final Office Action for U.S. Appl. No. 12/096,767, dated Dec. 27, 2011 (8 pages).

(56) References Cited

OTHER PUBLICATIONS

Exhibit 8 of Redacted Public Version of the Declaration of Brian M. Kramer in Support of DNA Genotek Inc.'s Answering Brief in Response to Defendant's Motion to Dismiss, filed Oct. 7, 2015: a true and correct copy of a document produced by Spectrum, bearing Bates No. SPEC00000007-SPEC00000014, filed Oct. 7, 2015 Redacted Version in its Entirety (2 pages).
Exhibit 9 of Declaration of John M. Collins in Support of DNA Genotek's Reply in Support of the Motion for Preliminary Injunction, filed Nov. 5, 2015: EP 0273015 A2, published Jun. 29, 1988 (9 pages).
Exhibit 9 of Redacted Public Version of the Declaration of Brian M. Kramer in Support of DNA Genotek Inc.'s Answering Brief in Response to Defendant's Motion to Dismiss, filed Oct. 7, 2015: a true and correct copy of a document produced by Spectrum, bearing Bates No. SPEC00000097-SPEC0000109, filed Oct. 7, 2015 Redacted Version in its Entirety (2 pages).
Exhibit A of Complaint, dated Jul. 30, 2015: U.S. Pat. No. 8,221,381 B2, Jul. 17, 2012 (26 pages).
Exhibit A of Complaint, dated May 4, 2015: U.S. Pat. No. 8,221,381 B2, Jul. 17, 2012 (26 pages).
Exhibit A of Declaration of Brian M. Kramer in Support of Motion for Preliminary Injunction, filed Aug. 24, 2015: Aug. 12, 2005 Articles of Incorporation of Spectrum Packaging L.L.C. (2 pages).
Exhibit A of Declaration of Ian Curry, dated and filed Aug. 24, 2015: User Instruction for DNA Genotek's Oraaene•RNA® !RE-100), filed Aug. 24, 2015 (3 pages).
Exhibit A of Declaration of Juan C. Lasheras, Ph.D., dated and filed on Aug. 24, 2015: Curriculum vitae of Juan C. Lasheras, Ph.D., filed Aug. 24, 2015 (36 pages).
Exhibit A of Declaration of Terry Layton, Ph.D. in Support of Defendants' Opposition to DNA Genotek's Motion for Preliminary Injunction, dated Oct. 2, 2015, filed Oct. 2, 2015: Curriculum vitae of Terry Layton, Ph.D., filed Oct. 2, 2015 (9 pages).
Exhibit A of Defendants' Unopposed Motion for Leave to File a Surreply in Further Opposition to Plaintiff's Motion for a Preliminary Injunction, filed Nov. 19, 2015: Surreply in Support of Defendants' Brief in Opposition to DNA Genotek's Motion for Preliminary Injunction, filed Nov. 19, 2015 (12 pages).
Exhibit A of Exhibit 1006 of Resubmitted Petition for Inter Partes Review of U.S. Pat. No. 8,221,381, Inter Partes Review No. I PR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: Curriculum vitae of Juan C. Lasheras, Ph.D., filed Aug. 24, 2015 (36 pages).
Exhibit A of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: Curriculum vitae of Terry Layton, Ph.D., filed Oct. 2, 2015 (9 pages).
Exhibit A of First Amended Complaint, dated Jul. 24, 2015: U.S. Pat. No. 8,221,381 B2, Jul. 17, 2012 (26 pages).
Exhibit A of Redacted Public Version of the Declaration of Melanie L. Mayer in Support of Defendants' Brief in Opposition to DNA Genotek's Motion for Preliminary Injunction, filed Oct. 9, 2015: a true and correct copy of a Reply to Office Action filed on Feb. 2, 2012 for patent Application U.S. Appl. No. 12/096,767, which issued as U.S. Pat. No. 8,221,381 (15 pages).
Exhibit B of Complaint, dated May 4, 2015: WO 2015/017701, Feb. 5, 2015 (22 pages).
Exhibit B of Declaration of Brian M. Kramer in Support of Motion for Preliminary Injunction, filed Aug. 24, 2015: Oct. 22, 2013 Articlesof Amendment to Articles of Organization of Spectrum Packaging L.L.C. (2 pages).

Exhibit B of Declaration of Ian Curry, dated and filed Aug. 24, 2015: Spectrum Website, Custom Packaging, http://www.spectrum-dna.com/custom-Packaging/, filed Aug. 24, 2015 (9 pages).
Exhibit B of Declaration of Juan C. Lasheras, Ph.D., dated and filed on Aug. 24, 2015: U.S. Pat. No. 8,221,381 82, Jul. 17, 2012 (26 pages).
Exhibit B of Declaration of Terry Layton, Ph.D. in Support of Defendants' Opposition to DNA Genotek's Motion for Preliminary Injunction, filed Oct. 2, 2015: U.S. Pat. No. 8,221,381 B2, Jul. 17, 2012 (26 pages).
Exhibit B of Defendants' Unopposed Motion for Leave to File a Surreply in Further Opposition to Plaintiff's Motion for a Preliminary Injunction, filed Nov. 19, 2015: Declaration of Terry Layton, Ph.D. in Support of Defendants' Surreply in Support of Defendants' Brief in Opposition to DNA Genotek's Motion for Preliminary Injunction, filed Nov. 19, 2015 (16 pages).
Exhibit B of Exhibit 1006 of Resubmitted Petition for Inter Partes Review of U.S. Pat. No. 8,221,381, Inter Partes Review No. I PR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: U.S. Pat. No. 8,221,381 B2, Jul. 17, 2012 (26 pages).
Exhibit B of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: U.S. Pat. No. 8,221,381 82, Jul. 17, 2012 (26 pages).
Exhibit B of First Amended Complaint, dated Jul. 24, 2015: a true and correct copy of WO 2015/017701 A1, Feb. 5, 2015 (22 pages).
Exhibit B of Redacted Public Version of the Declaration of Melanie L. Mayer in Support of Defendants' Brief in Opposition to DNA Genotek's Motion for Preliminary Injunction, filed Oct. 9, 2015: a true and correct copy of excerpts taken from the transcript of the deposition of Juan C. Lasheras, which was taken on Sep. 24, 2015 (40 pages).
Exhibit C of Declaration of Brian M. Kramer in Support of Motion for Preliminary Injunction, filed Aug. 24, 2015: May 6, 2015 Second Amended and Restated Articles of Organization of Spectrum Solutions L.L.C. (3 pages).
Exhibit C of Declaration of Juan C. Lasheras, Ph.D., dated and filed on Aug. 24, 2015: Spectrum Product Material Safety Data Sheet, filed Aug. 24, 2015 (11 pages).
Exhibit C of Declaration of Terry Layton, Ph.D. in Support of Defendants' Opposition to DNA Genotek's Motion for Preliminary Injunction, filed Oct. 2, 2015: Information sheet for the Spectrum Product, filed Oct. 2, 2015 (2 pages).
Joint Motion to Terminate Proceeding pursuant to 35 U.S.C § 317(A), Inter Partes Review No. IPR 2016-01467, dated Feb. 1, 2017 (5 pages).
Joint Request that the Settlement Agreement Filed Separately as Exhibit 2008 be Treated as Business Confidential Information and be Kept Separate from the Files, Inter Partes Review No. IPR 2016-01467, dated Feb. 1, 2017 (4 pages).
Petitioner Ancestry.com DNA, LLC's Request for Rehearing and Reconsideration under 37 C.F.R. § 42.71(d), Inter Partes Review No. IPR 2016-01152, dated Dec. 23, 2016 (19 pages).
Termination of Proceeding pursuant to Settlement After Institution 37 C.F.R. § 42.72, Inter Partes Review No. IPR 2016-00060, dated Feb. 3, 2017 (3 pages).
Granting Joint Motion to Terminate Proceeding and Dismissing Petitioner's Request for Rehearing and Reconsideration 37 C.F.R. § 42.72, Inter Partes Review No. IPR 2016-01152, dated Feb. 3, 2017 (3 pages).
Termination of Proceeding pursuant to Settlement Prior to Institution 37 C.F.R. § 42.72, Inter Partes Review No. 2016-01467, dated Feb. 3, 2017 (3 pages).
Report on the Filing of Determination of an Action Regarding aPatentof Trademark for U.S. Pat. No. 8,221,381, dated May 4, 2015 (1 page).

(56) References Cited

OTHER PUBLICATIONS

Action for Patent Infringement for U.S. Pat. No. 8,221,381, dated Jul. 24, 2015 (64 pages).
Joint Request that the Settlement Agreement Filed Separately as Exhibit 2004 be Treated as Business Confidential Information and be Kept Separate from the Files, Inter Partes Review No. IPR 2016-01152, dated Feb. 1, 2017 (4 pages).
Petition for Inter Partes Review of U.S. Pat. No. 8,221,381, dated Oct. 20, 2015 (69 pages).
File History of U.S. Pat. No. 8,221,381, dated Oct. 20, 2015 (400 pages).
Declaration of Terry N. Layton, Ph.D., dated Oct. 20, 2015 (130 pages).
Curriculum Vitae of Terry N. Layton, Ph.D., dated Oct. 20, 2015 (4 pages).
Plaintiff DNA Genotek Inc.'s Opening Brief in Support of Motion for Preliminary Injunction, *DNA Genotek, Inc. v. Spectrum DNA; Spectrum Solutions L.L.C., and Spectrum Packaging, LLC*, Case No. 15-cv-00661-SLR, dated Aug. 24, 2015 (26 pages).
Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015 (154 pages).
The American Heritage Dictionary of the English Language, Fourth Edition (2000) (definitions of: "corner"; "fastener"; "inert"; "reservoir"; "vial"), dated Oct. 20, 2015 (8 pages).
Defendants' Brief in Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (37 pages).
Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (38 pages).
Numerical Designation of U.S. Pat. No. 8,221,381 Claim Element or Limitation, dated Oct. 20, 2015 (4 pages).
U.S. Appl. No. 60/523,104, filed Nov. 19, 2003 by Michael O'Donovan (9 pages).
Notice of Filing Date Accorded to Petition and Time for Filing Patent Owner Preliminary Response, Case IPR 2016-00060, dated Nov. 3, 2015 (3 pages).
Resubmitted Petition for Inter Partes Review of U.S. Pat. No. 8,221,381, Inter Partes Review No. IPR 2016-00060, dated Nov. 5, 2015 (69 pages).
Declaration of Thomas R. Varner, Ph.D. in Support of Defendants' Opposition to DNA Genotek's Motion for Preliminary Injunction, *DNA Genotek, Inc. v. Spectrum DNA, Spectrum Solutions, LLC and Spectrum Packaging, LLC*, Case No. 15-661-SLR, dated Oct. 2, 2015 (31 pages).
Declaration of Melanie L. Mayer in Support of Defendants' Brief in Opposition to DNA Genotek's Motion for Preliminary Injunction, *DNA Genotek, Inc. v. Spectrum DNA, Spectrum Solutions, LLC and Spectrum Packages, LLC*, Case No. 15-661-SLR, dated Oct. 2, 2015 (256 pages).
Defendants' Reply Brief in Support of Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Oct. 16, 2015 (15 pages).
Reply Declaration of Gregg Williams in Support of Defendants' Motion to Dismiss for Lack of Personal Jurisdiction, *DNA Genotek, Inc. v. Spectrum DNA, Spectrum Solutions, LLC and Spectrum Packaging, LLC*, Case No. 15-661-SLR, dated Oct. 16, 2015 (3 pages).
Declaration of Melanie L. Mayer in Support of Defendants' Reply Brief in Support of Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Oct. 16, 2015 (15 pages).

Declaration of John M. Collins in Support of DNA Genotek's Reply in Support of the Motion for Preliminary Injunction, *DNA Genotek, Inc. v. Spectrum DNA, Spectrum Solutions, LLC and Spectrum Packaging, LLC*, Case No. 15-cv-00661-SLR, dated Nov. 5, 2015 (154 pages).
Plaintiff DNA Genotek Inc.'s Reply Brief in Support of its Motion for Preliminary Injunction, *DNA Genotek, Inc. v. Spectrum DNA, Spectrum Solutions, LLC and Spectrum Packaging, LLC*, Case No. 15-00661-SLR, dated Nov. 5, 2015 (27 pages).
Declaration of Brian M. Kramer in Support of Plaintiff DNA Genotek Inc.'s Reply Brief in Support of its Motion for Preliminary Injunction, *DNA Genotek, Inc. v. Spectrum DNA, Spectrum Solutions, LLC and Spectrum Packaging, LLC*, Case No. 15-661-SLR, dated Nov. 5, 2015 (79 pages).
Defendants' Unopposed Motion for Leave to File a Surreply in Further Opposition to Plaintiff's Motion for a Preliminary Injunction, *DNA Genotek, Inc. v. Spectrum DNA, Spectrum Solutions, LLC and Spectrum Packaging, LLC*, Case No. 15-661-SLR, dated Nov. 19, 2015 (74 pages).
Letter to Judge Sue L. Robinson of the United States District Court regarding Motion for Leave, *DNA Genotek, Inc. v. Spectrum DNA, et al.*, Case No. 15-661-SLR, dated Nov. 20, 2015 (1 page).
DNA Genotek Inc.'s Opposition to Defendants' "Unopposed" Motion for Leave to File Surreply and DNA Genotek Inc.'s Motion to Strike Unauthorized Expert Declaration, *DNA Genotek, Inc. v. Spectrum DNA, Spectrum Solutions, LLC and Spectrum Packaging, LLC*, Case No. 15-661-SLR, dated Nov. 20, 2015 (9 pages).
Declaration of Brian M. Kramer in Support of DNA Genotek Inc.'s Opposition to Defendants' "Unopposed" Motion for Leave to File Surreply and DNA Genotek Inc.'s Motion to Strike Unauthorized Expert Declarations, *DNA Genotek, Inc. v. Spectrum DNA, Spectrum Solutions, LLC and Spectrum Packaging, LLC*, Case No. 15-661-SLR, dated Nov. 20, 2015 (12 pages).
Complaint, *DNA Genotek, Inc. v. Ancestry.com DNA, LLC*, dated May 4, 2015 (62 pages).
Complaint, *DNA Genotek, Inc. v. Spectrum DNA, Spectrum Solutions, LLC and Spectrum Packaging, LLC*, dated Jul. 30, 2015 (35 pages).
Report on the Filing or Determination of an Action Regarding a Patent or Trademark for U.S. Pat. No. 8,221,381, filed May 4, 2015 (1 page).
Report on the Filing or Determination of an Action Regarding a Patent or Trademark for U.S. Pat. No. D699,310, filed Jul. 30, 2015 (1 page).
First Amended Complaint, *DNA Genotek, Inc. v. Ancestry.com DNA, LLC*, Case No. 15-0355-SLR, dated Jul. 24, 2015 (62 pages).
DNA Genotek Inc.'s Motion for Preliminary Injunction, *DNA Genotek, Inc. v. Spectrum DNA, Spectrum Solutions, LLC and Spectrum Packaging, LLC*, Case No. 15-cv-00661-SLR, dated Aug. 24, 2015 (5 pages).
Defendant's Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Aug. 10, 2015 (2 pages).
Declaration of Deforest McDuff, Ph.D., *DNA Genotek, Inc. v. Spectrum DNA, Spectrum Solutions, LLC and Spectrum Packaging, LLC*, Case No. 15-cv-00661-SLR, dated Aug. 24, 2015 (49 pages).
Ancestry DNA's Opening Brief in Support of Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Aug. 10, 2015 (18 pages).
Declaration of Ian Curry, *DNA Genotek, Inc. v. Spectrum DNA, Spectrum Solutions, LLC and Spectrum Packaging, LLC*, Case No. 15-cv-00661, dated Aug. 24, 2015 (20 pages).
Declaration of Brian M. Kramer in Support of Motion for Preliminary Injunction, *DNA Genotek, Inc. v. Spectrum DNA, Spectrum Solutions, LLC and Spectrum Packaging, LLC*, Case No. 15-cv-00661-SLR, dated Aug. 24, 2015 (40 pages).
Plaintiff DNA Genotek Inc.'s Opposition to Ancestry.com DNA, LLC's Motion to Dismiss, *DNA Genotek, Inc. v. Ancestry.com DNA, LLC*, Case No. 15-355-SLR, dated Sep. 3, 2015 (24 pages).

(56) References Cited

OTHER PUBLICATIONS

Declaration of Brian M. Kramer in Support of Plaintiff DNA Genotek Inc.'s Opposition to Ancestry.com DNA, LLC's Motion to Dismiss, *DNA Genotek, Inc. v. Ancestry.com DNA, LLC*, Case No. 15-355-SLR, dated Sep. 3, 2015 (112 pages).
Defendants' Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Sep. 4, 2015 (2 pages).
Ancestry.com DNA's Reply Brief in Support of Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Sep. 18, 2015 (15 pages).
Declaration of Melanie Mayer in Support of Ancestry.com DNA's Reply Brief in Support of Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Sep. 18, 2015 (2 pages).
Defendants' Opening Brief in Support of Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Sep. 4, 2015 (15 pages).
Declaration of Gregg Williams in Support of Defendants' Motion to Dismiss for Lack of Personal Jurisdiction, *DNA Genotek, Inc. v. Spectrum DNA, Spectrum Solutions, LLC and Spectrum Packaging, LLC*, Case No. 15-661-SLR, dated Sep. 4, 2015 (4 pages).
Plaintiff DNA Genotek Inc.'s Answering Brief in Response to Defendants' Motion to Dismiss, *DNA Genotek, Inc. v. Spectrum DNA, Spectrum Solutions, LLC and Spectrum Packaging, LLC*, Case No. 15-661-SLR, dated Sep. 30, 2015 (25 pages).
Declaration of Brian M. Kramer in Support of DNA Genotek Inc.'s Answering Brief in Response to Defendants' Motion to Dismiss, *DNA Genotek, Inc. v. Spectrum DNA, Spectrum Solutions, LLC and Spectrum Packaging, LLC*, Case No. 15-661-SLR, dated Sep. 30, 2015 (31 pages).
Declaration of Gregg Williams in Support of Defendants' Opposition to DNA Genotek's Motion for Preliminary Injunction, *DNA Genotek, Inc. v. Spectrum DNA, Spectrum Solutions, LLC and Spectrum Packaging, LLC*, Case No. 15-661-SLR, dated Oct. 2, 2015 (3 pages).
Complaint for Patent Infringement, *DNA Genotek Inc. v. Spectrum Solutions L.L.C.*, Case No. '16CV1544 MMANLS, dated Jun. 20, 2016 (9 pages).
Patent Owner's Mandatory Notices, Inter Partes Review No. IPR 2016-01152, dated Jun. 24, 2016 (6 pages).
Notice of Filing Date Accorded to Petition and Time for Filing Patent Owner Preliminary Response, Inter Partes Review No. IPR 2016-01152, dated Jun. 9, 2016 (5 pages).
Petition for Inter Partes Review of U.S. Pat. No. 8,221,381, Inter Partes Review No. IPR 2016-01152, dated Jun. 3, 2016 (86 pages).
Exhibit 1001 of Petition for Inter Partes Review of U.S. Pat. No. 8,221,381, Inter Partes Review No. IPR 2016-01152, dated Jun. 3, 2016: U.S. Pat. No. 8,221,381 (Muir et al.) (25 pages).
Exhibit 1002 of Petition for Inter Partes Review of U.S. Pat. No. 8,221,381, Inter Partes Review No. IPR 2016-01152, dated Jun. 3, 2016: File History of U.S. Pat. No. 8,221,381 (401 pages).
Joint Motion to Terminate Proceeding pursuant to 35 U.S.C § 317(A), Inter Partes Review No. IPR 2016-01152, dated Feb. 1, 2017 (5 pages).
Exhibit 1004 of Petition for Inter Partes Review of U.S. Pat. No. 8,221,381, Inter Partes Review No. IPR 2016-01152, dated Jun. 3, 2016: Curriculum Vitae of Terry N. Layton, Ph.D. (4 pages).
Exhibit 1005 of Petition for Inter Partes Review of U.S. Pat. No. 8,221,381, Inter Partes Review No. IPR 2016-01152, dated Jun. 3, 2016: Plaintiff DNA Genotek Inc.'s Opening Brief in Support of Motion for Preliminary Injunction, *DNA Genotek, Inc. v. Spectrum DNA; Spectrum Solutions L.L.C., and Spectrum Packaging, LLC*, Case No. 15-cv-00661-SLR, dated Aug. 24, 2015 (26 pages).
Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015 (15 pages).
Exhibit A of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Curriculum vitae of Juan C. Lasheras, Ph.D., filed Aug. 24, 2015 (36 pages).
Exhibit B of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: U.S. Pat. No. 8,221,381 B2, Jul. 17, 2012 (26 pages).
Exhibit C of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Spectrum Product Material Safety Data Sheet, filed Aug. 24, 2015 (11 pages).
Exhibit D of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Spectrum Product Marketing Sheet, filed Aug. 24, 2015 (2 pages).
Exhibit E of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Spectrum Product Instructions for Use, filed Aug. 24, 2015 (2 pages).
Exhibit F of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Claim chart demonstrating the limitation of Claim 1 of U.S. Pat. No. 8,221,381 in view of the Spectrum Device, filed Aug. 24, 2015 (12 pages).
Exhibit G of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: WO 2015/017701 A1, Feb. 5, 2015 (22 pages).
Exhibit H of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: File History of U.S. Appl. No. 61/861,329, filed Aug. 1, 2013 (28 pages).
Exhibit 1007 of Petition for Inter Partes Review of U.S. Pat. No. 8,221,381, Inter Partes Review No. IPR 2016-01152, dated Jun. 3, 2016: U.S. Pat. No. 7,645,424 (O'Donovan) (8 pages).
Exhibit 1008 of Petition for Inter Partes Review of U.S. Pat. No. 8,221,381, Inter Partes Review No. IPR 2016-01152, dated Jun. 3, 2016: WO-2003/104251-A2 (DNA Genotek Inc) (50 pages).
Exhibit 1009 of Petition for Inter Partes Review of U.S. Pat. No. 8,221,381, Inter Partes Review No. IPR 2016-01152, dated Jun. 3, 2016: U.S. Pat. No. 6,152,296 (Shih) (9 pages).
Exhibit 1010 of Petition for Inter Partes Review of U.S. Pat. No. 8,221,381, Inter Partes Review No. IPR 2016-01152, dated Jun. 3, 2016: WO-98-03265-A1 (Kyoritsu Chemical—check Lab., Corp) (44 pages).

(56) References Cited

OTHER PUBLICATIONS

Exhibit 1011 of Petition for Inter Partes Review of U.S. Pat. No. 8,221,381, Inter Partes Review No. IPR 2016-01152, dated Jun. 3, 2016: (Certified English Translation) WO-98/03265-A1 (Kyoritsu Chemical—check Lab., Corp) (30 pages).
Exhibit 1012 of Petition for Inter Partes Review of U.S. Pat. No. 8,221,381, Inter Partes Review No. IPR 2016-01152, dated Jun. 3, 2016: DE-199 50 884-A1 (Wella Ag) (16 pages).
Exhibit 1013 of Petition for Inter Partes Review of U.S. Pat. No. 8,221,381, Inter Partes Review No. IPR 2016-01152, dated Jun. 3, 2016: (Certified English Translation) DE-199 50 884-A1 (Wella Ag) (8 pages).
Exhibit 1014 of Petition for Inter Partes Review of U.S. Pat. No. 8,221,381, Inter Partes Review No. IPR 2016-01152, dated Jun. 3, 2016: U.S. Pat. No. 6,228,323 (Asgharian et al.) (23 pages).
Exhibit 1015 of Petition for Inter Partes Review of U.S. Pat. No. 8,221,381, Inter Partes Review No. IPR 2016-01152, dated Jun. 3, 2016: The American Heritage Dictionary of the English Language, Fourth Edition (2000) (definitions of: "corner"; "fastener"; "inert"; "pointed"; "reservoir"; "vial") (8 pages).
Exhibit 1016 of Petition for Inter Partes Review of U.S. Pat. No. 8,221,381, Inter Partes Review No. IPR 2016-01152, dated Jun. 3, 2016: Defendants' Brief in Opposition to DNA Genotek's Motion of Preliminary Injunction, *DNA Genotek, Inc. v. Spectrum DNA: Spectrum Solutions L.L.C., and Spectrum Packaging, LLC*, Case No. 15-cv-00661-SLR, dated Oct. 2, 2015 (37 pages).
Exhibit 1017 of Petition for Inter Partes Review of U.S. Pat. No. 8,221,381, Inter Partes Review No. IPR 2016-01152, dated Jun. 3, 2016: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (38 pages).
Exhibit 1018 of Petition for Inter Partes Review of U.S. Pat. No. 8,221,381, Inter Partes Review No. IPR 2016-01152, dated Jun. 3, 2016: U.S. Appl. No. 60/523,104, filed Nov. 19, 2003 by Michael O'Donovan (9 pages).
Exhibit 1019 of Petition for Inter Partes Review of U.S. Pat. No. 8,221,381, Inter Partes Review No. IPR 2016-01152, dated Jun. 3, 2016: Numerical Designation of U.S. Pat. No. 8,221,381 Claim Element or Limitation (4 pages).
Exhibit 1020 of Petition for Inter Partes Review of U.S. Pat. No. 8,221,381, Inter Partes Review No. IPR 2016-01152, dated Jun. 3, 2016: U.S. Pre-Grant publication No. 2003/0089627 A1 ("Chelles") (8 pages).
Exhibit 1021 of Petition for Inter Partes Review of U.S. Pat. No. 8,221,381, Inter Partes Review No. IPR 2016-01152, dated June 3, 2016: PCT publication No. WO-2005/023667 A1 ("Clarkson") (36 pages).
Exhibit 1022 of Petition for Inter Partes Review of U.S. Pat. No. 8,221,381, Inter Partes Review No. IPR 2016-01152, dated Jun. 3, 2016: Proof of Service, Case No. 1:15-cv-00355-SLR, United States District Court for the District of Delaware, dated Jun. 4, 2015 (2 pages).
Exhibit 1023 of Petition for Inter Partes Review of U.S. Pat. No. 8,221,381, Inter Partes Review No. IPR 2016-01152, dated Jun. 3, 2016: Pending claims, U.S. Appl. No. 12/338,873 ("Birnboim '873 application") (4 pages).
Exhibit 1024 of Petition for Inter Partes Review of U.S. Pat. No. 8,221,381, Inter Partes Review No. IPR 2016-01152, dated Jun. 3, 2016: Abstract of title, U.S. Appl. No. 12/338,873 ("Birnboim '873 application"), dated Jun. 1, 2016 (1 page).
Exhibit 1025 of Petition for Inter Partes Review of U.S. Pat. No. 8,221,381, Inter Partes Review No. IPR 2016-01152, dated Jun. 3, 2016: Deposition of John Collins, Ph.D., *DNA Genotek, Inc. v. Spectrum DNA; Spectrum Solutions L.L.C., and Spectrum Packaging, LLC*, Case No. 15-cv-00661-SLR, dated Nov. 13, 2015 (3 pages).
Petition for Inter Partes Review of U.S. Pat. No. 9,207,164, Inter Partes Review No. IPR 2016-01467, dated Jul. 20, 2016 (83 pages).

Exhibit 1001 of Petition for Inter Partes Review of U.S. Pat. No. 9,207,164, Inter Partes Review No. IPR 2016-01467, dated Jul. 20, 2016: U.S. Pat. No. 9,207,164 (Muir et al.) (32 pages).
Exhibit 1002 of Petition for Inter Partes Review of U.S. Pat. No. 9,207,164, Inter Partes Review No. IPR 2016-01467, dated Jul. 20, 2016: File History of U.S. Pat. No. 9,207,164 (545 pages).
Exhibit 1003 of Petition for Inter Partes Review of U.S. Pat. No. 9,207,164, Inter Partes Review No. IPR 2016-01467, dated Jul. 20, 2016: Declaration of Terry N. Layton, Ph.D. (100 pages).
Exhibit 1004 of Petition for Inter Partes Review of U.S. Pat. No. 9,207,164, Inter Partes Review No. IPR 2016-01467, dated Jul. 20, 2016: Curriculum Vitae of Terry N. Layton, Ph.D. (4 pages).
Exhibit 1005 of Petition for Inter Partes Review of U.S. Pat. No. 9,207,164, Inter Partes Review No. IPR 2016-01467, dated Jul. 20, 2016: Plaintiff DNA Genotek Inc.'s Opening Brief in Support of Motion for Preliminary Injunction, *DNA Genotek, Inc. v. Spectrum DNA; Spectrum Solutions L.L.C., and Spectrum Packaging, LLC*, Case No. 15-cv-00661-SLR, dated Aug. 24, 2015 (26 pages).
Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015 (15 pages).
Exhibit A of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Curriculum vitae of Juan C. Lasheras, Ph.D., filed Aug. 24, 2015 (36 pages).
Exhibit B of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: U.S. Pat. No. 8,221,381 B2, Jul. 17, 2012 (26 pages).
Exhibit C of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-0061-SLR, dated Aug. 24, 2015: Spectrum Product Material Safety Data Sheet, filed Aug. 24, 2015 (11 pages).
Exhibit D of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging LC*, Case No. 15-cv-0061-SLR, dated Aug. 24, 2015: Spectrum Product Marketing Sheet, filed Aug. 24, 2015 (2 pages).
Exhibit E of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Spectrum Product Instructions for Use, filed Aug. 24, 2015 (2 pages).
Exhibit F of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Claim chart demonstrating the limitation of Claim 1 of U.S. Pat. No. 8,221,381 in view of the Spectrum Device, filed Aug. 24, 2015 (12 pages).
Exhibit G of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: WO 2015/017701 A1, Feb. 5, 2015 (22 pages).
Exhibit H of Exhibit 1006 of Petition for Inter Partes Review of U.S. Pat. No. 9,207,164, Inter Partes Review No. IPR 2016-01467, dated

(56) References Cited

OTHER PUBLICATIONS

Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: File History of U.S. Appl. No. 61/861,329, filed Aug. 1, 2013 (28 pages).
Exhibit 1007 of Petition for Inter Partes Review of U.S. Pat. No. 9,207,164, Inter Partes Review No. IPR 2016-01467, dated Jul. 20, 2016: U.S. Pat. No. 7,645,424 (O'Donovan) (8 pages).
Exhibit 1008 of Petition for Inter Partes Review of U.S. Pat. No. 9,207,164, Inter Partes Review No. IPR 2016-01467, dated Jul. 20, 2016: WO-2003/104251-A2 (DNA Genotek Inc) (50 pages).
Exhibit 1009 of Petition for Inter Partes Review of U.S. Pat. No. 9,207,164, Inter Partes Review No. IPR 2016-01467, dated Jul. 20, 2016: U.S. Pat. No. 6,152,296 (Shih) (9 pages).
Exhibit 1010 of Petition for Inter Partes Review of U.S. Pat. No. 9,207,164, Inter Partes Review No. IPR 2016-01467, dated Jul. 20, 2016: WO-98/03265 A1 (Kyoritsu Chemical—check Lab., Corp) (44 pages).
Exhibit 1011 of Petition for Inter Partes Review of U.S. Pat. No. 9,207,164, Inter Partes Review No. IPR 2016-01467, dated Jul. 20, 2016: (Certified English Translation) WO-98/03265 A1 (Kyoritsu Chemical—check Lab., Corp) (30 pages).
Exhibit 1012 of Petition for Inter Partes Review of U.S. Pat. No. 9,207,164, Inter Partes Review No. IPR 2016-01467, dated Jul. 20, 2016: DE-199 50 884-A1 (Wella Ag) (16 pages).
Exhibit 1013 of Petition for Inter Partes Review of U.S. Pat. No. 9,207,164, Inter Partes Review No. IPR 2016-01467, dated Jul. 20, 2016: (Certified English Translation) DE-199 50 884-A1 (Wella Ag) (8 pages).
Exhibit 1014 of Petition for Inter Partes Review of U.S. Pat. No. 9,207,164, Inter Partes Review No. IPR 2016-01467, dated Jul. 20, 2016: U.S. Pat. No. 6,228,323 (Asgharian et al.) (23 pages).
Exhibit 1015 of Petition for Inter Partes Review of U.S. Pat. No. 9,207,164, Inter Partes Review No. IPR 2016-01467, dated Jul. 20, 2016: The American Heritage Dictionary of the English Language, Fourth Edition (2000) (definitions of: "corner"; "fastener"; "inert"; "reservoir"; "vial") (8 pages).
Exhibit 1016 of Petition for Inter Partes Review of U.S. Pat. No. 9,207,164, Inter Partes Review No. IPR 2016-01467, dated Jul. 20, 2016: Defendants' Brief in Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (37 pages).
Exhibit 1017 of Petition for Inter Partes Review of U.S. Pat. No. 9,207,164, Inter Partes Review No. IPR 2016-01467, dated Jul. 20, 2016: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (38 pages).
Exhibit 1018 of Petition for Inter Partes Review of U.S. Pat. No. 9,207,164, Inter Partes Review No. IPR 2016-01467, dated Jul. 20, 2016: U.S. Appl. No. 60/523,104, filed Nov. 19, 2003 by Michael O'Donovan (9 pages).
Exhibit 1019 of Petition for Inter Partes Review of U.S. Pat. No. 9,207,164, Inter Partes Review No. IPR 2016-01467, dated Jul. 20, 2016: Numerical Designation of U.S. Pat. No. 8,221,381 Claim Element or Limitation (4 pages).
Exhibit 1020 of Petition for Inter Partes Review of U.S. Pat. No. 9,207,164, Inter Partes Review No. IPR 2016-01467, dated Jul. 20, 2016: U.S. Pre-Grant publication No. 2003/0089627 A1 ("Chelles") (8 pages).
Exhibit 1021 of Petition for Inter Partes Review of U.S. Pat. No. 9,207,164, Inter Partes Review No. IPR 2016-01467, dated Jul. 20, 2016: PCT publication No. WO-2005/023667 A1 ("Clarkson") (36 pages).
Exhibit 1022 of Petition for Inter Partes Review of U.S. Pat. No. 9,207,164, Inter Partes Review No. IPR 2016-01467, dated Jul. 20, 2015: Proof of Service, case 1:15-cv-00355-SLR, United States District Court for the District of Delaware, dated Jun. 4, 2016 (2 pages).
Exhibit 1023 of Petition for Inter Partes Review of U.S. Pat. No. 9,207,164, Inter Partes Review No. IPR 2016-01467, dated Jul. 20, 2016: Pending claims, U.S. Appl. No. 12/338,873 ("Birnboim '873 application") (4 pages).
Exhibit 1024 of Petition for Inter Partes Review of U.S. Pat. No. 9,207,164, Inter Partes Review No. IPR 2016-01467, dated Jul. 20, 2016: Abstract of title, U.S. Appl. No. 12/338,873 ("Birnboim '873 application"), dated Jun. 1, 2016 (1 page).
Exhibit 1025 of Petition for Inter Partes Review of U.S. Pat. No. 9,207,164, Inter Partes Review No. IPR 2016-01467, dated Jul. 20, 2016: Deposition of John Collins, Ph.D., *DNA Genotek, Inc. v. Spectrum DNA; Spectrum Solutions L.L.C., and Spectrum Packaging, LLC*, Case No. 15-cv-00661-SLR, dated Nov. 13, 2015 (3 pages).
Exhibit 1026 of Petition for Inter Partes Review of U.S. Pat. No. 9,207,164, Inter Partes Review No. IPR 2016-01467, dated Jul. 20, 2016: U.S. Pat. No. 8,221,381 (Muir et al.) (25 pages).
Exhibit 1027 of Petition for Inter Partes Review of U.S. Pat. No. 9,207,164, Inter Partes Review No. IPR 2016-01467, dated Jul. 20, 2016: File History of U.S. Pat. No. 8,221,381 (401 pages).
Exhibit 1028 of Petition for Inter Partes Review of U.S. Pat. No. 9,207,164, Inter Partes Review No. IPR 2016-01467, dated Jul. 20, 2016: Affidavit of Service on Spectrum Solutions, LLC for Summons and Complaint, case 3:16-cv-01544-JLS-NLS, United States District Court for the Southern District of California, dated Jun. 21, 2016 (2 pages).
Exhibit 1029 of Petition for Inter Partes Review of U.S. Pat. No. 9,207,164, Inter Partes Review No. IPR 2016-01467, dated Jul. 20, 2016: Affidavit of Service on Spectrum DNA R/A for Summons and Complaint, case 3:16-cv-01544-JLS-NLS, United States District Court for the Southern District of California, dated Jun. 21, 2016 (2 pages).
Exhibit 1030 of Petition for Inter Partes Review of U.S. Pat. No. 9,207,164, Inter Partes Review No. IPR 2016-01467, dated Jul. 20, 2016: Comparison of U.S. Pat. No. 9,207,164 and U.S. Pat. No. 8,221,381 Claim Elements or Limitations (12 pages).
Exhibit 1031 of Petition for Inter Partes Review of U.S. Pat. No. 9,207,164, Inter Partes Review No. IPR 2016-01467, dated Jul. 20, 2016: Redacted Memorandum of Points and Authorities in Support of Motion for Preliminary Injunction, *DNA Genotek Inc. v. Spectrum Solutions L.L.C., and Spectrum DNA*, Case No. 3:16-cv-01544-JLS-NLS (USDC—S.D. Cal.) (31 pages).
Exhibit 1032 of Petition for Inter Partes Review of U.S. Pat. No. 9,207,164, Inter Partes Review No. IPR 2016-01467, dated Jul. 20, 2016: Redacted Declaration of Juan C. Lasheras, Ph.D. in Support of Motion for Preliminary Injunction, *DNA Genotek Inc. v. Spectrum Solutions L.L.C., and Spectrum DNA*, Case No. 3:16-cv-01544-JLS-NLS (USDC—S.D. Cal.) (27 pages).
Patent Owner's Mandatory Notices, Inter Partes Review No. IPR 2016-01467, dated Aug. 12, 2016 (6 pages).
Notice of Filing Date Accorded to Petition and Time for Filing Patent Owner Preliminary Response, Inter Partes Review No. IPR 2016-01467, dated Aug. 17, 2016 (5 pages).
Patent Owner's Preliminary Response, Inter Partes Review No. IPR 2016-00060, dated Feb. 3, 2016 (51 pages).
Exhibit 2001 of Patent Owner's Preliminary Response, Inter Partes Review No. IPR 2016-00060, dated Feb. 3, 2016: Screenshot from the PTO's "Patent Application Information Retrieval" for U.S. Pat. No. 6,152,296.
Exhibit 2002 of Patent Owner's Preliminary Response, Inter Partes Review No. IPR 2016-00060, dated Feb. 3, 2016.
Exhibit 2003 of Patent Owner's Preliminary Response, Inter Partes Review No. IPR 2016-00060, dated Feb. 3, 2016: Changes to Implement Miscellaneous Post Patent Provisions of the Leahy-Smith American Invents Act, 1421 Off. Gaz. Pat. & Trademark Office 1263, dated Dec. 29, 2015 (39 pages).
Patent Owner's Response, Inter Partes Review No. IPR 2016-00060, dated Jun. 22, 2016 (28 pages).

(56) References Cited

OTHER PUBLICATIONS

Exhibit 2004 of Patent Owner's Response, Inter Partes Review No. IPR 2016-00060, dated Jun. 22, 2016: Transcript of Deposition of Terry Layton, Ph.D., dated May 25, 2016 (172 pages).
Exhibit 2005 of Patent Owner's Response, Inter Partes Review No. IPR 2016-00060, dated Jun. 22, 2016: Declaration of John Collins, Ph.D., dated Jun. 22, 2016 (18 pages).
Exhibit 2006 of Patent Owner's Response, Inter Partes Review No. IPR 2016-00060, dated Jun. 22, 2016: John M. Collins, Ph.D. Resume (4 pages).
Exhibit 2007 of Patent Owner's Response, Inter Partes Review No. IPR 2016-00060, dated Jun. 22, 2016: Petition for Inter Partes Review of U.S. Pat. No. 8,221,381, filed Jun. 3, 2016 (86 pages).
Exhibit 2008 of Patent Owner's Response, Inter Partes Review No. IPR 2016-00060, dated Jun. 22, 2016: Declaration of Terry Layton, Ph.D. in Support of Petition for Inter Partes Review of U.S. Pat. No. 8,221,381, filed Jun. 3, 2016 (96 pages).
Exhibit 2009 of Patent Owner's Response, Inter Partes Review No. IPR 2016-00060, dated Jun. 22, 2016: U.S. Pat. No. 4,131,016, Dec. 26, 1978 (5 pages).
Exhibit 2010 of Patent Owner's Response, Inter Partes Review No. IPR 2016-00060, dated Jun. 22, 2016: U.S. Pat. No. 4,301,812, dated Nov. 24, 1981 (7 pages).
Exhibit 2011 of Patent Owner's Response, Inter Partes Review No. IPR 2016-00060, dated Jun. 22, 2016: ASTM D 1894-01, "Standard Test Method for Static and Kinetic Coefficients of Friction of Plastic Film and Sheeting," (6 pages).
Petitioner Ancestry.com DNA, LLC's Reply to Patent Owner's Response, Inter Partes Review No. IPR 2016-00060, dated Sep. 6, 2016 (40 pages).
Exhibit 1020 of Petitioner Ancestry.com DNA, LLC's Reply to Patent Owner's Response, Inter Partes Review No. IPR 2016-00060, dated Sep. 6, 2016: Declaration of Michael J. Sacksteder in Support of Petitioner's Motion for Pro Hac Vice Admission of Michael J. Sacksteder Pursuant to 37 C.F.R. § 42.10(c), Feb. 2, 2016 (5 pages).
Exhibit 1021 of Petitioner Ancestry.com DNA, LLC's Reply to Patent Owner's Response, Inter Partes Review No. IPR 2016-00060, dated Sep. 6, 2016: Declaration of Melanie L. Mayer in Support of Petitioner's Motion for Pro Hac Vice Admission of Melanie L. Mayer Pursuant to 37 C.F.R. § 42.10(c), dated Sep. 20, 2016 (5 pages).
Exhibit 1022 of Petitioner Ancestry.com DNA, LLC's Reply to Patent Owner's Response, Inter Partes Review No. IPR 2016-00060, dated Sep. 6, 2016: Resubmitted Petition for Inter Partes Review for U.S. Pat. No. 8,221,381, dated Nov. 5, 2015 (69 pages).
Exhibit 1023 of Petitioner Ancestry.com DNA, LLC's Reply to Patent Owner's Response, Inter Partes Review No. IPR 2016-00060, dated Sep. 6, 2016: Institution Decision from the Patent Trial and Appeal Board, dated Apr. 8, 2016 (23 pages).
Exhibit 1024 of Petitioner Ancestry.com DNA, LLC's Reply to Patent Owner's Response, Inter Partes Review No. IPR 2016-00060, dated Sep. 6, 2016: Deposition of John M. Collins, Ph.D., dated Aug. 24, 2016 (99 pages).
Exhibit 1025 of Petitioner Ancestry.com DNA, LLC's Reply to Patent Owner's Response, Inter Partes Review No. IPR 2016-00060, dated Sep. 6, 2016: Excerpt from the Deposition of John Collins, Ph.D., Nov. 13, 2015, *DNA Genotek Inc.* v. *Spectrum DNA, et al.*, USDC—D. Del. Case No. 15-CV-00661, dated Nov. 13, 2015 (5 pages).
Exhibit 1026 of Petitioner Ancestry.com DNA, LLC's Reply to Patent Owner's Response, Inter Partes Review No. IPR 2016-00060, dated Sep. 6, 2016: Declaration of John M. Collins, Ph.D. in Support of Plaintiff's Reply in Support of Motion for Preliminary Injunction, *DNA Genotek Inc.* v. *Spectrum Solutions L.L.C., et al.*, USDC—S.D. Cal. Case No. 16-CV-01544, filed Aug. 19, 2016 (65 pages).

Exhibit 1027 of Petitioner Ancestry.com DNA, LLC's Reply to Patent Owner's Response, Inter Partes Review No. IPR 2016-00060, dated Sep. 6, 2016: Biomek® FX User's Manual, dated May 2000 (5 pages).
Petitioner's Notice of Deposition of John M. Collins, Ph.D., Inter Partes Review No. IPR 2016-00060, dated Aug. 2, 2016 (3 pages).
Patent Owner's Motion for Pro Hac Vice Admission of John R. Lanham under 37 C.F.R. § 42.10(c), Inter Partes Review No. IPR 2016-00060, dated Aug. 11, 2016 (7 pages).
Exhibit 2012 of Patent Owner's Motion for Pro Hac Vice Admission of John R. Lanham under 37 C.F.R. § 42.10(c), Inter Partes Review No. IPR 2016-00060, dated Aug. 11, 2016: Declaration of John R. Lanham in Support of Motion for Pro Hac Vice Admission of John R. Lanham under 37 C.F.R. § 42.10(c), dated Aug. 11, 2016 (4 pages).
Petitioner Ancestry.com DNA, LLC's Updated Exhibit List, Inter Partes Review No. IPR 2016-00060, dated Sep. 6, 2016 (5 pages).
Petitioner Ancestry.com DNA, LLC's Request for Oral Argument Pursuant to 37 C.F.R. § 42.70(a), Inter Partes Review No. IPR 2016-00060, dated Sep. 20, 2016 (4 pages).
Patent Owner's Request for Oral Argument, Inter Partes Review No. IPR 2016-00060, dated Oct. 26, 2016 (4 pages).
Petitioner's Mandatory Change-of-Information Notices under 37 C.F.R. § 42.8(a)(3), Inter Partes Review No. IPR 2016-00060, dated Dec. 5, 2016 (6 pages).
Decision Granting Motion for Pro Hac Vice Admission of Melanie L. Mayer 37 C.F.R. § 42.10, Inter Partes Review No. IPR 2016-00060, dated Feb. 25, 2016 (3 pages).
Decision Granting Motion for Pro Hac Vice Admission of Michael J. Stacksteder 37 C.F.R. § 42.10, Inter Partes Review No. IPR 2016-00060, dated Feb. 25, 2016 (3 pages).
Decision to Institute Inter Partes Review, Inter Partes Review No. IPR 2016-00060, dated Apr. 8, 2016 (23 pages).
Scheduling Order, Inter Partes Review No. IPR 2016-00060, dated Apr. 8, 2016 (7 pages).
Deposition Notice of Terry N. Layton, Ph.D., Inter Partes Review No. IPR 2016-00060, dated May 11, 2016 (3 pages).
Patent Owner's Updated Mandatory Notices, Inter Partes Review No. IPR 2016-00060, dated Jun. 23, 2016 (5 pages).
Request for Oral Hearing 37 C.F.R. § 42.70, Inter Partes Review No. IPR 2016-00060, dated Nov. 2, 2016 (4 pages).
Patent Owner's Preliminary Response, Inter Partes Review No. IPR 2016-01467, dated Nov. 17, 2016 (53 pages).
Exhibit 2001 of Patent Owner's Preliminary Response, Inter Partes Review No. IPR 2016-01467, dated Nov. 17, 2016: Resubmitted Petition, IPR2016-00060, Paper 5, dated Oct. 20, 2015 (69 pages).
Exhibit 2002 of Patent Owner's Preliminary Response, Inter Partes Review No. IPR 2016-01467, dated Nov. 17, 2016: Decision to Institute Inter Partes Review, IPR2016-00060, Paper 19 (23 pages).
Exhibit 2003 of Patent Owner's Preliminary Response, Inter Partes Review No. IPR 2016-01467, dated Nov. 17, 2016: Transcript of Deposition of Terry Layton, IPR2016-00060, Exhibit 2004, May 25, 2016 (172 pages).
Exhibit 2004 of Patent Owner's Preliminary Response, Inter Partes Review No. IPR 2016-01467, dated Nov. 17, 2016: Declaration of John M. Collins, IPR2016-00060, Exhibit 2005, dated Jun. 22, 2016 (18 pages).
Exhibit 2005 of Patent Owner's Preliminary Response, Inter Partes Review No. IPR 2016-01467, dated Nov. 17, 2016: Declaration of Terry Layton, IPR2016-01152, Exhibit 1003, dated Jun. 3, 2016 (96 pages).
Exhibit 2006 of Patent Owner's Preliminary Response, Inter Partes Review No. IPR 2016-01467, dated Nov. 17, 2016: Defendant's Responsive Claim Construction Brief, *DNA Genotek, Inc.* v. *Ancestry. com DNA, LLC*, Case No. 15-00355-SLR (D. Del.), dated Oct. 21, 2016 (36 pages).
Exhibit 2007 of Patent Owner's Preliminary Response, Inter Partes Review No. IPR 2016-01467, dated Nov. 17, 2016: Declaration of John M. Collins, Ph.D. in Support of Plaintiff's Reply in Support of Motion for Preliminary Injunction, *DNA Genotek, Inc.* v. *Spectrum Solutions L.L.C.; and Spectrum DNA*, Case No. 16-cv-01544-JLS-NLS (S.D. Cal.), dated Aug. 19, 2016 (65 pages).

(56) References Cited

OTHER PUBLICATIONS

Petitioner Ancestry.com DNA, LLC's Motion for Pro Hac Vice Admission of Michael J. Sacksteder pursuant to 37 C.F.R. § 42.10(c), IPR2016-01467, dated Sep. 20, 2016 (7 pages).
Exhibit 1033 of Petitioner Ancestry.com DNA, LLC's Motion for Pro Hac Vice Admission of Michael J. Sacksteder pursuant to 37 C.F.R. § 42.10(c), IPR2016-01467, dated Sep. 20, 2016: Declaration of Michael J. Sacksteder in Support of Petitioner Ancestry.com DNA, LLC's Motion for Pro Hac Vice Admission of Michael J. Sacksteder pursuant to 37 C.F.R. § 42.10(c), dated Sep. 20, 2016 (5 pages).
Petitioner Ancestry.com DNA, LLC's Motion for Pro Hac Vice Admission of Melanie L. Mayer pursuant to 37 C.F.R. § 42.10(c), IPR2016-01467, dated Sep. 20, 2016 (7 pages).
Exhibit 1034 of Petitioner Ancestry.com DNA, LLC's Motion for Pro Hac Vice Admission of Melanie L. Mayer pursuant to 37 C.F.R. § 42.10(c), IPR2016-01467, dated Sep. 20, 2016: Declaration of Melanie L. Mayer in Support of Petitioner Ancestry.com DNA, LLC's Motion for Pro Hac Vice Admission of Melanie L. Mayer pursuant to 37 C.F.R. § 42.10(c), dated Sep. 20, 2016 (5 pages).
Patent Owner's Preliminary Response, Inter Partes Review No. IPR 2016-01152, dated Sep. 9, 2016 (50 pages).
Exhibit 2001 of Patent Owner's Preliminary Response, Inter Partes Review No. IPR 2016-01152, dated Sep. 9, 2016: Resubmitted Petition for Inter Partes Review of U.S. Pat. No. 8,221,381, dated Nov. 5, 2015 (69 pages).
Exhibit 2002 of Patent Owner's Preliminary Response, Inter Partes Review No. IPR 2016-01152, dated Sep. 9, 2016: Petition for Inter Partes Review of U.S. Pat. No. 6,974,569 under 35 U.S.C. §§ 311-319 and 37 C.F.R. §§ 42.1-.80, 42.100-.123, dated Aug. 14, 2013 (64 pages).
Exhibit 2003 of Patent Owner's Preliminary Response, Inter Partes Review No. IPR 2016-01152, dated Sep. 9, 2016: Petition for Inter Partes Review of U.S. Pat. No. 6,974,569 under 35 U.S.C. §§ 311-319 and 37 C.F.R. §§ 42.1-.80, 42.100-.123, dated Mar. 12, 2014 (62 pages).
Petitioner Ancestry.com DNA, LLC's Motion for Pro Hac Vice Admission of Michael J. Sacksteder pursuant to 37 C.F.R. § 42.10(c), dated Sep. 20, 2016 (7 pages).
Exhibit 1026 of Petitioner Ancestry.com DNA, LLC's Motion for Pro Hac Vice Admission of Michael J. Sacksteder pursuant to 37 C.F.R. § 42.10(c), dated Sep. 20, 2016: Declaration of Michael J. Sacksteder in Support of Petitioner's Motion for Pro Hac Vice Admission of Michael J. Sacksteder pursuant to 37 C.F.R. § 42.10(c), Sep. 20, 2016 (4 pages).
Petitioner Ancestry.com DNA, LLC's Motion for Pro Hac Vice Admission of Melanie L. Mayer pursuant to 37 C.F.R. § 42.10(c), dated Sep. 20, 2016 (7 pages).
Exhibit 1027 of Petitioner Ancestry.com DNA, LLC's Motion for Pro Hac Vice Admission of Melanie L. Mayer pursuant to 37 C.F.R. § 42.10(c), dated Sep. 20, 2016: Declaration of Melanie L. Mayer in Support of Petitioner's Motion for Pro Hac Vice Admission of Melanie L. Mayer pursuant to 37 C.F.R. § 42.10(c), Sep. 20, 2016 (4 pages).
Order Granting Motion for Pro Hac Vice Admission of Melanie L. Mayer 37 C.F.R. § 42.10, dated Sep. 28, 2016 (3 pages).
Order Granting Motion for Pro Hac Vice Admission of Michael J. Sacksteder 37 C.F.R. § 42.10, dated Sep. 28, 2016 (3 pages).
Decision Denying Institution of Inter Partes Review 37 C.F.R. § 42.108, dated Nov. 23, 2016 (13 pages).
Exhibit 2001 of Patent Response, Inter Partes Review No. IPR 2016-00060 , dated Jun. 22, 2016: Screenshot from the PTO's "Patent Application Information Retrieval" for U.S. Pat. No. 6,152,296.
Exhibit 2002 of Patent Owner's Response, Inter Partes Review No. IPR 2016-00060 , dated Jun. 22, 2016.
Exhibit 2003 of Patent Owner's Response, Inter Partes Review No. IPR 2016-00060 , dated Jun. 22, 2016: Changes to Implement Miscellaneous Post Patent Provisions of the Leahy-Smith American Invents Act, 1421 Off. Gaz. Pat. & Trademark Office 1263, dated Dec. 29, 2015 (39 pages).

Record of Oral Hearing, Inter Partes Review No. IPR 2016-00060, dated Jan. 12, 2017 (54 pages).
Joint Motion to Terminate Proceeding pursuant to 35 U.S.C § 317(A), Inter Partes Review No. IPR 2016-00060, dated Feb. 1, 2017 (5 pages).
Joint Request that the Settlement Agreement Filed Separately as Exhibit 2013 be Treated as Business Confidential Information and be Kept Separate from the Files, Inter Partes Review No. IPR 2016-00060, dated Feb. 1, 2017 (4 pages).
Bardon et al. (1980) "Properties of Purified Salivary Ribonuclease, and Salivary Ribonuclease Levels in Children with Cystic Fibrosis and in Heterozygous Carriers," Clinica Chimica Acta. 101:17-24.
Bardon et al. (1984) "Salivary Ribonuclease in Cyclic Fibrosis and Control Subjects," Acta Paediatr. Scand. 73:263-266.
Blumberg (1987) "Creating a ribonuclease-free environment," Methods Enzymol. 152:20-24.
Chu et al. (2004) "Initial viral load and the outcomes of SARS," CMAJ. 171(11):1349-1352.
Donnelly et al. (2003) "Epidemiological determinants of spread of causal agent of severe acute respiratory syndrome in Hong Kong," The Lancet. 361:1761-1766.
Ehrenfeld et al. (1981) "Stability of Poliovirus RNA in Cell-free Translation Systems Utilizing Two Initiation Sites," The Journal of Biological Chemistry. 256(6):2656-2661.
Eichel et al. (1964) "Acid and Alkaline Ribonucleases of Human Parotid, Submaxillary, and Whole Saliva," Archives of Biochemistry and Biophysics. 107:197-208.
Zamboni et al. (2008) "Total RNA extraction from strawberry tree (*Arbutus unedo*) and several other woody-plants," iForest. 1:122-125.
Google Web Page Date of Feb. 1, 2001, downloaded Aug. 25, 2015, https://www.google.com/search?q=sds+tris+edta&rls=com.microsofr/03Aen-USo/03AIE-Address&source=Int&tbs=cdr%3AI%2Ccdmin%3AI%2FI%2F1900%2Ccd_max%3A10%2F6%2F2005&tbm=, "Preparing protein samples for sds-page", No Author, No Journal, No Volume, No Issue number, 2 page printout.
Grustein (Jun. 8, 2005) "Grunstein Lab Biological Chemistry, Western Membrane Stripping," UCLA. http://www/biolchem.ucla.edu/grunstein/Western%20Membrane%Stripping.html. 1 page.
Guinn (1966) "Extraction of Nucleic Acids from Lyphilized Plant Material," Plant Physiology. 41:689-695.
Guy (2002) "Evaluation of Events Occurring at Mucosal Surfaces: Techniques Used to Collect and Analyze Mucosal Secretions and Cells," Clinical and Diagnostic Laboratory Immunology. 9(4):753-762.
He et al. (2004) "Development of a Western Blot Assay for Detection of Antibodies against Coronavirus Causing Severe Acute Respiratory Syndrome," Clinical and Diagnostic Laboratory Immunology. 11(2):417-422.
<<http://www.ars.usda.gov/SP2UserFiles/Place/30400510/protocols/WesternBlot.pdf, "Method Used to Extract Total Muscle Protein for Western Blot Using TRIS-EDTA Buffer", Published by USDA, Beltsville, MD., Submitted by Wheeler and Ekeren, published Feb. 1, 2001, 13 pages.
<<http://www.einsten.net/pdf/1350246084.pdf, "Chem 405 Biochemistry Lab I", published by the University of Texas, Austin, TX, Feb. 1, 2001, downloaded Feb. 22, 2015, Author unknown, No journal, No volume, No issue, 9 pages.
<<http://www.google.com/patents/DE10219117CI?cl=en, downloaded Feb. 22, 2015, no author provided, no journal, no issue, no volume, By Google, Inc., Mountain View, California, 4 pages.
<<https://www.google.com/search?q=method+used+to+extract+total+muscle+protein+for+western+blot+using+tris-edta+buffer&rls=com.microsofr/o3Aen-US° /03A1E-Address&tbas=0&biw=1615&bih=845&source=Int&tbs=cdr)/03AI,)/02Ccd_mi n%3AI%2FI')/02F1900')/02Ccd_max')/03A10%2 F6%2 F2005&tbm=, Nov. 17, 2015., Robert Kelly, 2 pages.
Juusola et al. (2003) "Messenter RNA profiling: a prototype method to supplant conventional methods for body fluid identification," Forensic Science International. 135:85-96.
Kay et al. (1952) "An Improved Preparation of Sodium desoxyribonucleate," Journal of the American Chemical Society. 74(7): 1724-1726.

(56) References Cited

OTHER PUBLICATIONS

Lee et al. (2006) "Analysis of gene expression profiles of normal human nasal mucosa and nasal polyp tissues by SAGE," J. Allergy Clin. Immunol. 118:134-142.
Li et al. (2004) "RNA Profiling of Cell-free Saliva Using Microarray Technology," J. Dent. Res. 83(3): 199-203.
Lindgren et al. (2004) "Noradrenaline represses PPAR (peroxisomeproliferator-activated receptor) g2 gene expression in brown adipocytes: intracellular signalling and effects on PPARg2 and PPARgl protein levels," Biochem. J. 382:597-605.
Macrae (2007) "Extraction of Plant RNA," Methods in Molecular Biology. 353:15-24.
Moser et al. (2004) "Isolation of Functional RNA From Small Amounts of Different Grape and Applie Tissues," Molecular Biotechnology. 26:95-99.
No Author, Google date search, performed May 5, 2016, https://www.google.com/search7q . . . , Google, San Francisco, CA, 2.
Okuno et al. (1979) "RNA Polymerase Activity and Protein Synthesis in Brome Mosaic Virus-Infected Protoplasts," Virology. 99:218-225.
Park et al. (2006) "Characterization of RNA in Saliva," Clinical Chemistry. 52(6): 1-7.
Peiris et al. (2003) "Clinical progression and viral load in a community outbreak of coronavirus-associated SARS pneumonia: a prospective study," The Lancet 361:1767-1772.
Qiagen (2006) "Qiagen Sample Preparation Systems Offer Guaranteed Freedom of Operation," http://wwwl.qiagen.com/Products/SamplePrepSystems.aspx.
Riddell et al. (2001) "Investigation of Optimal Specimen Type and Sampling Time for Detection of Measles Virus RNA during a Measles Epidemic," Journal of Clinical Microbiology. 39(1):375-376.
Rohan et al. (2000) "Optimization of the Week-Cel Collection Method for Quantitation of Cytokines in Mucosal Secretions," Clinical and Diagnostic Laboratory Immunology. 7(1):45-48.
Roy et al. (1999) "The effect of saliva specimen collection, handling and storage protocols on hepatitis C virus (HCV) RNA detection by PCR," Oral Diseases. 5:123-127.
Thai et al. (2004) "Development and Evaluation of a Novel Loop-Mediated Isothermal Amplification Method for Rapid Detection of Severe Acute Respiratory Syndrome Coronavirus," Journal of Clinical Microbiology. 42(5):1956-1961.
Van Binnendijk et al. (2003) "Evaluation of Serological and Virological Tests in the Diagnosis of Clinical and Subclinical Measles Virus Infections during an Outbreak of Measles in the Netherlands," The Journal of Infectious Diseases. 188:898-903.
Verwoerd et al. (1989) "A small-scale procedure for the rapid isolation of plant RNAs," Nucleic Acids Res. 17(6):2362.
Vitale (2001) "The Total RNA Story," Agilent Technologies. Publication No. 5988-2281EN. www.agilent.com/chem, 2 pages.
Wong et al. (2006) "Salivary diagnostics powered by nanotechnologies, proteomics and genomics," J. Am. Dent. Assoc. 137:313-321.
World Health Organization (2003) "A multicentre collaboration to investigate the cause of severe acute respiratory syndrome," The Lancet. 361:1730-1733.
World Health Organization (2006) "Collecting, preserving and shipping specimens for the diagnosis of avian influenza A(H5N1) virus infection, Guide for field operations," Document No. WHO/CDS/EPR/ARO/2006.1, Annex 8, 4 pages.
Yam et al. (2003) "Evaluation of Reverse Transcription—PCR Assays for Rapid Diagnosis of Severe Acute Respiratory Syndrome Associated with a Novel Coronavirus," Journal of Clinical Microbiology. 41(10):4521-4524.
Yamkovaya et al. (2006) "Isolation of Total RNA from Baker's Yeast," Applied Biochemistry and Microbiology. 42(1):84-88.
"Report of an Expert Consultation on the Uses of Nucleic Acid Amplification Tests for the Diagnosis of Tuberculosis," Centers for Disease Control and Prevention, 7 pages.

Shamputa, I.C., L. Rigouts, F. Portaels (2004) "Molecular genetic methods for diagnosis and antibiotic resistance detection of mycobacterial from clinical specimens,", APMIS 112: 728-752.
Desjardin, L.E., M.D. Perkins, K. Wolski, S. Haun, L. Teixeira, Y. Chen, J.L. Johnson, J.J. Ellner, R. Dietze, J. Bates, M.D. Cave, K.D. Eisenach (1999) "Measurement of sputum *Mycobacterium tuberculosis* messenger RNA as a surrogate for response to chemotherapy" Am J Respir Crit Care Med 160: 203-210.
Greenwood, N.N. and Earnshaw, A., Chemistry of the Elements, 2nd Edition, Butterworth Heinemann, Oxford, Chapter 17, pp. 789-887 (1998).
Afkhami, A. T. Madrakian, A.R. Zarei, Spectrophotometric determination of periodate, iodate and bromate mixtures based on their reaction with iodide, Analytical Sciences (2001) 17: 1199-1202.
Wroblewski D, Hannett GE, Bopp DJ, Dumyati GK, Haise TA, Dumas NB, Musser KS (2009) Rapid molecular characterization of Clostridium difficile and assessment of populations of C. difficile in stool specimens. J Clin Microbiol 47(7): 2142-2148.
Halse TA, Escuyer VE, Musser KA (2011) Evaluation of a Single-Tube Multiplex Real-time PCR for the Differentiation of Members of the *Mycobacterium tuberculosis* Complex in Clinical Specimens. J Clin Microbiol 49(7): 2562-2567.
Halse TA, Edwards J, Cunningham PL, Wolfgang WJ, Dumas NB, Escuyer VE, Musser KA (2010) Combined real-time PCR and rpoB gene pyrosequencing for rapid identification of *Mycobacterium tuberculosis* and determination of rifampin resistance directly in clinical specimens. J Clin Microbiol 48:1182-1188.
Corbett EL, Watt C J, Walker N, Maher D, Williams BG, Raviglione MC, Dye C (2003) The growing burden of tuberculosis: global trends and interactions with the HIV epidemic. Arch Intern Med 163:1009-1021.
Diagnostic Standards and Classification of Tuberculosis in Adults and Children; American Thoracic Society and the Centers for Disease Control and Prevention (2000) Am J Respir Crit Care Med 161:1376-1395.
Hobby GL, Holman AP, Iseman MD, Jones J (1973) Enumeration of tubercle bacilli in sputum of patients with pulmonary tuberculosis. Antimicrob Agents Chemother 4:94-104.
Yeager HJ Jr, Lacy J, Smith L, LeMaistre C (1967) Quantitative studies of mycobacterial populations in sputum and saliva. Am Rev Respir Dis 95:998-1004.
Gandhi et al. (2006) Extensively drug-resistant tuberculosis as a cause of death in patients co-infected with tuberculosis and HIV in a rural area of South Africa, Lancet; 368: 1575-80.
Gandhi NR, Moll A, Pawinski R, et al. (Aug. 2006) High prevalence and mortality from extensively-drug resistant (XDR) TB in TB/HIV coinfected patients in rural South Africa. Toronto, Canada: Late Breaker Session, XVI International AIDS Conference, 13-18 [Abstract THLB0210]—published in IAPAC Monthly, vol. 12, No. 9, Sep. 2006, 3 pages.
Raviglione M (2006) XDR-TB: entering the post-antibiotic era? Int J Tuberc Lung Dis 10(11):1185-1187.
Davis JL, Huang L, Kovacs JA, Masur H, Murray P, Havlir DV, Worodria WO, Charlebois ED, Srikantiah P, Cattamanchi A, Huber C, Shea YR, Chow Y, Fischer SH (2009) Polymerase chain reaction of secA1 on sputum or oral wash samples for the diagnosis of pulmonary tuberculosis. Clinical Infectious Diseases 48: 725-732.
Yassen G, Noori J, Yas NS (2012) Detection of acid fast bacilli in the saliva of patients having pulmonary tuberculosis. J Bagh College Dentistry 24(3): 59-62.
Anonymous (2009) Updated guidelines for the use of nucleic acid amplification tests in the diagnosis of tuberculosis. MMWR Morb Mortal Wkly Rep 58: 7-10.
Scott II RD (2009) The Direct Medical Costs of Healthcare-associated Infections in U.S. Hospitals and the Benefits of Prevention. Centers for Disease Control and Prevention, 16 pages.
Fawley WN, Wilcox MH (2001) Molecular epidemiology of endemic Clostridium difficile infection. Epidemiology and Infection 126(3):343-350. ISSN 0950-2688.
Martinez, J.A., Ruthazer, R., Hansjosten, K., Barefoot, L., and Snydman, D.R. (Sep. 2003). "Role of environmental contamination as a risk factor for acquisition of vancomycin-resistant enterococci

(56) References Cited

OTHER PUBLICATIONS in patients treated in a medical intensive care unit." Archives of Internal Medicine vol. 163(16):1905-12.
K. Burton, M.R. Lunt, G.B. Petersen, J.C. Siebke, Studies of Nucleotide Sequences in Deoxyribonucleic Acid, Cold Spring Harbor Symposium on Quantitative Biology, vol. 28, pp. 27-34 (1963).
G. Schmidt and S.J. Thannhauser (1945) A method for the determination of deoxyribonucleic acid, ribonucleic acid, and phosphoproteins in animal tissues. Journal of Biological Chemistry vol. 161, pp. 83-89.
G. M. Richards, Modifications of the diphenylamine reaction giving increased sensitivity and simplicity in the estimation of DNA. Analyt. Biochem. 57, 369-376 (1974).
J.M. Kissane, E. Robins, The fluorometric measurement of deoxyribonucleic acid in animal tissues with special reference to the central nervous system. J. Biol. Chem. 233, 184-188 (1958).
"Report of Expert Consultations on Rapid Molecular Testing to Detect Drug-Resistant Tuberculosis in the United States," Centers for Disease Control and Prevention, 26 pages.
J. A. Morello and P. D. Ellner (1969) New medium for blood cultures. Appl. Microbiol. 17:68-07.
B.M. Chassy. A gentle method for the lysis of oral streptococci. Biochem Biophys Res Commun 68: 603-608 (1976).
Kaser et al. (2009) Optimized Method for Preparation of DNA from Pathogenic and Environmental Mycobacteria, Applied and Environmental Microbiology, vol. 75, No. 2, p. 414-418.
M. Silberberg, Chemistry, The Molecular Nature of Matter and Change, Mosby-Year Book Inc., USA, Chapter 2, pp. 73-75 (1996).
K. Randerath et al., Sequence analysis of nonradioactive RNA fragments by periodate-phosphatase digestion and chemical tritium labeling: characterization of large oligonucleotides and oligonucleotides containing modified nucleoside, Nucleic Acids Res, Sep. 1, 1974, pp. 1121-1142.
Lehmann U et al: "Real-Time PCR Analysis of DNA and RNA Extracted from Formalin-Fixed and Paraffin-Embedded Biopsies", Methods, Academic Press, US, vol. 25, No. 4, Jan. 1, 2001 (Jan. 1, 2001), pp. 409-418, XP003017515, ISSN: 1046-2023, DOI: 10.1006/METH.2001.1263.
De Mey M et al: "Comparison of DNA and RNA quantification methods suitable for parameter estimation in metabolic modeling of microorganisms", Analytical Biochemistry, Elsevier, Amsterdam, NL, vol. 353, No. 2, Jun. 15, 2006 (Jun. 15, 2006), pp. 198-203, XP024942171, ISSN: 0003-2697, DOI:10.1016/J.AB.2006.02.014.
Joshi Vinay G et al: "Rapid label-free visual assay for the detection and quantification of viral RNA using peptide nucleic acid (PNA) and gold nanoparticles (AuNPs)", Analytica Chimica Acta, vol. 795, pp. 1-7, XP028698983, ISSN: 0003-2670, DOI: 10.1016/J.ACA.2013.06.037.
S. Gallagher, "Quantitation of Nucleic Acids with Absorption Spectroscopy", Sep. 1, 1998 (Sep. 1, 1998), XP055419161, Retrieved from the Internet: URL:http://onlinelibrary.wiley.com/store/10.1002/0471140864.psa04ks13/asset/psa04k.pdf?V=1&t=j973wht9&s=3da536c696b35b2d0d87b89e6d20ae1133cc 4279 [retrieved on Oct. 25, 2017], 3 pages.
Philippe Desjardins et al: "Nano Drop Microvolume Quantitation of Nucleic Acids", Journal of Visualized Experiments, No. 1, Nov. 22, 2010 (Nov. 22, 2010), XP055419163, DOI: 10.3791 /2565, 4 pages.
Phoenix Research Products: "Western Offices: Quantification of Nucleic Acids using Absorbance Introduction", Dec. 1, 2003 (Dec. 1, 2003), XP055419166, Retrieved from the Internet: URL:https://www.phenixresearch.com/Images/TN_Quantificati7on.pdf [retrieved on Oct. 25, 2017], 4 pages.
Ruzin (1999) Plant Microthechnique and Microscopy (Year; 1999), 6 pages.
Cole SR, Young GP, Esterman A, Cadd B, Morcom J (2003) A randomised trial of the impact of new faecal haemoglobin test technologies on population participation in screening for colorectal cancer. Journal of Medical Screening 10:117-122.
DiGiulio DB, Romero R, Amogan HP, Kusanovic JP, Bik EM, Gotsch F, Kim CJ, Erez O, Edvin S, Reiman DA (2008) Microbial prevalence, diversity and abundance in amniotic fluid during preterm labor: a molecular and culture-based investigation. PloS One 3(8):e3056, 10 pages.
Heaton KW, Radvan J, Cripps H, Mountford RA, Braddon FEM, Huges AO (1992) Defecation frequency and timing, and stool form in the general population: a prospective study. Gut 33(6):818-24.
Korecka A, Arulampalam V (Feb. 2012) The gut microbiome: scourge, sentinel or spectator? Journal of Oral Microbiology 4: 1-14.
Lewis SJ, Heaton KW (1997) Stool form scale as a useful guide to intestinal transit time. Scandinavian Journal of Gastroenterology 32: 920-924.
Palmer C, Bik EM, DiGiulio DB, Reiman DA, Brown PO (2007) Development of the human infant intestinal microbiota. PLoS Biology 5(7): e177, 18 pages.
Weyant et al. 1990 Effect of ionic and nonionic detergents on the Taq polymerase. Biotechniques. Sep. 1990;9(3):308-9.
Rossen, L. et al. Inhibition of PCR by components of food samples, microbial diagnostic assays and DNA-extraction solutions. International Journal of Food Microbiology, 17 (1992) 37-45.
Parkes, Helen C., Saunders, Ginny C. (Editors) Analytical Molecular Biology: Quality and Validation. Royal Society of Chemistry (1999) Chapter 6 Inhibitors and Enhancers of PCR; pp. 81-102.
Rusconi et al. in "Quantification of Sodium Dodecyl Sulfate in Microliter-Volume Biochemical Samples by Visible Light Spectroscopy." Analytical Biochemistry. 2001. 295, 31-37.
Boom, R. et al. Rapid and Simple Method for Purification of Nucleic Acids, J. Clin. Microbiol. 1990, 28(3):495, 10 pages.
Caldas, C., et al. Detection of K-ras Mutations in the Stool of Patients with Pancreatic Adenocarcinoma and Pancreatic Ductal Hyperplasia, Cancer Res 1994;54:3568-3573.
Van Der Hoek, L. et al. Isolation of Human Immunodeficiency Virus Type 1 (HIV-1) RNA from Feces by a Simple Method and Difference between HIV-1 Subpopulations in Feces and Serum Journal of Clinical Microbiology, Mar. 1995, p. 581-588.
Van Der Giessen, J.W.B. et al., Amplification of 16S rRNA sequences to detect *Mycobacterium paratuberculosis* J. Med. Microbiol vol. 36 (1992) pp. 255-263.
Deuter, R. et al. A method for preparation of fecal DNA suitable for PCR Nucleic Acids Research, 1995, vol. 23, No. 18, 3800-3801.
Holland, J.L. et al. PCR Detection of *Escherichia coli* 0157:H7 Directly from Stools J. Clin. Microbiol. 2000, 38(11):4108.
Lokitonov, A. et al. Quantitation of DNA from exfoliated colonocytes isolated from human stool surface as a novel noninvasive screening test for colorectal cancer Clin Cancer Res 1998;4:337-342.
Machiels et al. New Protocol for DNA Extraction of Stool Bio Techniques 28:286-290 (Feb. 2000).
McOrist, A.L. et al. A comparison of five methods for extraction of bacterial DNA from human faecal samples Journal of Microbiological Methods 50 (2002) 131-139.
Palladino, S. et al. Rapid Detection of vanA and vanB genes Directly from Clinical Specimens and Enrichment Broths by Real-Time Multiplex PCR Assay J. Clin. Microbiol. 2003, 41(6):2483. DOI: 10.1128/JCM.41.6.2483-2486.2003.
Sidransky, D. et al. Identification of ras oncogene mutations in the stool of patients with curable colorectal tumors Science 256.n5053 (Apr. 3, 1992): pp. 102(4).
Olson, J. et al. DNA Stabilization Is Critical for Maximizing Performance of Fecal DNA-Based Colorectal Cancer Tests Diagn Mol Pathol, vol. 14, No. 3, Sep. 2005, 9 pages.
Brusa, T. et al. Oxygen Tolerance of Anaerobic Bacteria Isolated from Human Feces Current Microbiology vol. 19 (1989), pp. 39-43.
Wu, G.D., et al. Linking Long-Term Dietary Patterns with Gut Microbial Enterotypes Science vol. 334, 105 (2011); DOI: 10.1126/science.1208344, 4 pages.
Walker, A.W. et al. Dominant and diet-responsive groups of bacteria within the human colonic microbiota The ISME Journal (2011) 5, 220-230.
Smith, B. et al. Optimising Bacterial DNA Extraction from Faecal Samples: Comparison of Three Methods The Open Microbiology Journal, 2011, 5, 14-17.
Sillen, L.G. et al. Stability Constants of Metal-Ion Complexes vol. 42, No. 9, Sep. 1965 521,1 page.

(56) References Cited

OTHER PUBLICATIONS

Parsonett, J. et al. Helicobacter Pylori Infection and the Risk of Gastric Carcinoma N Engl J Med 1991;325:1127-31.
O'Sullivan, D.J. Methods for Analysis of the Intestinal Microflora Curr. Issues Intest. Microbiol. (2000) 1(2): 39-50.
Moore, W.E.C. et al. Intestinal Floras of Populations That Have a High Risk of Colon Cancer Applied and Environmental Microbiology, Sep. 1995, p. 3202-3207.
Cutting, M. et al. Manual of Procedures for Human Microbiome Project Core Microbiome Sampling Protocol A HMP Protocol #07-001 Version No. 12.0 Jul. 29, 2010, 114 pages.
Ley et al. Crystal ball—2007 Environmental Microbiology (2007) 9(1), 1-11 doi: 10.1111/j.1462-2920.2006.01222.x.
Lee, Y.K. et al. Has the Microbiota Played a Critical Role in the Evolution of the Adaptive Immune system? Science 330, 1768 (2010); DOI: 10.1126/science.1195568.
Kinross, J.M. et al. Gut microbiome-host interactions in health and disease Genome Medicine 2011, 3:14 http://genomemedicine.com/content/3/3/14, 12 pages.
Grenham, S. et al. Brain-gut-microbe communication in health and disease Frontiers in Physiology Dec. 2011 vol. 2, Article 94, 15 pages.
Bahl, M.l. et al. Freezing fecal samples prior to DNA extraction affects the Firmicutes to Bacteroidetes ratio determined by downstream quantitative PCR analysis FEMS Microbiol Lett 329 (Mar. 2012) 193-197 DOI: 10.1111/j.1574-6968.2012.02523.x.
Aries, V. et al. Bacteria and the aetiology of cancer of the large bowel Gut, 1969, 10, 334-335.
Ariefdjohan, M.W. et al. Comparison of DNA extraction kits for PCR-DGGE analysis of human intestinal microbial communities from fecal specimens Nutrition Journal 2010, 9:23 http://www.nutritionj.com/content/9/1/23, 8 pages.
Apajalahti, J.H.A. et al. Selective Plating Underestimates Abundance and Shows Differential Recovery of Bifidobacterial Species for Human Feces Appl. Environ. Microbiol. 2003, 69(9):5731. DOI: 10.1128/AEM.69.9.5731-5735.2003, 5 pages.
Wang Yun-xiang et al., Biochemistry. Huazhong: University of Science & Technology Press, 2011, 4 pages.
Dong Weixian, Analytical Chemistry Lecture Part and Learning Instructions (II). Beijing: Open University Press, 1963, 4 pages.
Xu, Yan-die, Application of Coordination Chemistry in Industry. Higher Education Press, 1989, 5 pages.
Yan, Xuan-Shen et al., Ionic Equilibrium and Chemical Reactions in Aqueous Solutions. Higher Education Press, 1993, 5 pages.
E.E Daniel et al, vol. 43, "On the mechanicnisms whereby EDTA. EGTA. DTPA. OXALATE. Desferrioxamine, and 1,10-phenanthroline affect contractility of rat uterus" Canadian Journal of Physiology and Pharmacology vol. 43, (1965) pp. 111-136.
Hervas-Aguila, Evidence for the Direct Involvement of the Proteasome in the Proteolytic Processing of the Aspergillus nidulans Zinc Finger Transcription Factor PacC*iSI, JBC, 282(48):34735-34747 (2007).
Setlow, J. Mechanisms which contribute to the long-term survival of spores of *Bacillus* species, App. Bacteriol. Symp. Suppl., 76:49S-60S (1994).
Burdz TV, Wolfe J, Kabani A (2003) Evaluation of sputum decontamination methods for *Mycobacterium tuberculosis* using viable colony counts and flow cytometry. Diagn Microbiol Infect Dis 47: 503-509.
Dorman SC, Bussoli MA, Ritz SA (2010) Alcohol fixation of induced sputum samples for applications in rural communities. Can Respir J 17(3): 115-121.
Efthimiadis A, Jayaram L, Weston S, Carruthers, S, Hargreave FE (2002) Induced sputum: Time from expectoration to processing. Eur Respir J 19: 706-708.
Gopinath K and Singh S (2009) Multiplex PCR assay for simultaneous detection and differentiation of *Mycobacterium tuberculosis*, *Mycobacterium avium* complexes and other Mycobacterial species directly from clinical specimens. J Appl Microbiol 107: 425-435.
Hammerschlag MR, Harding L, Macone A, Smith AL, Godlmann DA (1980) Bacteriology of sputum in cystic fibrosis: Evaluation of dithiothreitol as a mucolytic agent. J Clin Microbiol 11(6):552-557.
Holz O, Mücke M, Zarza P, Loppow D, Jörres RA, Magnussen H (2001) Freezing of homogenized sputum samples for intermittent storage. Clin Exp Allergy 31: 1328-1331.
Kelly MM, Hargreave FE, Cox GE (2003) A method to preserve sputum for delayed examination. Eur Respir J 22: 996-1000.
Lipsky BA, Gates J, Tenover FC, Plorde JJ (1984) Factors affecting clinical value of microscopy for acid-fast bacilli. Rev Infect Dis 6: 214-222.
US Centers for Disease Control and Prevention (CDC, 2009) Updated guidelines for the use of nucleic acid amplification tests in the diagnosis of tuberculosis. MMWR Morb Mortal Wkly Rep 58: 7-10.
Morris S, Bai GH, Suffys P, Portillo-Gomez L, Fairchok M, Rouse D (1995) Molecular mechanisms of multidrug resistance in clinical isolates of *Mycobacterium tuberculosis*. J Infect Dis 171: 954-960.
Park H, Jang H, Kim C, Chung B, Chang CL, Park SK, Song S (2000) Detection and identification of mycobacteria by amplification of the internal transcribed spacer regions with genus and species-specific PCR primers. J Clin Microbiol 38: 4080-4085.
Parmasivan CN, Narayana AS, Prabhakar R, Rajagopal MS, Somasundaram PR, Tripathy SP (1983) Effect of storage of sputum specimens at room temperature on smear and culture results. Tubercle 64(2): 119-124.
Popov TA, Petlichkovski A, Mustakov TB, DuBushe LM, Popova DN (2004) Assessment of a protocol for sputum freezing and subsequent examination. J Allergy Clin Immunol 113: S193.
Selvam JM, Wares F, Perumal M, Gopi PG, Sudha G, Chandrasekaran V, Santha T (2007) Health-seeking behaviour of new smear-positive TB patients under a DOTS programme in Tamil Nadu, India. Int J Tuberc Lung Dis 11: 161-167.
Telenti A, Marchesi F, Balz M, Bally F, Bottger EC, Bodmer T (1993) Rapid identification of mycobacteria to the species level by polymerase chain reaction and enzyme analysis. J Clin Microbiol 31: 175-178.
Thornton CG, MacLellan KM, Brink TL JR, Lockwood DE, Romagnoli M, Turner J, Merz WG, Schwalbe RS, Moody M, Lue Y, Passen S (1998) Novel method for processing respiratory specimens for detection of mycobacteria by using C18-carboxypropylbetaine: Blinded study. J Clin Microbiol 36(7): 1996-2003.
Wilson ML (1996) General principles of specimen collection and transport. Clin Inf Dis 22: 766-777.
WHO. 2001. Global tuberculosis control. WHO/CDS/TB/2001 287:18-19.
PT Kent and GP Kubica (1985) Public Health Microbiology, a Guide for the Level III Laboratory, Centers for Disease Control, Division of Laboratory Training and Consultation. Atlanta, GA, US Department of Health and Human Services, US Government Printing Office, 226 pages.
Krasnow I, Wayne LG (1966) Sputum digestion. I The mortality rate of tubercle bacilli in various digestion systems. Am J Clin Pathol 45: 352-355.
Silverstolpe, L (1948) Förbättrad metod för påvisande av tuberkelbakterier. Nord Med 48: 2220-2222.
Carricajo et al., J. Clin. Microbiol., 39(10):3799-3800 (2001) (Year: 2001).
DNA Genotek's Blog, [online] Published on Oct. 17, 2011. Retrieved Jul. 5, 2018 from URL: http://blog.dnagenotek.com/topic/dna-identification (Cited reference and identification thereof obtained from the Notice of References in U.S. Appl. No. 29/574,966, dated Sep. 7, 2018, 7 pages.
<http://www.abcam.com/primary-antibodies/new-resources-guide-for-imaging-reagents, accessed on Oct. 8, 2019, 24 pages.
<https://www.aidsmap.com/Accuracy/page/13233952#ref1323397, Jun. 2019, 4 pages.
<http://www.aidsmap.com/Large-US-study-shows-which-HIV-tests-are-most-accurate/page/2812847/, Jan. 2014, 2 pages.
<https://www.aidsmap.com/Saliva/page/1322841/, Jul. 2019, 3 pages.
<http://www.catie.ca/en/pif/spring-2014/hiv-home-based-testing-potential-benefits-and-ongoing-concerns, 2014, 3 pages.
<https://www.cdc.gov/hiv/testing/clinical/, Apr. 22, 2019, 4 pages.

(56) References Cited

OTHER PUBLICATIONS

<https//www.genome.gov/10000206, Fluorescence In Situ Hybridization Fact Sheet, accessed on Oct. 9, 2019, 2 pages.
<https://www.cdc.gov/hiv/pdf/testing/hiv-tests-advantages-disadvantages_1.pdf, accessed on Oct. 8, 2019, 7 pages.
<http://www.gsk.com/en-gb/media/press-releases/2014/gsk-data-presented-at-ers-demonstrate-potential-of-blood-eosinophil-levels-to-help-inform-copd-treatment-decisions/, Sep. 8, 2014, 7 pages.
<http://www.lungcancerprofiles.com, accessed on Oct. 8, 2019, 2 pages.
<http://www.mycancergenome.org/content/disease/lung-cancer/egfr/, 2010-2017, 8 pages.
<https://pharmaintelligence.informa.com/products-and-services/data-and-analysis/datamonitor-healthcare, 2019, 3 pages.
<http://www.pm360online.com/liquid-biopsy-consistent-with-tumor-biopsy-for-nsclc/, by Jennifer Kelly Shepphird, Feb. 26, 2015, 2 pages.
<https://www.questdiagnostics.com/home/physicians/testing-services/specialists/hospitals-lab-staff/specimen-handling/immunohistochemistry.html, 2000-2019, 8 pages.
<http://www.uptodate.com/contents/anaplastic-lymphoma-kinase-alk-fusion-oncogene-positive-non-small-cell-lung-cancer, 2019, 10 pages.
Anonymous: "Paraformaldehyde Fixation of Cells", BUMC-Flow Cytometry Core Facility, downloaded from http://www.bu.edu/flow-cytometry/files/2010/10/Paraformaldehyde-Fixation-of-cells.doc, Mar. 7, 2007, pp. 1-4.
"Living Hinge" from Wikipedia, the free encyclopedia, last edited on Sep. 14, 2021, 3 pages.
OralStat Device; Quick Reference Guide; American Bio Medica Corporation 2008 (Kinderhook, New York); http://abmc.com/products/documents/QRG_OralStat.pdf, 1 page.
Roche Diagnostics GmbH, "LightCycler Control Kit DNA," Version 3 (2003) (26 pages).
Roche Molecular Biochemicals PCR Applications Manual, 3rd Edition. Roche Diagnostics, (2006) (340 pages).
Simport Products, Tubes, Caps and Vials (http://wwv.simport.com/products/tubes-caps-and-vials/tubes/t501.html) Copyright 2009-2011, 2 pages.
Abdolmaleky, H. M. et al., "Genetics and Epigenetics in Major Psychiatric Disorders," Am J Pharmacogenomics, 5(3):149-160 (2005).
Ausubel, F. M. et al., "Purification and Concentration of DNA from Aqueous Solutions," Short Protocols in Molecular Biology, 5th ed. John Wiley & Sons, 2-6 (2002).
Balamane, M. et al., "Detection of HIV-1 in Saliva: Implications for Case-Identification, Clinical Monitoring and Surveillance for Drug Resistance," The Open Virology Journal, 4:88-93 (2010).
Baron, S. et al., "Why Is HIV Rarely Transmitted by Oral Secretions?" Arch Intern Med., 159:303-310 (1999).
Birnboim, H. C., "New method for extraction of ribonucleic acid and polyribosomes from Schizosachharomyces pombe," J Bacteriol., 107(3):659-63 (1971).
Birnboim, H. C. et al., "Effect of Lipophilic Chelators on Oxyradical-Induced DNA Strand Breaks in Human Granulocytes: Paradoxical Effect of 1,1 O-Phenanthroline," Archives of Biochemistry and Biophysics, 294(1):17-21 (1992).
Birnboim, H. C., "Extraction of High Molecular Weight RNA and DNA from Cultured Mammalian Cells," Methods in Enzymology, 216:154-160 (1992).
Birnboim, H. C. & Doly, J., "A rapid alkaline extraction procedure for screening recombinant plasmid DNA," Nucleic Acids Research, 7(6): 1513-1524 (1979).
Birnboim, H. C. & Jevcak, J. J., "Fluorometric Method for Rapid Detection of DNA Strand Breaks in Human White Blood Cells Produced by Low Doses of Radiation," Cancer Research, 41:1889-1892 (1981).
Bonne, N. J. & Wong, D. T. W., "Salivary biomarker development using genomic, proteomic and metabolomic approaches," Genome Medicine, 4:82 (2012), 12 pages; http://genomemedicine.com/content/4/5/82.
"Box with Living Hinge"; efunda, Living Hinge; copyright 2012, 3 pages.
Bryant, K. L. et al., "KRAS: feeding pancreatic cancer proliferation," Trends in Biochemical Sciences, 39(2):91-100 (2014).
Buckingham, L., Molecular Diagnostics Fundamentals, Methods and Clinical Applications, Second Edition, Chapter?, Nucleic Acid Amplification, F. A. Davis Company, 2012, 40 pages.
Burdge, G. C. & Lillycrop, K. A., "Nutrition, Epigenetics, and Developmental Plasticity: Implications for Understanding Human Disease," Annu. Rev. Nutr., 30:315-339 (2010), and Fig. 1, 1 page.
Buettner, G. R., "Ascorbate autoxidation in the presence of iron and copper chelates," Free Radic Res Commun., 1(6):349-53 (1986).
Buettner, G. R. & Jurkiewicz, B. A., "Catalytic metals, ascorbate and free radicals: combinations to avoid," Radiat Res., 145(5):532-41 (1996).
Buettner, G. R., "Ascorbate oxidation: UV absorbance of ascorbate and ESR spectroscopy of the ascorbyl radical as assays for iron," Free Radic Res Commun., 10:5-9 (1990).
Buettner, G. R., "In the absence of catalytic metals ascorbate does not autoxidize at pH 7: ascorbate as a test for catalytic metals," J Biochem Biophys Methods., 16(1):27-40 (1988).
Casado, B. et al., "Advances in proteomic techniques for biomarker discovery in COPD," Expert Rev. Clin. Immunol, 7(1):111-123 (2011).
Canadian Industrial Design Certificate of Registration, Registration No. 127470 dated Jun. 21, 2010, 3 pages.
Canadian Industrial Design Certificate of Registration, Registration No. 132896 dated Jun. 21, 2010, 28 pages.
Canadian Industrial Design Certificate of Registration, Registration No. 132897 dated Jun. 21, 2010, 28 pages.
Casado et al., "Advances in Proteomic Techniques for Biomarker Discovery in COPD," Expert Rev Clin Immunol. 2011; 7(1):111-123, 15 pages.
Chouliaras, L. et al., "Epigenetic regulation in the pathophysiology of Alzheimer's disease," Progress in Neurobiology, 90(4):498-510 (2010).
Clarke, E. T. & Martell, A. E., "Stabilities of the alkaline earth and divalent transition metal complexes of the tetraazamacrocyclic tetraacetic acid ligands," Inorganic Chimica Acta, 190:27-36 (1991).
Costa, E. et al., "Epigenetic Downregulation of GABAergic Function in Schizophrenia: Potential for Pharmacological Intervention?" Mol Interv., 3(4):220-229 (2003).
Croxson, M. C. & Bellamy, A. R., "Extraction of rotavirus from human feces by treatment with lithium dodecyl sulfate," Appl Environ Microbiol., 41 (1):255-60 (1981).
Dako Danemark A/S 2013. IHC Guidebook, Sixth Edition, Immunohistochemical Staining Methods, 2013, 218 pages.
Dawson, R. M. C. et al., "Stability constants of metal complexes," Data for Biochemical Research, Third Edition. Oxford Publications, 399-407 (1989).
Dictionary entry for "Lid", p. 1615; The Compact Edition of the Oxford English Dictionary, vol. 1, A-O, Oxford University Press 1971 (printed in the USA) (Twenty-second printing in US, Jun. 1982) (Oxford, New York, etc.).
Di Stefano, A. et al., "Association of increased CCL5 and CXCL7 chemokine expression with neutrophil activation in severe stable COPD," Thorax, 64:968-975 (2009).
Dos-Santos, M. C. et al., "Cell phenotyping in saliva of individuals under psychological stress," Cellular Immunology, 260:39-43 (2009).
Eaves, L. et al., "Resolving multiple epigenetic pathways to adolescent depression," Journal of Child Psychology and Psychiatry, 44(7):1006-1014 (2003).
European Community Design Application No. 001095186-0001 dated Feb. 20, 2009, 3 pages.
European Community Design Application No. 001095186-0002 dated Feb. 20, 2009, 4 pages.
European Community Design Application No. 001095186-0003 dated Feb. 20, 2009, 4 pages.

(56) References Cited

OTHER PUBLICATIONS

Even-Desrumeaux, K. et al., "State of the Art in Tumor Antigen and Biomarker Discovery," Cancers, 3:2554-2596 (2011).
Faner, R. et al., "Lessons from ECLIPSE: a review of COPD biomarkers," Thorax, 69:666-672 (2014).
Feng, W., "Identification of Human Lung Cancer Stem Cell Markers," 2010 Research Grant program Winning Abstract, 2 pages.
French, D. J. et al., "Ultra-Rapid DNA Analysis Using HyBeacon™ Probes and Direct PR Amplification from Saliva," Molecular and Cellular Probes, 16:319-326 (2002).
Gaester, K. et al., "Human papillomavirus infection in oral fluids of HIV-1-positive men: prevalence and risk factors," Scientific Reports, 4:6592 (2014), 5 pages; doi:10.1038/srep06592.
George, L. & Brightling, C. E., "Eosinophilic airway inflammation: role in asthma and chronic obstructive pulmonary disease," Ther Adv Chronic Dis, 7(1): 34-51 (2016).
Gernez, Y. et al., "Neutrophils in chronic inflammatory airway diseases: can we target them and how?" Eur Respir J, 35:467-469 (2010).
Garcia-Closas, M. et al., "Collection of Genomic DNA from Adults in Epidemiological Studies by Buccal Cytobrush and Mouthwash," Cancer Epidemiology, Biomarkers & Prevention, 10:687-696 (2001).
Goldenberger, D. et al., "Simple 'universal' DNA extraction procedure compatible with direct PCR amplification," Experientia, 52:295 (1996) (Abstract Only).
Grant, D. D. et al., "Elimination of non-viable 6-thioguanine-sensitive T cells from viable T cells prior to PCR analysis," J Immunol Methods., 225(1-2):61-66 (1999).
Heath, E. M. et al., "Use of Buccal Cells Collected in Mouthwash as a Source of DNA for Clinical Testing," Arch. Pathol. Lab. Med., 125:127-133 (2001).
Hemmes, M. et al., Abstract: "Specimen Collection Within the Cancer Research Network: A Critical Appraisal," Clin Med Res., 8(3-4): 191, 1 page.
Hiraide, M. et al., "Speciation of Iron in River Water," Analytical Sciences, 4:605-609 (1988).
Ho, S.-M., "Environmental epigenetics of asthma: An update," J Allergy Clin Immunol, 126(3):453-465 (2010).
International Search Report dated Feb. 26, 2013 for International Application No. PCT/US2012/043176.
Partial European Search Report for EP Application No. EP 16199880, dated Feb. 1, 2017.
Iwamoto, K. & Kato, T., "Epigenetic Profiling in Schizophrenia and Major Mental Disorders," Neuropsychobiology, 60:5-11 (2009).
Javaid, M. A. et al., "Saliva as a diagnostic tool for oral and systemic diseases," Journal of Oral Biology and Craniofacial Research, 6:67-75 (2016).
Johnson, L. J. & Tricker, P. J., "Epigenomic plasticity within populations: its evolutionary significance and potential," Heredity, 105:113-121 (2010).
Kappeler, L. & Meaney, M. J., "Epigenetics and parental effects," Bioessays, 32:818-827 (2010).
Kerr, K. M. et al., "Second ESMO consensus conference on lung cancer: pathology and molecular biomarkers for non-small-cell lung cancer," Annals of Oncology, 25:1681-1690 (2014).
Kilpatrick, C. W., "Noncryogenic preservation of mammalian tissues for DNA extraction: an assessment of storage methods," Biochem Genet., 40(1-2):53-62 (2002).
Korpanty, G. J. et al., "Biomarkers that currently affect clinical practice in lung cancer: EGFR, ALK, MET, ROS-1, and KRAS," Frontiers in Oncology, 4:204 (2014), 8 pages; doi:10.3389/fonc.2014.00204.
Koutsokera, A. et al., "Pulmonary biomarkers in COPD exacerbations: a systematic review," Respiratory Research, 14:111 (2013), 12 pages; http://respiratory-research.com/content/14/1/111.
Kuratomi, G. et al., "Aberrant DNA methylation associated with bipolar disorder identified from discordant monozygotic twins," Molecular Psychiatry, 13:429-441 (2008).

Lal, R. B. et al., "Fixation and Long-Term Storage of Human Lymphocytes for Surface Marker Analysis by Flow Cytometq," Cytometry, 9:213-219 (1988).
Langel, K. et al., "Drug Testing in Oral Fluid—Evaluation of Sample Collection Devices", Journal of Analytical Toxicology, vol. 32, Jul./Aug. 2008, pp. 393-401.
Lassen, K. G. et al., "Analysis of Human Immunodeficiency Virus Type 1 Transcriptional Elongation in Resting CD4+T Cells In Vivo," Journal of Virology, 78(17):9105-9114 (2004).
Lister, R. et al., "Human DNA methylomes at base resolution show widespread epigenomic differences," Nature, 462:315-322 (2009).
Loens, K. et al., "Detection of Mycoplasma pneumoniae in Spiked Clinical Samples by Nucleic Acid Sequence-Based Amplification," Journal of Clinical Microbiology, 40(4):1339-1345 (2002).
Longmire, J. L. et al., "Use of 'Lysis Buffer' in DNA isolation and its implication for museum collections," Occasional Papers, Museum of Texas Tech University, 163:1-3 (1997).
Lum, A. & Le Marchand, L., "A Simple Mouthwash Method for Obtaining Genomic DNA in Molecular Epidemiological Studies," Cancer Epidemiology, Biomarkers & Prevention, 7:719-724 (1998).
Markman, M. "Genetics of Non-Small Cell Lung Cancer," Aug. 21, 2019, 6 pages; https://emedicine.medscape.com/article/1689988-print.
Mastroeni, D. et al., "Epigenetic changes in Alzheimer's disease: decrements in DNA methylation," Neurobiol Aging, 31(12):2025-2037 (2010).
Matos-Gomes, N. et al., "Psychological Stress and Its Influence on Salivary Flow Rate, Total Protein Concentration and IgA, IgG and IgM Titers," Neuroimmunomodulation, 17:396-404 (2010).
Maunakea, A. K. et al., "Epigenome Mapping in Normal and Disease States," Circ Res.. 107:327-339 (2010).
McGowan, P. O. & Kato, T., "Epigenetics in mood disorders," Environ Health Prev Med, 13:16-24 (2008).
McGowan, P. O. et al., "Epigenetic regulation of the glucocorticoid receptor in human brain associates with childhood abuse," Nature Neuroscience, 12(3):342-348 (2009).
McGowan, P. O. & Szyf, M., "The epigenetics of social adversity in early life: Implications for mental health outcomes," Neurobiology of Disease, 39:66-72 (2010).
Mens, H. et al., "Amplifying and Quantifying HIV-1 RNA in HIV Infected Individuals with Viral Loads Below the Limit of Detection by Standard Clinical Assays," J Vis Exp., (55):2960 (2011), 8 pages; doi:10.3791/2960.
Meulenbelt, I. et al. "High-Yield Noninvasive Human Genomic DNA Isolation Method for Genetic Studies in Geographically Dispersed Families and Populations," American Journal of Human Genetics, 1995, vol. 57, No. 1252-1254, 3 pages.
Mill, J. & Petronis, A., "Molecular studies of major depressive disorder: the epigenetic perspective," Molecular Psychiatry, 12:799-814 (2007).
Miller, D. M. et al., "Transition metals as catalysts of 'autoxidation' reactions," Free Radic Biol Med., 8(1):95-108 (1990).
Nilsson, P. et al., "Real-Time Monitoring of DNA Manipulations Using Biosensor Technology," Analytical Biochemistry, 224:400-408 (1995).
Noguera, A. et al., "Enhanced neutrophil response in chronic obstructive pulmonary disease," Thorax, 56:432-437 (2001).
Offner, G. D. & Troxler, R. F., "Heterogeneity of high-molecular-weight human salivary mucins," Adv Dent Res., 14:69-75 (2000).
O'Neil, J. D. et al., "HIV Nucleic Acid Amplification Testing Versus Rapid Testing: It Is Worth the Wait. Testing Preferences of Men Who Have Sex with Men," J Acquir Immune Defic Syndr., 60(4):e119-e122 (2012); doi:10.1097/QAI.0b013e31825aab51.
Peedicayil, J., "The role of epigenetics in mental disorders," Indian J Med Res, 126:105-111 (2007).
Petronis, A. et al., "Schizophrenia: An Epigenetic Puzzle?" Schizophrenia Bulletin, 25(4):639-655 (1999).
Pershadsingh, H. A. & Mcdonald, J. M., "A High Affinity Calcium-stimulated Magnesium-dependent Adenosine Triphosphatase in Rat Adipocyte Plasma Membranes," The Journal of Biological Chemistry, 255(9):4087-4093 (1980).
Pink, R. et al., "Saliva as a Diagnostic Medium," Biomed Pap Med Fac Univ Palacky Olomouc Czech Repub, 153(2):103-110 (2009).

(56) References Cited

OTHER PUBLICATIONS

Plazas-Mayorca, M. D. & Vrana, K. E., "Proteomic Investigation of Epigenetics in Neuropsychiatric Disorders: A Missing Link between Genetics and Behavior?" Journal of Proteome Research, 10:58-65 (2011).
Portela, A. & Esteller, M., "Epigenetic modifications and human disease," Nature Biotechnology, 28(10):1057-1068 (2010).
Rahman, M. et al., "Chromatography paper strip method for collection, transportation, and storage of rotavirus RNA in stool samples," J Clin Microbiol., 42(4):1605-08 (2004).
Reynolds, J. D. et al., "Comparison of high density genotyping results from saliva and blood samples on Affymetrix GeneChip® GenomeWide SNP 6.0 arrays," Poster, 1 page.
Righini, C. A. et al., "Tumor-Specific Methylation in Saliva: A Promising Biomarker for Early Detection of Head and Neck Cancer Recurrence," Clin Cancer Res, 13(4):1179-1185 (2007).
Roberts, M. A. et al., "UV Laser Machined Polymer Substrates for the Development of Microdiagnostic Systems," Analytical Chemistry, 69:2035-2042 (1997).
Romanus, D. et al., "Cost-Effectiveness of Multiplexed Predictive Biomarker Screening in Non-Small-Cell Lung Cancer," J Thorac Oncol., 10:586-594 (2015).
Rosas, S. L. B. et al., "Promoter Hypermethylation Patterns of p16, O6-ethylguanine-DNAmethyltransferase, and Death-associated Protein Kinase in Tumors and Saliva of Head and Neck Cancer Patients," Cancer Research, 61:939-942 (2001).
Russo, P. et al.,"Heritability of body weight: Moving beyond genetics," Nutrition, Metabolism & Cardiovascular Diseases, 20:691-697 (2010).
Rymaszewski, M. A. et al., "Estimation of Cellular DNA Content in Cell Lysates Suitable for RNA Isolation," Analytical Biochemistry, 188:91-96 (1990).
Saha, S. & Brightling, C. E., "Eosinophilic airway inflammation in COPD," International Journal of COPD, 1(1):39-47 (2006).
Schilter, H. C. et al., "Effects of an anti-inflammatory VAP-1/SSAO inhibitor, PXS-4728A, on pulmonary neutrophil migration," Respiratory Research, 16:42 (2015), 14 pages; doi:10.1186/s12931-015-0200-z.
Schmitteckert, E. M. et al., "DNA detection in hair of transgenic mice—a simple technique minimizing the distress on the animals," Lab Anim., 33(4):385-9 (1999).
Seregni, E. et al., "Structure, function, and gene expression of epithelial mucins," Tumori., 83(3):625-32 (1997).
Seutin, G. et al., "Preservation of Avian Blood and Tissue Samples for DNA Analyses," Canadian Journal of Zoology, 69:82-90 (1991).
Shaya, F. T. et al., "Burden of COPD, Asthma, and Concomitant COPD and Asthma Among Adults," Chest, 136:405-411 (2009).
Sindhu, S. et al., "Saliva: A Cutting Edge in Diagnostic Procedures," Journal of Oral Diseases, vol. 2014, Article ID 168584 (May 2014), 8 pages; http://dx.doi.org/10.1155/2014/168584.
Singh, D. et al., "Eosinophilic inflammation in COPD: prevalence and clinical characteristics," European Respiratory Journal, 44:1697-1700 (2014).
Singh, D. et al., "Sputum neutrophils as a biomarker in COPD: findings from the ECLIPSE study," Respiratory Research, 11:77 (2010), 12 pages; doi:10.1186/1465-9921-11-77.
Smith, B. D. et al., "Potent inhibition of ribonuclease A by oligo(vinylsulfonic acid)," J Biol Chem., 278(23):20934-38 (2003).
Sterlacci, W. et al., "Putative Stem Cell Markers in Non-Small-Cell Lung Cancer A Clinicopathologic Characterization," J Thorac Oncol., 9:41-49 (2014).
Terasaki, P. et al., "Saliva as DNA Source for HLA Typing," Human Immunology, 59:597-598 (1998).
Thunnissen, F. B. J. M., "Sputum examination for early detection of lung cancer," J Clin Pathol, 56:805-810 (2003).
Tierling, S. et al., "DNA methylation studies on imprinted loci in a male monozygotic twin pair discordant for Beckwith-Wiedemann syndrome," Clin Genet, 79:546-553 (2011).
Tsai, S. -J. et al., "Recent molecular genetic studies and methodological issues in suicide research," Progress in Neuro-Psychopharmacology & Biological Psychiatry, 35:809-817 (2011).
Van Schie, R. C. A. A. & Wilson, M. E., "Saliva: a convenient source of DNA for analysis of bi-allelic polymorph isms of Fcg receptor I IA (CD32) and Fcg receptor IIIB (CD16)," Journal of Immunological Methods, 208:91-101 (1997).
Videira, A. & Werner, S., "Assembly Kinetics and Identification of Precursor Proteins of Complex I from Neurospora Crassa," European Journal of Biochemistry, 181:493-502 (1989).
Vidović, A. et al., "Determination of leucocyte subsets in human saliva by flow cytometry," Archives of Oral Biology, 57:577-583 (2012).
Viet, C. T. & Schmidt, B. L., "Methylation Array Analysis of Preoperative and Postoperative Saliva DNA in Oral Cancer Patients," Cancer Epidemiol Biomarkers Prev, 17(12):3603-3611 (2008).
Vlaanderen, J. et al., "Application of OMICS technologies in occupational and environmental health research; current status and projections," Occup Environ Med, 67:136-143 (2010).
Vyboh, K. et al., "Detection of Viral RNA by Fluorescence in situ Hybridization (FISH)," J. Vis. Exp., 63:e4002 (2012), 5 pages; doi:10.3791/4002.
Wang, D. O. et al., "A quick and simple FISH protocol with hybridization-sensitive fluorescent linear oligodeoxynucleotide probes," RNA, 18:166-175 (2012).
Welham, M. J., "VAP-1: a new anti-inflammatory target?" Blood, 103(9):3250-3251 (2004).
Wollants, E. et al., "Evaluation of a norovirus sampling method using sodium dodecyl sulfate/EDTA-pretreated chromatography paper strips," J Virol Methods, 122(1):45-48 (2004).
Wu, H. et al., "Is CD133 Expression a Prognostic Biomarker of Non-Small-Cell Lung Cancer? A Systematic Review and Meta-Analysis," PLoS ONE 9(6):e100168 (2014), 8 pages; doi:10.1371/journal.pone.0100168.
Yamamoto, C. et al., "Airway Inflammation in COPD Assessed by Sputum levels of Interleukin-8," Chest, 112:505-510 (1997).
Yang, J. et al., "Detection of Tumor Cell-Specific mRNA and Protein in Exosome-Like Microvesicles from Blood and Saliva," PLoS One, 9(11):e110641 (2014), 10 pages; doi:10.1371/journal.pone.0110641.
Yigla, M. et al., "Oxidative stress indices in COPD—Bronchoalveolar lavage and salivary analysis," Archives of Oral Biology, 52:36-43 (2007).
Xiao, H. et al., "Proteomic Analysis of Human Saliva From Lung Cancer Patients Using Two-Dimensional Difference Gel Electrophoresis and Mass Spectrometry," Molecular & Cellular Proteomics, 11:1-12(2012).
Zhang, F. F. et al., "Physical activity and global genomic DNA methylation in a cancer-free population," Epigenetics, 6(3):293-299 (2011).
Zhang, L. et al., "Salivary Transcriptomic Biomarkers for Detection of Resectable Pancreatic Cancer," Gostroenterology, 138(3):949-957 (2010).
Zhang, L. et al., "Discovery and Preclinical Validatio of Salivary Transcriptomic and Proteomic Biomarkers for the Non-lnvasive Detection of Breast Cancer," PLoS ONE, 5(12):e15573 (2010), 7 pages; doi:10.1371/journal.pone.0015573.
Complaint for Patent Infringement against Spectrum Pharmaceuticals, S.D. Cal., Case No. 21-cv-0516, Filed Mar. 24, 2021 by DNA Genotek (38 pages).
First Amended Complaint for Patent Infringement, S.D. Cal., Case No. 21-cv-0516, Filed Jun. 8, 2021 by DNA Genotek (14 pages).
Spectrum's Answer and Counterclaim to First Amended Complaint, S.D. Cal., Case No. 21-cv-0516, Filed Jun. 22, 2021 (13 pages).
Plaintiff and Counter-Defendant DNA Genotek Inc.'s Answer to Defendant and Counter-Claimant Spectrum Solutions, LLC's Counterclaims, S.D. Cal., Case No. 21-cv-0516, Filed Jul. 13, 2021 (4 pages).
Second Amended Complaint for Patent Infringement, S.D. Cal., Case No. 21-cv-0516, Filed Aug. 4, 2021 by DNA Genotek (21 pages).

(56) References Cited

OTHER PUBLICATIONS

Spectrum's Answer and Counterclaim to Second Amended Complaint, S.D. Cal., Case No. 21-cv-0516, Filed Aug. 18, 2021 (71 pages).
Notice of Motion and Motion by Plaintiff DNA Genotek Inc. to Dismiss and Strike Defendant Spectrum Solutions LLC's Counterclaims and Affirmative Defenses Pursuant to Fed. R. Civ. P. 12(B)(6) and 12(F), S.D. Cal., Case No. 21-cv-0516, Filed Oct. 14, 2021 (3 pages).
Memorandum of Points and Authorities in Support of DNA Genotek Inc.'s Motion to Dismiss and Strike Defendant Spectrum Solution LLC's Counterclaims and Affirmative Defenses Pursuant to Fed. R. Civ. P. 12(B)(6) and 12(F), S.D. Cal., Case No. 21-cv-0516, Filed Oct. 14, 2021 (31 pages).
Anchordoquy, T. J. & Molina, M. C "Frontiers in Clinical Research. Preservation of DNA," Cell Preservation Technology, 5(4):180-188 (2007).
Cunningham, J. M. et al., "Mutation Detection in Colorectal Cancers: Direct Sequencing of DNA Mismatch Repair Genes", Colorectal Cancer: Methods and Protocols, Chapter 10, pp. 87-98 (2001).
Eigner, J. et al., "The thermal degradation of nucleic acids," Biochim. Biophys. Acta, 51:165-168 (1961).
Freeman, B. et al., "DNA by Mail: An Inexpensive and Noninvasive Method for Collecting DNA Samples from Widely Dispersed Populations," Behavior Genetics, 27(3):251-257 (1997).
Goldenberger, D. et al., "A Simple 'Universal' DNA Extraction Procedure Using SDS and Proteinase K Is Compatible with Direct PCR Amplification," PCT Methods and Applications, (6):368-370(1995).
Noll, H. & Stutz, E., "The Use of Sodium and Lithium Dodecyl Sulfate in Nucleic Acid Isolation," Methods in Enzymology, 12:129-155 (1968).
Quinn, F. D., "Sample Preparation for Nucleic Acid Amplification," Nucleic Acid Amplification Technologies: Application to Disease Diagnosis, Chapter 4, pp. 49-60 (1997).
Streckfus, C. F. & Bigler, L. R "Salivas as a diagnostic fluid," Oral Diseases, 8:69-79 (2002).
Tabak, L. A., "A Revolution in Biomedical Assessment: The Development of Salivary Diagnostics," Journal of Dental Education, 65:1336-1339 (2001).
Tuttle, M. R. et al., "Preservation of Nucleic Acids for Polymerase Chain Reaction After Prolonged Storage at Room Temperature," Diagnostic Molecular Pathology, 7(6):302-309 (1998).
Inter Partes Review between Applicant and Spectrum Solutions L.L.C, before the Patent Trial and Appeal Board (*Spectrum Solutions L.L.C*, v. *DNA Genotek Inc*., IPR2022-00134 Patent 10,767,215), filed Nov. 2, 2021.
Patent Owner's Preliminary Response filed Mar. 15, 2022 in Inter Partes Review between Applicant and Spectrum Solutions L.L.C, before the Patent Trial and Appeal Board (*Spectrum Solutions L.L.C*, v. *DNA Genotek Inc.*, IPR2022-00134 Patent 10,767,215).
Decision dated Jun. 6, 2022, Granting Institution of Inter Partes Review in IPR2022-00134 under U.S.C. § 314 (*Spectrum Solutions L.L.C*, v. *DNA Genotek Inc.*, IPR2022-00134 Patent 10,767,215).
Petition for Inter Partes Review of U.S. Pat. No. 10,000,795 between Applicant and Spectrum Solutions L.L.C, before the Patent Trial and Appeal Board (*Spectrum Solutions L.L.C*, v. *DNA Genotek Inc.*, IPR2022-00774 Patent 10,000,795), filed Mar. 28, 2022.
"Spectrum Solution LLC's memorandum in opposition to DNA Genotek Inc.'s motion to dismiss and strike defendant Spectrum Solutions LLC's counterclaims and affirmative defenses" before the United States District Court Southern District of California (*DNA Genotek Inc.* v. *Spectrum Solutions L.L.C.*, Case No. 21-cv-0516-JO-AGS), dated Jan. 11, 2022.
"Reply in support of plaintiff DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.* v. *Spectrum Solutions L.L.C.*, Case No. 21-cv-0516-JO-AGS), dated Feb. 1, 2022.

"Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.* v. *Spectrum Solutions L.L.C.*, Case No. 21-cv-0516-JO-AGS), dated Feb. 1, 2022.
"Exhibit 1 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(8)(6) and 12(F)" before the United States District Court Southern District of California (*DNA Genotek Inc.* v. *Spectrum Solutions L.L.C.*, Case No. 21-cv-0516-JO-AGS), dated Feb. 1, 2022, is a copy of the index of the electronic record for U.S. Appl. No. 16/986,765 ("the '765 application").
"Exhibit 2 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(8)(6) and 12(F)" before the United States District Court Southern District of California (*DNA Genotek Inc.* v. *Spectrum Solutions L.L.C.*, Case No. 21-cv-0516-JO-AGS), dated Feb. 1, 2022, is a copy of a list of references cited by DNA Genotek in the '765 application.
"Exhibit 3 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(8)(6) and 12(F)" before the United States District Court Southern District of California (*DNA Genotek Inc.* v. *Spectrum Solutions L.L.C.*, Case No. 21-cv-0516-JO-AGS), dated Feb. 1, 2022, is a copy of an Information Disclosure Statement filed by DNAGenotek in the '765 application.
"Exhibit 4 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(8)(6) and 12(F)" before the United States District Court Southern District of California (*DNA Genotek Inc.* v. *Spectrum Solutions L.L.C.*, Case No. 21-cv-0516-JO-AGS), dated Feb. 1, 2022, is a copy of the Notice of Allowability of the '765 application.
"Spectrum's Invalidity Contentions Under PLR 3.3 and Accompanying Document Production Under PLR 3.4", before the United States District Court Southern District of California (*DNA Genotek Inc.* v. *Spectrum Solutions L.L.C.*, Case No. 3:21-cv-00516-DMS-LL), dated Nov. 19, 2021.
Appendix A: Invalidity Claim Chart for U.S. Pat. No. 10,619,187, Fischetti—U.S. Pat. No. 5,643,767 from "Spectrum's Invalidity Contentions under PLR 3.3 and accompanying document production under PLR 3.4" before the United States District Court Southern District of California (*DNA Genotek Inc.* v. *Spectrum Solutions L.L.C.*, Case No. 3:21-cv-00516-DMS-LL), dated Nov. 19, 2021.
Appendix B: Invalidity Claim Chart for U.S. Pat. No. 10,619,187, Soane—PCT Publication No. WOOO/10884 from "Spectrum's Invalidity Contentions under PLR 3.3 and accompanying document production under PLR 3.4" before the United States District Court Southern District of California (*DNA Genotek Inc.* v. *Spectrum Solutions L.L.C.*, Case No. 3:21-cv-00516-DMS-LL), dated Nov. 19, 2021.
Appendix C: Invalidity Claim Chart for U.S. Pat. No. 10,619,187, Moscovitz 113—U.S. Pat. No. 6,533,113 from "Spectrum's Invalidity Contentions under PLR 3.3 and accompanying document production under PLR 3.4" before the United States District Court Southern District of California (*DNA Genotek Inc.* v. *Spectrum Solutions L.L.C.*, Case No. 3:21-cv-00516-DMS-LL), dated Nov. 19, 2021.
Appendix D: Invalidity Claim Chart for U.S. Pat. No. 10,619,187, Moscovitz 110—U.S. Pat. No. 6,527,110 from "Spectrum's Invalidity Contentions under PLR 3.3 and accompanying document production under PLR 3.4" before the United States District Court Southern District of California (*DNA Genotek Inc.* v. *Spectrum Solutions L.L.C.*, Case No. 3:21-cv-00516-DMS-LL), dated Nov. 19, 2021.
Appendix E: Invalidity Claim Chart for U.S. Pat. No. 10,619,187, Okauchi—PCT Publication No. WO98/03265 from "Spectrum's

(56) References Cited

OTHER PUBLICATIONS

Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Appendix F: Invalidity Claim Chart for U.S. Pat. No. 10,619,187, Finke—U.S. Pat. No. 4,591,050 from "Spectrum's Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Appendix G: Invalidity Claim Chart for U.S. Pat. No. 10,619,187, Guirguis—PCT Publication No. WO 98/038917 from "Spectrum's Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Appendix H: Claim Chart for U.S. Pat. No. 11,002,646, U.S. Patent Pub. No. 2009/0216213 ("Muir"), WO 2005/051775 ("Cho"), U.S. Pat. No. 5,967,309 (Robles-Gonzalez), U.S. 2009/0133366 ("Cronin") from "Spectrum's Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Appendix I: Invalidity Claim Chart for U.S. Pat. No. 11,002,646, U.S. Patent Pub. No. 2012/0325721 ("Plante"), WO 2005/051775 ("Cho"), U.S. Pat. No. 5,967,309 ("Robles-Gonzalez"), U.S. Patent Pub. No. 2009/0133366 ("Cronin") from "Spectrum's Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Appendix J: Claim Chart for U.S. Pat. No. 11,002,646, U.S. Patent Pub. No. 2004/0161788 ("Chen"), WO 2005/051775 ("Cho"), U.S. Pat. No. 5,967,309 ("Robles-Gonzalez"), U.S. Patent Pub. No. 2009/0133366 ("Cronin") from "Spectrum's Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Appendix K: Invalidity Claim Chart for U.S. Pat. No. 11,002,646, U.S. 2008/0293156 ("Smith"), WO 2005/051775 ("Cho"), U.S. Pat. No. 5,967,309 ("Robles-Gonzalez"), U.S. Patent Pub. No. 2009/0133366 ("Cronin") from "Spectrum's Invalidity Contentions under PLR 3.3 and accompanying document production under PLR 3.4" before the United States District Court Southern District of California (*DNA Genotek Inc. v. Spectrum Solutions L.L.C.*, Case No. 3:21-cv-00516-DMS-LL), dated Nov. 19, 2021.
Spectrum Solutions, LLC's Opening Claim Construction Brief before the United States District Court Southern District of California (*DNA Genotek Inc. v. Spectrum Solutions L.L.C.*, Case No. 21-cv-0516-JO-AGS), dated Feb. 18, 2022.
Declaration of Ali S. Razai in Support of Spectrum Solution LLC's Opening Claim Construction Brief before the United States District Court Southern District of California (*DNA Genotek Inc. v. Spectrum Solutions L.L.C.*, Case No. 21-cv-0516-JOAGS), dated Feb. 18, 2022.
Declaration of Vincent A. Fischetti, Ph.D. before the United States District Court Southern District of California (*DNA Genotek Inc. v. Spectrum Solutions L.L.C.*, Case No. 21-cv-0516-JO-AGS), dated Feb. 19, 2022.
Defendant Spectrum Solutions, L.L.C.'s Responsive Claim Construction Brief before the United States District Court Southern District of California (*DNA Genotek Inc. v. Spectrum Solutions L.L.C.*, Case No. 21-cv-0516-JO-AGS), dated Mar. 4, 2022.
Plaintiff DNA Genotek Inc.'s Responsive Claim Construction Brief before the United States District Court Southern District of California (*DNA Genotek Inc. v. Spectrum Solutions L.L.C.*, Case No. 21-cv-0516-JO-AGS), dated Mar. 4, 2022.
Notice of Errata and Declaration of Vincent A. Fischetti, Ph.D. before the United States District Court Southern District of California (*DNA Genotek Inc. v. Spectrum Solutions L.L.C.*, Case No. 21-cv-0516-JO-AGS), dated Mar. 21, 2022.
Order Denying Plaintiff/Counter Defendant's Motion to Dismiss Counterclaims and Denying Motion to Strike Without Prejudice before the United States District Court Southern District of California (*DNA Genotek Inc. v. Spectrum Solutions L.L.C.*, Case No. 21-cv-0516-JO-AGS), dated Apr. 1, 2022.
DNA Genotek Inc.'s Answer to Spectrum Solutions L.L.C.'s Counterclaims before the United States District Court Southern District of California (*DNA Genotek Inc. v. Spectrum Solutions L.L.C.*, Case No. 21-cv-0516-JO-AGS), dated Apr. 13, 2022.
DNA Genotek Inc.'s Notice of Errata to Opening Claim Construction Brief before the United States District Court Southern District of California (*DNA Genotek Inc. v. Spectrum Solutions L.L.C.*, Case No. 21-cv-0516-JO-AGS), dated Jul. 18, 2022.
DNA Genotek Inc.'s Corrected Opening Claim Construction Brief before the United States District Court Southern District of California (*DNA Genotek Inc. v. Spectrum Solutions L.L.C.*, Case No. 21-cv-0516-JO-AGS), dated Jul. 19, 2022.
Docket dated Aug. 5, 2022 for DNA Genotek Inc. v. Spectrum Solutions L.L.C, before the United States District Court Southern District of California (*DNA Genotek Inc. v. Spectrum Solutions L.L.C.*, Case No. 21-cv-0516-JO-AGS).
Anker, P. et al., "Detection of circulating tumour DNA in the blood (plasma/serum) of cancer patients," Cancer and Metastasis Reviews, 18:65-73 (1999); doi: https://doi.org/10.1023/A:1006260319913.
Backhed, F. et al., "The gut microbiota as an environmental factor that regulates fat storage," PNAS, 101(44):15718-15723 (2004); doi:10.1073/pnas.0407076101.
Bouvard, V. et al.,. "A review of human carcinogens-Part B: Biological agents," The Lancet Oncology, 10:321-322 (2009).
Bussemakers, M. J. et al., "DD3: a new prostate-specific gene, highly overexpressed in prostate cancer," Cancer Res, 59:5975-5979 (1999).
Chen, Z. et al., "RNase activity requires formation of disulfide bonds and is regulated by the redox state," Pant Molecular Biology, 55:83-96 (2004).
Clarke, T. B. et al., "Recognition of peptidoglycan from the microbiota by Nodi enhances systemic innate immunity," Nat Med, 16(2):228-231 (2010); doi:10.1038/nm.2087.
Commichau, F. M. et al., "Novel activities of glycolytic enzymes in Bacillus subtilis," Molecular & Cellular Proteomics, 8(6): 1350-1360 (2009); doi:10.1074/MCP.M800546-MCP200.
Condon, C., "Rna processing and degradation in Bacillus subtilis," Microbiol Mol Biol Rev, 67(2): 157-174 (2003); doi: 10.1128/MMBR.67.2.157-174.2003.
Coresh, J. et al., "Prevalence of chronic kidney disease in the United States," JAMA, 298(17):2038-2047 (2007).
Dethlefsen, L. et al., "An ecological and evolutionary perspective on human-microbiome mutualism and disease," Nature, 449:811-818 (2007); doi:10.1038/nature06245.
Dupureur, C. M. et al., "Roles of metal ions in nucleases," Current Opinion in Chemical Biology, 12:250-255 (2008).
Ernst, P. O. et al., "The effects of pH on DNA methylation state: In vitro and post-mortem brain studies," J Neurosci Methods, 174(1): 123-125 (2008).
Gilbert, M. T. P. et al., "The isolation of nucleic acids from fixed, paraffin-embedded tissues - Which methods are useful when?" PLoS ONE, 2(6): e537 (2007); doi: 10.1371/journal.pone.0000537.
Jahr, S. et al., "DNA fragments in the blood plasma of cancer patients: quantitations and evidence for their origin from apoptotic and necrotic cells," Cancer Res, 61 (4): 1659-1665 (2001).
Jung, M. et al., "Changes in concentration of DNA in serum and plasma during storage of blood samples," Clinical Chern, 49(6): 1028-1029 (2003).
Kim, B. M. et al., "Variants of ribonuclease inhibitor that resist oxidation," Protein Science, 8:430-434 (1999).

(56) References Cited

OTHER PUBLICATIONS

Koenig, J. E. et al., "Succession of microbial consortia in the developing infant gut microbiome," PNAS, 108(1):4578-4585 (2010); doi: 10.1073/pnas.1000081107.

Langmead, B. & Salzberg, S. L, "Fast gapped-read alignment with Bowtie 2," Nature Methods, 9(4), 357-359 (2012).

Lee, Y. -H. & Wong, D. T., "Saliva: an emerging biofluid for early detection of diseases," Am J Dent, 22(4): 241-248 (2009).

Leon, S. A. et al., "Free DNA in the serum of cancer patients and the effect of therapy," Cancer Res, 37:646-650 (1977).

Ley, R. E. et al., "Human gut microbes associated with obesity," Nature, 444(21): 1022-1023 (2006); doi:10.1038/nature4441022a.

Li, Y. & Tollefsbol, T. O., "DNA methylation detection: Bisulfite genomic sequencing analysis," Methods Mol Biol, 791:11-21 (2011); doi: 10.1007/978-1-61779-316-5_2.

Lovett, S. T., "The DNA exonucleases of Escherichia coli," EcoSai Plus, 4(2) (2011); doi: 10.1128/ecosalplus.4.4.7.

Mandel, P. et al., "Les acides nucleiques du plasma sanguine chez l'homme," C RAcad Sci Paris: 241-243 (1948) - with English machine translation, 6 pages.

Mikkelsen, N. E. et al., "Inhibition of RNAse P Rna cleavage by aminoglycosides," PNAS, 96:6155-6160 (1999).

Miranda, K. C. et al., "Nucleic acids within urinary exosomes/microvesicles are potential biomarkers for renal disease," Kidney Int, 78(2): 191 -199 (2010); doi:10.1038/ki.2010.106.

Münoz, N. et al., "Epidemiologic classification of human papillomavirus types associated with cervical cancer," N Engl J Med, 348(6):518-527 (2003); doi:10.1056/NEJMoa021641.

Nilsson, J. et al., "Prostate cancer-derived urine exosomes: a novel approach to biomarkers for prostate cancer," Br J Cancer, 100:1603-1607 (2009);doi:10.1038/sj.bjc.6605058.

Sikorsky, J. A. et al., "DNA damage reduces Taq DNA polymerase fidelity and PCR amplification efficiency," Biochem Biophys Res Commun, 355(2):431-437 (2007).

Sorrentino, S., "The eight human "canonical" ribonucleases: Molecular diversity, catalytic properties, and special biological actions of the enzyme proteins," FEBS Letters, 584: 2194-2200 (2010); doi:10.1016/febslet.2010.04.018.

Srinivasan, M. et al., "Effect of fixatives and tissue processing on the content and integrity of nucleic acids," Am J Pathol, 161 (6): 1961-1971 (2002).

Stroun, M. et al., "About the possible origin and mechanism of circulating DNA apoptosis and active DNA release," Clin Chim Acta, 313(1-2):139-142 (2001).

Valadi, H. et al., "Exosome-mediated transfer of mRNAs and microRNAs is a novel mechanism of genetic exchange between cells," Nature Cell Biology, 9:654-659 (2007).

Wolf, B. et al., "A mechanism of the irreversible inactivation of bovine pancreatic ribonuclease by diethylpyrocarbonate," Eur J Biochem, 13:519-525 (1970).

Yang, W., "Nucleases: Diversity of structure, function and mechanism," Q Rev Biophys, 44(1): 1-93 (2011); doi:10.1017/S0033583510000181.

Petition for Inter Partes Review of U.S. Pat. No. 11,002,646, U.S. Patent Trial and Appeal Board, Case No. IPR2022-01347, Patent No. 11,002,646, filed Jul. 29, 2022 (Parts 1 and 2, 102 total pages.

Exhibit 1002—Declaration of Karl R. Leinsing, MSME, PE (95 pages).

Exhibit 1006—Excerpts from LinkedIn profile for Youssef Biadillah (4 pages).

Exhibit 1007—Excerpts from LinkedIn profile for Stephen D. Andrews (2 pages).

Exhibit 1011—Declaration of Vincent A. Fischetti, Ph.D. (20 pages).

Exhibit 1012—Excerpts of Prosecution History of U.S. Appl. No. 16/879,506 (34 pages).

Exhibit 1013—Spectrum Solutions L.L.C.'s [Redacted] Opening Claim Construction Brief filed in *DNA Genotek Inc. v. Spectrum Solutions LLC*, C.A. No. 21-cv-0516 (S. D. Cal.) (42 pages).

Exhibit 1014—DNA Genotek Inc.'s Opening Claim Construction Brief filed in *DNA Genotek inc. v. Spectrum Solutions LLC*, C.A. No. 21-cv-051 6 (S.D. Cal.) (36 pages).

Exhibit 1015—"Needle Stick Safety and Prevention Act" of Nov. 6, 2000, Public Law 106-430, 114 Stat. 1901 (4 pages).

Exhibit 1017—*Curriculum Vitae* of Karl R. Leinsing, MSME, PE (10 pages).

Exhibit 1018—*Curriculum Vitae* of Vincent A. Fischetti, Ph.D. (7 pages).

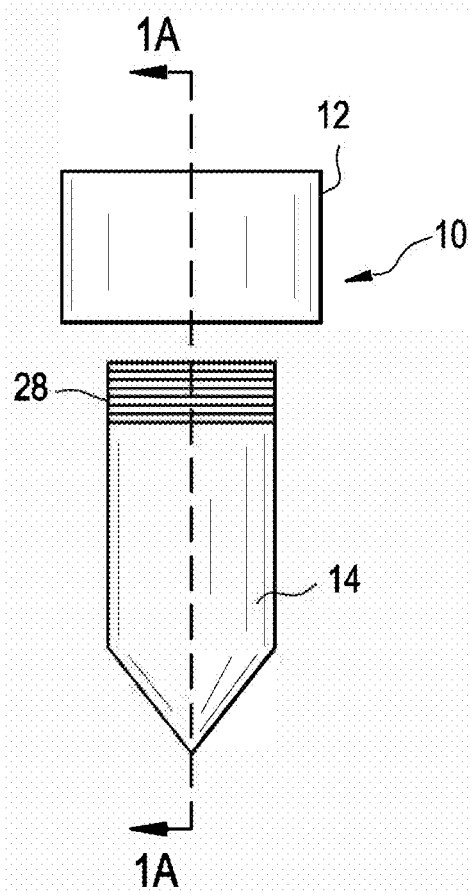

FIG. 2A
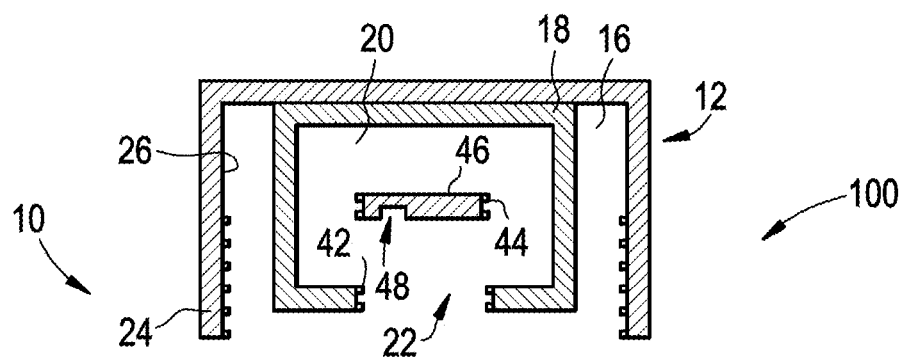
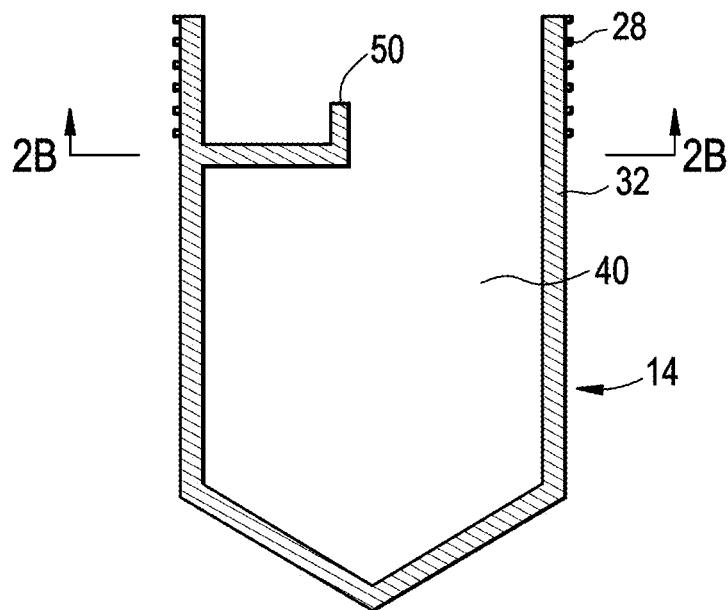
FIG. 2B
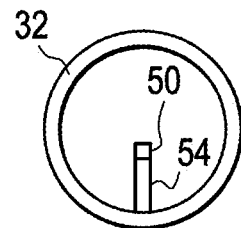

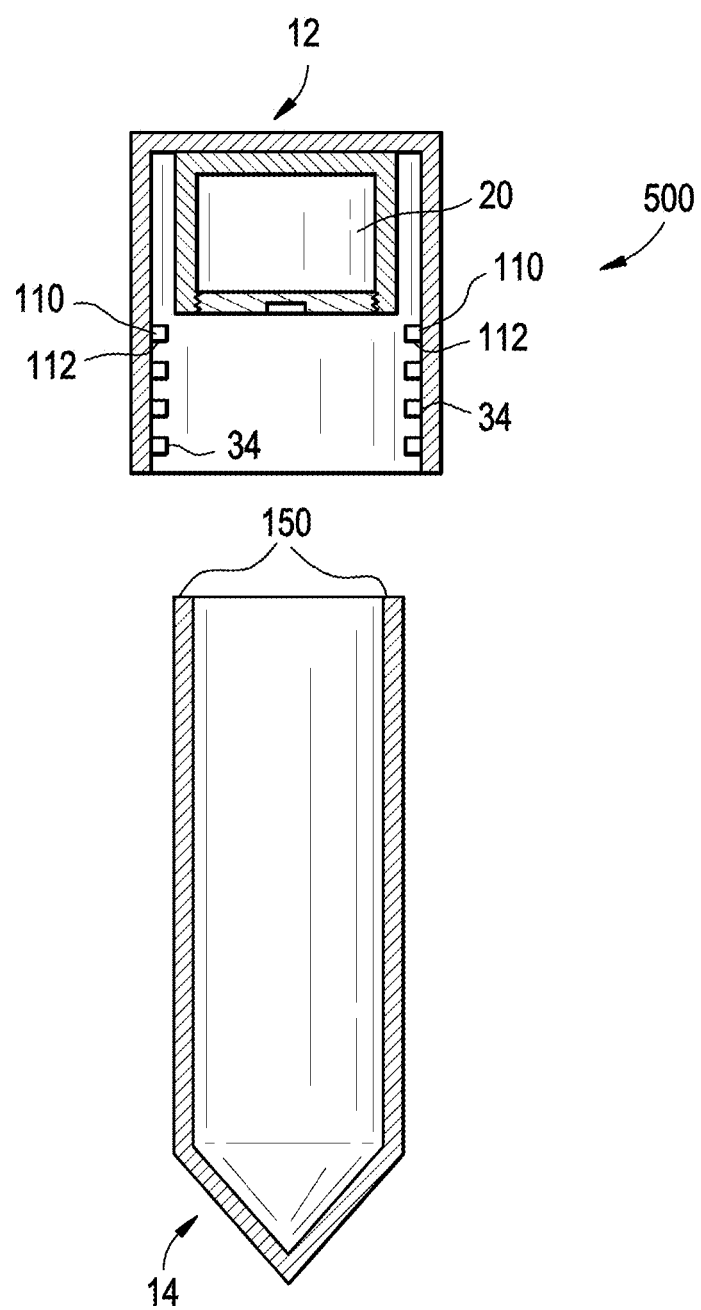

FIG. 7A
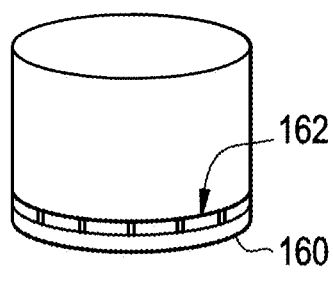
FIG. 7B
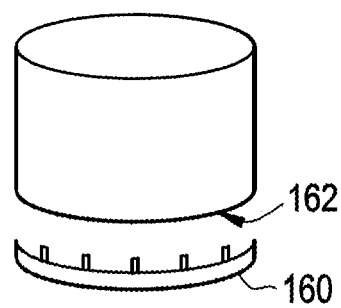
FIG. 8
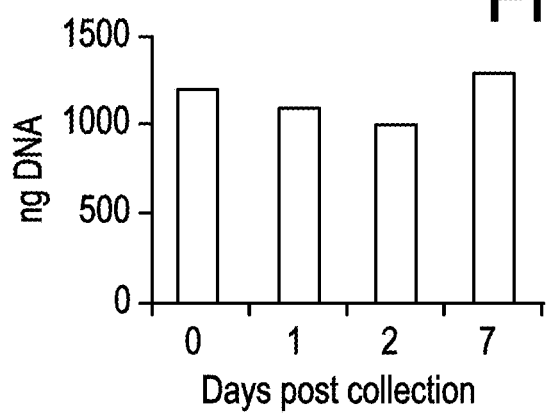
Time course of DNA yield of isolated T-cells after saliva samples stored in preservation solution at room temperature and then proceed.
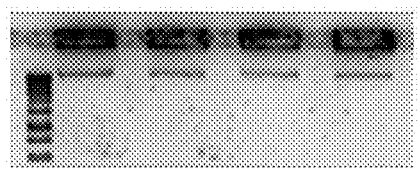
DNA extracted from isolated T-cells after stored in preservation solution for indicated time.

Relative yield of extracted T-cells from saliva per ml of starting material compared to yield of T-cells from blood as determined By T-cell counting using light microscopy.

Saliva dose curve. Micrograms of isolated T-cell DNA per ml of starting saliva

METHOD FOR COLLECTING AND PRESERVING A BIOLOGICAL SAMPLE

RELATED APPLICATIONS

This application is a continuation of U.S. patent application Ser. No. 16/023,772, filed Jun. 29, 2018, which is a continuation of U.S. patent application Ser. No. 15/227,693, filed Aug. 3, 2016, which is a continuation of U.S. patent application Ser. No. 14/127,832, filed Dec. 19, 2013, now U.S. Pat. No. 9,442,046, which is a 35 U.S.C. § 371 national stage entry of PCT/US2012/043176, filed Jun. 19, 2012, and claims priority under 35 USC § 119(e) to U.S. provisional patent application Nos. 61/498,584, filed Jun. 19, 2011, 61/598,601, filed Feb. 14, 2012, and 61/598,618, filed Feb. 14, 2012. Each disclosure of the foregoing is herein incorporated by reference in its entirety.

FIELD OF THE DISCLOSURE

The disclosure relates to devices, solutions and methods for collecting samples of bodily fluids or other substances, including hazardous and/or toxic substances, and in particular, a naturally expressed bodily fluid (e.g., saliva, urine). In addition, the disclosure relates generally to functional genomics and to the isolation and preservation of cells from such bodily fluids, for studies in any of: functional genomic and epigenetic studies, and biomarker discovery (for example).

BACKGROUND

Personalized medicine is the customization of treatment to an individual as opposed to the one treatment-for-all model. Personalized medicine involves categorizing a patient based on his or her physical condition and designing an optimal healthcare solution exclusively for that category. The progression of personalized medicine is dependent on the discovery, validation, and commercialization of biomarkers to stratify populations for treatment and for the development of diagnostics for screening and early detection.

Epigenetic research has come to the forefront of medical research and is implicated in the etiology of a number of physical and mental illnesses including: cancer, obesity, diabetes, schizophrenia, and Alzheimer's disease (Alika et al., 2010; Grant et al. 2010; McGowen et al., 2009; McGowen and Szyf, 2010; Plazas-Mayorca and Vrana, 2011; and Portela and Esteller, 2010). In addition, Epigenetics may hold particular promise in the many scientific and medical areas including but not limited to: cancer, diabetes, drug integrations, drug effectiveness, childhood aggression, suicidal behaviors, aging, inflammation, pain, obesity, schizophrenia, and other mental illnesses (Abdolmaleky et al., 2005; Costa et al., 2003; Iwamoto & Kato, 2009; Kuratomi et al., 2007; McGowan & Kato, 2007; McGowen and Szyf, 2010; Peedicayil, 2007; Petronis et al., 1999; McGowen and Szyf, 2010; Plazas-'Mayorca and Vrana, 2011; and Zawia et al., 2009).

A major challenge in the field includes the identification of an appropriate source material for home-based sample collection that is adequate for large-scale epigenetic research including whole-genome-analysis studies. Epigenetics may be the key for understanding the mechanisms of gene-environment interactions as growing evidence suggests that epigenetic mechanisms may provide a molecular memory of environmental experiences (Ho, 2010; Kappeler and Meaney, 2010; McGowen et al., 2009, McGowen and Szyf, 2010; Portela and Esteller, 2010; Richards, 2008; Russo et al., 2010; Tsai et al, 2010; and Vlaanderen et al., 2010). Preliminary data from some humans suggest that distinct methylation patterns in peripheral blood cells are associated with social behaviors including: childhood aggression, suicidal behaviors, and ageing (Kappeler and Meaney, 2010; McGowen et al., 2009; McGowen and Szyf, 2010; Portela and Esteller, 2010; Russo et al., 2010, Tierling et al., 2010; Tsai et al, 2010; and Zhang et al., 2011).

Due at least in part to the heterogeneous nature of human disease, particularly mental illness, and the complex interaction of contributing etiological factors, studies require large sample sizes to provide reliable and significant effects. However, current research options for sample collection for epigenetic studies do not meet this requirement of "large sample sizes." The need for large sample sizes for studies is also true in order to produce significant effects in regards to studying human-environment interactions as these interactions are also of a very complex nature with many contributing factors. The ability to perform large-scale "population sized" (subject samples numbering in at least the hundreds to thousands) epigenetic research can introduce a new understanding of human-environment interaction and facilitate the completion of longitudinal studies facilitating the development of epigenetic-based screening diagnostics crucial to the progression of modern medicine. This epigenetic research may lead to a new understanding of how the environment affects our epigenome and how this relates to a person's health outcome, which may further lead to the development of preventative interventions for individuals who are considered high-risk and diagnostics for these health disparities including, but not limited to, diagnosis.

Some epigenetic studies attempting to quantify environmental and other complex interactions in human populations use blood as the source material for experimentation. Blood can restrict the researcher's ability to conduct large population-sized studies as it:

1. generally requires medical supervision,
2. involves invasive procedures for collection,
3. carries stigma that limits participation, and
4. is expensive to collect and ship.

Naturally expressed bodily fluids, e.g., saliva and urine, can be an additional or alternative appropriate source material for home-based sample collection as they:

1. do not require invasive techniques,
2. do not have the same stigma as blood,
3. do not require professional supervision, and
4. can be inexpensive to collect.

In addition, at least saliva has been shown to contain white blood cells (Dos-Santos et al., 2009). The use of bodily fluids, e.g., saliva, urine, may enable large-scale "population-sized" epigenetic research. In addition, home-base sample collection of saliva, or urine, may allow for a much wider range of research options available as it can greatly increase participant numbers and samples can be more easily shipped by the subjects from anywhere in the world. For example, the ability to more easily ship samples from anywhere in the world can be particularly useful when samples are from countries that do not have laboratory infrastructure.

An organism's genome is a fixed sequence that contains its hereditary information and is the same in every cell of an organism. An organism's epigenome, by contrast, varies between cell types and changes over the organism's lifetime. Thus, epigenetic studies may include a single cell type as the source of sample material to control for these differences (Johnson and Tricker, 2010; Lister et al., 2009; and Rangwala et al., 2006). For example, human saliva contains numerous cell types, including epithelial cells, cells normally found in the blood (i.e., T-cells and B-cells), bacteria and debris (Dos-Santos et al., 2009 and Viet and Schmidt, 2008). The cells in saliva that are the most important to profile epigenetically are those that come from the blood stream, as these cells carry epigenetic information from the entire body (Kappeler and Meaney, 2010; McGowen and Szyf, 2010; McGowen and Szyf, 2010; Righini et al, 2007; Rosas et al., 2011, Vlaanderen et al., 2010 and Zhang et al., 2011).

Additionally, it may not be practical to use whole saliva DNA as the cells in saliva that are not found in the blood, such as epithelial cells, which make up the vast majority of cells in saliva (Dos-Santos et al., 2009) have the ability to "mask" the epigenetic effects seen in T-cells (cells that originated in the blood) by dampening the effect of the minority of cells (Dos Santos et al., 2009, Lister et al., 2009; and Tierling et al., 2010). To address these concerns AboGen developed a method to separate and extract the different cell types found in bodily fluids such as saliva by taking advantage of cell-specific markers and isolation techniques (e.g., magnetic). This method uses practical amounts of bodily fluids, such as saliva, to yield enriched cells that can be used for downstream biological applications including large-scale functional genomic studies (example epigenomic studies). For example, saliva sample processing technology allows collected samples to be processed into single cell types and have their epigenomes profiled.

Furthermore, saliva (and other bodily fluids) can present challenges with cell isolation as a source material for blood cells in respect to downstream experimentation for reasons such as:

1. Blood is a transporter fluid while saliva is a digestive fluid that can be rich in proteases, enzymes and secreted substances and urine is a excretory fluid consisting of unwanted waste products.
2. Some fluids can have a wide pH range and some of the pH values reported, such as for saliva, would result in death if blood reached that pH (saliva is 6.2-7.4; urine is 4.5-8; blood is 7.35-7.45).
3. Some fluids contain more bacteria than blood.
4. Some fluids contain non-cellular material that varies between individuals and interferes with cell isolation.
5. Some fluids include blood cells, such as T-cells, which can be abundant in blood, but may be rare in other naturally expressed bodily fluids, such as saliva or urine, and are vastly outnumbered by other cell types, such as epithelial cells, unlike in blood.
6. The subset of lymphocyte cells in some bodily fluids, such as saliva, greatly differs from the population of those cell types in blood. For example, only CD4+ CD8− T-cells are reported to be found in saliva.
7. Some fluids are produced each day, such as saliva at about a rate of 0.5-1.5 liters per day per person.

Therefore, there is a need for new methods for isolating rare cells (i.e., T-cells) from saliva and other naturally expressed bodily fluids.

For collecting saliva samples from a large population of people (example: functional genomic studies) who are widely geographically dispersed, several requirements may need to be met for an optimal sample collection device. For example, it may be beneficial to have the sample collection device securely house a toxic preservative solution in a closed chamber. Additionally, the sample collection device may be able to be sent to a donor with the toxic solution safely enclosed. The sample collection device may also allow easy and safe collection of a donor specimen, such as human saliva or urine, with no risk of exposure of the donor to the toxic solution. Furthermore, the sample collection device may allow the donor to safely mix the toxic solution and the specimen (for preservation of the specimen) with no risk of exposure of the donor to neither the toxic solution nor any other hazard. The sample collection device may also allow the donor to send the sample collection device to a laboratory for processing generally "as-is" after securely closing the sample collection device. Finally, the sample collection device may further allow a laboratory technician to receive the sample collection device and safely open it for processing with generally no risk of exposure to any hazards.

Some currently available sample collection devices include, for example, U.S. Pat. No. 7,482,116 which describes a device that utilizes disassociating a barrier to allow fluid communication between a cavity holding the donor sample and a solution, however, embodiments included in the patent are limited to the use of sharp extruding objects and thin pierceable membranes. The thin pierceable membranes can represent a safety hazard to the sample donor as any wrong manipulation (such as with a finger nail) can lead to piercing of the membrane and release of the solution. US patent publication no. 2009/0216213 A1 claims a device that utilizes a pierceable membrane to establish fluid communication between a cavity containing a solution and the donor sample. This can represent a safety hazard to the sample donor as any wrong manipulation can lead to piercing the membrane and exposing the solution. The device also requires exchange of the cap prior to sending the sample to the end user. This can represent a safety hazard as it may expose the sample donor to the potentially toxic solution. Therefore, there is a need for safer and easier to use sample collection devices.

Additionally, the purification process requires cells to maintain their antigen profiles and the epigenomic profiling requires that their epigenome be maintained. To this end, it is necessary to treat the cells in such a way that they are able to generally maintain these features. Currently available treatments generally do not meet this need. For example, U.S. Pat. Nos. 7,267,980 and 7,749,757 disclose solutions containing lysine, glycine and formaldehyde for stabilizing cells from blood. However, those solutions will not protect cells from proteases found in some bodily fluids, such as saliva. Therefore, there is a need for new solutions and methods that will preserve the antigenicity and epigenome of cells in other bodily fluids, such as saliva.

SUMMARY OF THE DISCLOSURE

Embodiments of the disclosure provide safer and easy to use sample collection devices for naturally expressed bodily fluids (for example), as well as solutions and methods for preserving cells of samples collected, and additionally, methods for isolating specific cells either collected and/or preserved. Such isolated cells (and even non-isolated collected cells), can then be analyzed for studies in any of: functional genomic and epigenetic studies, and biomarker discovery (for example).

The sample collection devices according to the present disclosure provide several advantages over currently available sample collection devices. For example, in some embodiments, the sample collection devices use a minimum amount of parts and do not require removal or exchange of a piece or an object thereof. In some embodiments, the sample collection devices do not require any additional manipulation by the sample donor apart from depositing the sample in the sample collection device and closing the sample collection device. In some embodiments, use of the sample collection devices provide improved safety for both the sample donor and the end user, since, for example, sharp objects are not included and there is limited to no risk of exposure to toxic solutions (e.g., sample preservative solutions).

In some embodiments of the sample collection device, the sample collection device can have two main mating bodies, a cap and a tube. The cap can include a closed cavity holding a preservative solution which can mate with the tube to constitute the closed sample collection device. The tube can be configured to receive the donor specimen. The cap and tube are configured so that when the donor deposits the specimen and closes the tube with the cap, the cavity holding the preservative solution may be opened to release the preservative solution and allow it to mix with the donor specimen.

In some embodiments, a bodily fluid sample collection device for the collection of naturally expressed bodily fluids is provided and includes a cap having an outer wall having an engagement member, and an interior chamber for holding a fluid. The chamber may comprise inner walls which define an interior space and an aperture, where the aperture is configured for sealing by a removable blocking member. The blocking member may include a first coupling member for engaging a corresponding second coupling member in a tube, thereby causing removal of the blocking member and opening of the aperture when the cap is coupled to the tube. The device also includes the tube which includes a containment wall defining a reservoir for bodily fluid sample collection, an engagement member complementary to the engagement member of the cap, and the second coupling member.

In some embodiments, one and/or another of the following features may be provided with a sample collection device:
the removable blocking member is a disk-shaped member which threadably engages the aperture;
the first coupling member comprises an indentation disposed centrally in the bottom of the blocking member and the second coupling member is disposed centrally within the tube;
the first coupling member comprises a recess disposed eccentrically in the bottom of the blocking member and the second coupling member is disposed eccentrically within the tube;
the removable blocking member comprises an annular member having threads arranged thereon, where the annular blocking member substantially covers the aperture, and the inner wall of the cap includes complementary threads, such that the annular member can be screwed into the interior space to uncover the aperture;
a locking mechanism, to lock the cap to the tube (or lock any two components together), the locking mechanism may comprise a wedge and a complementary flange;
a sealing mechanism which may comprise a sealing substance associated with the engagement member of the cap, where upon coupling the cap to the tube, the sealing substance flows into at least the engagement member of the cap;
tamper-evident means for determining whether the cap has been opened, which may comprise a ring having a first portion thereof integral with an open end of the cap, where upon the cap being coupled to the tube, the ring is positioned adjacent the tube; as such, in some embodiments, upon the cap being de-coupled from the tube, the first portion is broken and the ring remains substantially adjacent the tube; and/or
the fluid in the cap chamber comprises a solution for preserving cells.

In some embodiments, a bodily fluid sample collection device for the collection of naturally expressed bodily fluid is provided and includes a cap having an interior chamber for holding a fluid and a first engagement member, and a tube comprising a containment wall defining a reservoir for sample collection and a second engagement member for engagement to the first engagement member. In some such embodiments, the cap comprises an outer wall having the first engagement member, the chamber comprises inner walls defining an interior space which holds the fluid, and an aperture, the aperture being configured for sealing by a removable blocking member. In addition, in some embodiments, the blocking member includes a first coupling member for engaging a corresponding second coupling member of the tube, where upon the coupling of the cap to the tube, the blocking member is moved and the aperture opens.

In some embodiments, a method for collecting a sample of a naturally expressed bodily fluid (or toxic or hazardous fluid) is provided and includes providing a bodily fluid collection device according to any of the disclosed sample collection device embodiments, depositing the bodily fluid into the chamber, and mating the cap and tube together such that the corresponding engagement members engage, where the blocking member moves and the preservation fluid flows into the reservoir containing the bodily fluid such that cells contained in the bodily fluid are preserved for analysis. In some such embodiments, further steps may include at least one of (with reference to bodily fluids): isolating one or more cell types for a plurality of cell types in the bodily fluid, and analyzing the collected cells.

As one of skill in the art will appreciate, in some embodiments, at least one of DNA, RNA and proteins can be extracted from collected/preserved cells, whether the isolated cells, or non-isolated cells.

In some embodiments, a kit for the collection of naturally expressed bodily fluids (or toxic and/or hazardous fluids) is provided and comprises a plurality of sample collection devices according to of the disclosed sample collection devices.

In addition, the current disclosure relates to functional genomic studies including epigenetic studies. More particularly, this disclosure also relates to the isolation of cells from bodily fluids, such as saliva and urine, for these studies. Accordingly, some embodiments of the disclosure include methods for preserving the antigenicity and epigenome of cells, and isolating rare cells, including, without limitation T-cells from bodily fluids, such as saliva and urine, are disclosed herein.

As used herein, the collection of "bodily fluids" generally refers to the collection of naturally expressed bodily fluids (although some embodiments can be used for collection of intravenous collection methods—e.g., blood). Thus, with references to the disclosed embodiments, "bodily fluids" refer to naturally expressed bodily fluids including, for example, saliva and urine.

For example, in some embodiments, a solution for preserving cells in bodily fluids, such as saliva and urine, is provided for further separation into cell types and downstream analysis that allows for the cells in saliva to retain their antigenicity and cellular architecture during storage. The solution can contain at least one chemical fixing agent, such as but not limited to paraformaldehyde, and at least one protease inhibitor. In some embodiments, the solution may further contain, for example, one or more of: at least one antimicrobial agent, serum proteins from human and/or other animal species. The solution may be buffered at a pH between about 6.4 to about 8.4, and in some embodiments, between about 7.2 to about 7.6.

In some embodiments, a method for preserving cells in one or more bodily fluids includes contacting collected cells with a solution according to one and/or another embodiment of the present disclosure, which allows the cells to retain their antigenicity and epigenome, for example.

In some embodiments, a method for isolating cells from chemically fixed cells collected from a bodily fluid, e.g., saliva or urine, and includes centrifuging the cells to separate, for example, DNA and/or other soluble material from a pellet of cells, bacteria, and debris, enriching white blood cells from other contents of the pellet, and isolating specific cells (e.g., white blood cells) using antibodies conjugated to magnetic beads targeted to cell specific markers.

In some embodiments, methods for isolating a particular type of cell, for example, a type of white blood cell (e.g., lymphocytes), from one or more bodily fluids (e.g., saliva and/or urine), and includes one or more of the following steps (and, depending upon the embodiment, several or all of the following steps): providing a sample of bodily fluid comprising chemically fixed cells, optionally centrifuging the bodily fluid sample to obtain a pellet comprising cells, optionally re-suspending the pellet in a buffer, subjecting the re-suspended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents may be magnetic beads coupled to antibodies specific to an epitope found on a particular type of white blood cell, and in the separation step may then comprise, for example, magnetically separating the particular type of white blood cell (including lymphocytes) from the mixture of white blood cell types (though other cell separation techniques are within the scope of the disclosure).

In some embodiments, the bodily fluid (e.g., saliva, urine) can be mixed with a chemical fixative solution and the mixture can be removed from the pellet. The pellet can then be re-suspended in a buffer. The re-suspended pellet may optionally be centrifuged and washed one or more times in the buffer. The washed pellet may then be applied to a hydrophilic polysaccharide mixture to form a gradient. This gradient may be different than that used for blood because the density of the cells in other bodily fluids (e.g., saliva, urine) after chemical fixation for preservation can be different due to the different density of the preserved cells requiring an alteration in the time, temperature, and/ or density of the gradient for the cells to be processed through this density gradient.

Additionally, in some embodiments, the white blood cells can form a layer in the gradient. The white blood cell layer can be extracted from the gradient and placed in another centrifuge tube where it may be washed in a buffer and re-pelleted to remove the remaining gradient mixture. The pellet may then be re-suspended and incubated in a buffer containing antibodies that are conjugated to magnetic beads and specific to antigens that are specific for a cell type to be isolated. In some embodiments, the cell type to be isolated is T-cells and the antigen is a T-cell-specific antigen. In some embodiments, the antigen is CD4. The re-suspended cells in the buffer can be bound by the antibody and subjected to a magnetic field that magnetically attracts the cells bound to the antibody-conjugated magnetic beads to the side of the tube. Remaining liquid may then be removed from the tube and the tube is washed in buffer. Isolated T-cells then remain attracted to the side of the tube and are ready for further processing, such as freezing for later downstream experimentation (for example).

In some embodiments, a method for preserving cells in a naturally expressed bodily fluid comprises contacting the bodily fluid with the preservation solution according to any of the disclosed embodiments.

The devices, solutions and methods of sample collection, preservation, isolation and analysis will be better understood in light of the following drawings, detailed description and claims. Like reference symbols in the various drawings indicate like elements.

It is worth noting that while some embodiments of the sample collection devices disclosed herein are set forth for use with the collection of bodily fluids, the same also has particular use with the collection of any other substance, including hazardous and/or toxic fluids.

BRIEF DESCRIPTION OF THE DRAWINGS

FIG. 1 shows a sample collection device comprising a cap and a tube according to some embodiments of the present disclosure.

FIG. 2A shows a longitudinal cross section view of a sample collection device in which the cap contains an inner chamber with a removable blocking member that has an eccentrically located coupling feature which can mate with a coupling member eccentrically located in the tube according to some embodiments of the present disclosure.

FIG. 2B is a cross section view taken along line 2B-2B of FIG. 2A and shows a coupling member eccentrically positioned within the tube according to some embodiments of the present disclosure.

FIG. 6 shows a sample collection device further including a sealed cavity containing a sealing solution that is released into the engagement features of the cap and tube when the cap is coupled to the tube, which prevents the cap from being removed by at least the donor after the cap has been coupled to the tube according to some embodiments of the present disclosure.

FIG. 7A shows a "tamper-evident" cap, in which an annular member at the bottom of the cap can break away from the cap if the cap has been removed after having been rotated/screwed onto the tube according to some embodiments of the present disclosure.

FIG. 7B shows the "tamper-evident" cap shown in FIG. 7A showing the annular member broken away from the cap according to some embodiments of the present disclosure.

FIG. 8 shows the time course of DNA yield in samples stored in chemical fixative solution at room temperature after 0, 1, 2 and 7 days, as well as DNA extracted from T-cells from each sample according to some embodiments of the present disclosure.

DETAILED DESCRIPTION OF THE EMBODIMENTS

Figure 1A:
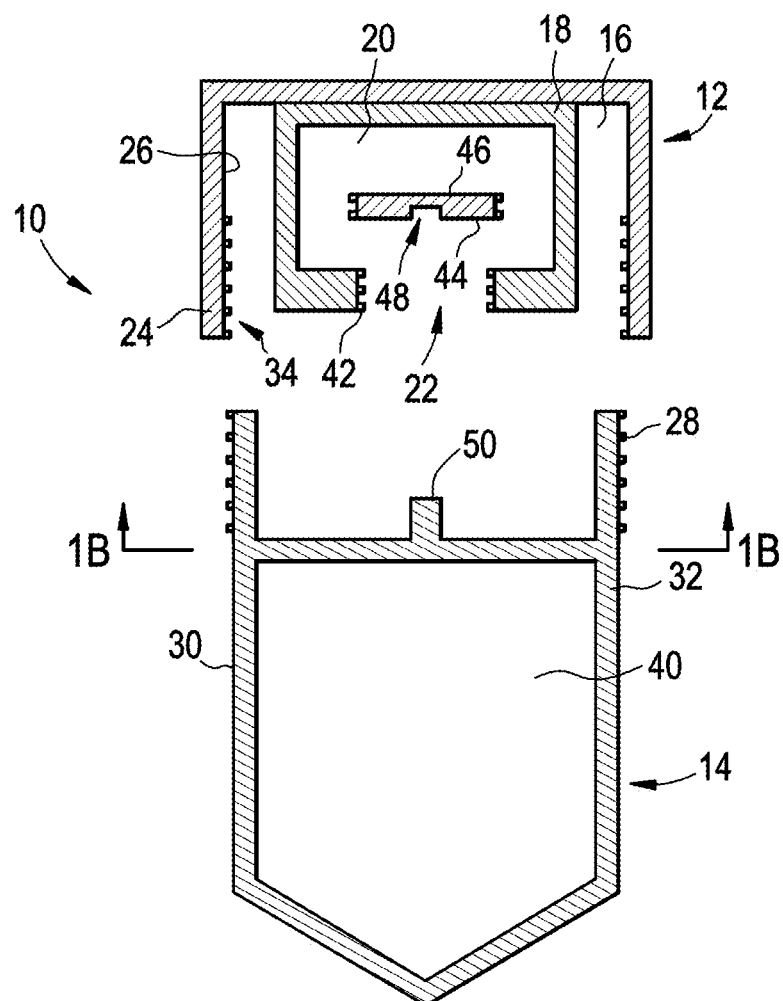
FIG. 1A is a cross section view taken along line 1A-1A of FIG. 1 and shows the interior chamber of the cap comprising inner walls which define an interior space and an aperture according to some embodiments of the present disclosure.

Embodiments of the present disclosure include devices, solutions and methods for the collection of samples, such as bodily fluids, as well as methods for isolating one or more cell types from collected cells (chemically fixed or otherwise). For example, in some embodiments, the sample collection devices provide several advantages over currently available sample collection devices, and in addition, the sample collection devices according to some embodiments use a minimum amount of parts and the devices do not require removal or exchange of a piece or an object. Furthermore, in some embodiments, the sample collection devices may generally not require additional manipulation by the sample donor apart from depositing the sample and closing the collection device. The sample collection devices according to some embodiments include improved safety of use for both sample donors and end users due, at least in part, to the elimination of sharp objects and limited risk of exposure to toxic solutions, as will be described in greater detail below.

In some embodiments, methods for the preservation and isolation of cells from bodily fluids for functional genomic and epigenetic studies, as well as biomarker discovery, are provided. Additionally, this disclosure provides devices, solutions and methods for isolating rare preserved cells, such as T-cells, from bodily fluids (i.e., saliva, urine), as will also be described in greater detail below.

Some embodiments of the sample collection device may include two mating bodies, such as a cap and a tube. In some embodiments, the cap may include a closed cavity, such as an interior space, for holding a preservative solution (which may be toxic) for mating with the tube to constitute a closed sample collection device. The tube may be configured to receive a donor specimen, such as one or more bodily fluids (e.g., saliva, urine). In some embodiments, the cap and/or tube may be configured so that when the donor deposits the specimen and closes the tube with the cap, the cavity in the cap, which may be holding the preservative solution, can be opened to release the preservative solution and allow it to mix with the donor specimen.

One of skill in the art will appreciate that with respect to some embodiments of the collection device described herein, such may be used in combination with accessories that ease specimen deposit within the collection device, including, for example, mouth adapters for saliva collection, funnels and hoses for urine collection, and the like.

In some embodiments, the sample collection device may comprise a cap having an outer wall with interior threads. Additionally, the sample collection device may include an interior chamber for holding a fluid with the chamber comprising walls defining an interior space and a threaded aperture in the wall. The aperture in the wall may be sealed by a threadably removable blocking member, where the blocking member may include engaging members for engaging a coupling member in a tube, thereby causing the blocking member to be removed and the aperture to open when the cap is threaded onto the tube (in some embodiments). In some embodiments, the sample collection device may further include a tube comprising a containment wall defining a lumen or reservoir for sample collection, exterior threads complementary to the interior threads of the outer wall of the cap, and a coupling member that has a shape which is complementary to the engaging member in the cap.

In some embodiments, the threadably removable blocking member can be a disk-shaped member that is at least one of pushed, rotated, screwed, threaded, and/or mated into the aperture of the inner chamber and can be at least one of pushed, rotated, screwed, threaded, and/or mated into the chamber by interaction between the engaging member of the cap and the coupling member of the tube when the cap is rotated or screwed onto the tube. The engaging member can be either centrally or eccentrically located in the disk-shaped member, with the coupling member being at least one of centrally or eccentrically located in the tube, respectively.

The terms push, rotate, screw, mate as well as thread, couple, and attach, as well as any corresponding tenses and plurals thereof (as additionally including the term "feature(s)"), disclosed herein, correspond to structure (well known to those of skill in the art) for connection (either permanent or temporary) of two (or more) components (e.g., "screw means" "mating means", "coupling feature", "engagement feature"). For example, with respect to "pushing", such means can cover a "snap-fit" type of structure; rotation means can cover means in which a protruding member is received by a corresponding recess when one component is rotated relative to another. "Screwed" and "threadably" covers helical threaded engagement and the like. Thus, use of any of these terms (or tenses thereof) can also cover such connection with any such means or the equivalents thereof.

In some embodiments, a threadably movable annular member may not fit into the aperture, but rather covers the aperture from the outside of the inner chamber. In such embodiments, the annular member can have interior threads complementary to threads on the outside of the inner chamber or interior space. Interaction between the coupling features of the annular blocking member and the coupling member of the tube can cause the annular member to be screwed up the outside of the inner chamber, away from the aperture.

In some embodiments, the sample collection device may further include locking or sealing means, such that the cap cannot be removed from the tube by the donor once the cap has been connected or screwed onto the tube, such as by the donor. Suitable locking members can include a wedge on the cap and a matching flange on the tube or visa-versa. The wedge and flange can either be on the inside of the cap and tube, or on the outside of the cap and tube. Suitable sealing means include a sealed cavity containing a sealing solution, such as a glue, wherein the sealing solution is released when the cap is pushed, rotated or screwed onto the tube and thereafter cures in order to prevent disengagement between the cap and tube. In some embodiments, the sealing solution may be a two-component glue, such as an epoxy, with one component being sealed into the cap, and the other component sealed into the tube, such that the two components mix within the threads when the cap is screwed onto the tube. In other embodiments, the sealing solution can be a single component, such as a cyanoacrylate-based glue, which can be in a sealed cavity in the cap or tube, such that the sealing solution is released into the threads when the cap is screwed onto the tube. In some embodiments, the sealing solution can cure soon after engagement between the cap and tube such that disengagement between the tube and cap by the user can be generally prevented.

Alternatively, or in addition, some embodiments may further include an annular member at the base of the cap that is partially secured to the cap, such that removal of the cap after it has been screwed onto the tube breaks the bond between the cap and the annular member, thereby indicating that the tube has been opened. This "tamper-evident" embodiment is similar to those used to attach a cap to a soda bottle.

The sample collection devices according to some embodiments can be made of any suitable plastic, such as polypropylene, polystyrene and polycarbonate. The dimensions of the device can be modified to suit the specific processing the sample will be subjected to. In certain embodiments, typical dimensions include the following. For the inner chamber of the cap, the volume is from about 3 ml to about 10 ml, typically about 6 ml. For the lumen of the tube, the volume is from about 15 ml to about 50 ml, typically about 25 ml. Other volumes are within the scope of some embodiments of the present disclosure.

With respect to the figures, FIG. 1 is an illustration of an embodiment of a sample collection device 10 comprising a cap 12 and a tube 14. The tube can be configured for collection of one or more sample bodily fluids, and the cap can be configured for storing one or more preservation fluids. Additionally, the cap 12 and tube 14 can be configured to securely mate with one another in order to provide a secure containment of at least the sample bodily fluids for storing and shipping. Furthermore, the mechanism by which may be implemented in the sample collection device 10 for securely mating the cap 12 and the tube 14 may prevent disengagement between the cap 12 and the tube 14. One benefit of preventing disengagement between the cap 12 and the tube 14 is that it can prevent at least, for example, contamination of the sample contained in the tube and exposure of any preservation solutions (which may be toxic) to the sample donor, such as those contained in the cap 12.

FIG. 1A shows an example interior chamber 16 of the cap 12 which may be defined by at least one outer wall 24 and at least one inner wall 18 according to some embodiments. The at least one inner wall 18 may further define an interior space 20 and an aperture 22. In addition, the outer wall 24 may include one or more cap engagement features 34 along at least one side of the outer wall 24 for engaging the tube 14. For example, and shown in FIG. 1A, an inside surface 26 of the outer wall 24 can include one or more cap engagement features 34, such as threads, for engaging and mating with one or more complimentary tube engagement features 38, such as threads, associated with the tube 14. The tube 14 may be comprised of at least one containment wall 32 which may define a reservoir 40 for collecting and storing sample body fluids, such as saliva or urine. An outer surface 30 of the containment wall 32 may include the one or more tube engagement features 28, such as threads.

The cap 12 may further include an aperture 22 having one or more aperture engagement features 42, such as threads. In addition, the cap 12 may include a blocking member 46 which may have one or more blocking member engagement features 44, such as threads, for engaging the aperture engagement features 42. For example, the blocking member 46 may be removably coupled to the aperture 22 such that when the blocking member is secured to the aperture, one or more fluids or materials, may be contained within the interior space 20 of the cap. However, upon decoupling of the blocking member 46 to the aperture 22, the one or more fluids or materials may be released from the interior space 20 in the cap 12. For example, once the cap 12 has at least been partially secured to the tube 14, the blocking member 46 may be decoupled from the aperture 22, thereafter allowing fluids or materials in the interior space 20 to be released into the reservoir 40 of the tube 14. The one or more fluids or materials contained in the interior space 20 in the cap 12 may assist in preserving the sample body fluids contained in the reservoir 40 of the tube 14 during at least storage and shipping. Any of the engagement features discussed herein may be any number of engagement features for allowing temporary or permanent engagement between two parts or features of the sample collection device 10 and are not limited to the examples discussed in this disclosure.

The blocking member 46 may also include one or more coupling features 48 which may allow one or more coupling members 50 comprising a part of the tube 14 to engage and couple with the coupling features 48. The coupling between the coupling features 48 and coupling members 50 can assist in decoupling the blocking member 46 from the aperture 22. For example, as the cap 12 is secured to the tube 14, the coupling member 50 may engage and interact with the coupling feature 48 of the blocking member 46, such as similar to the head of a screw driver interacting with the head of a screw. The blocking member 46 may be threadably engaged with threaded aperture engagement features, and the coupling and interaction of the coupling feature 48 and coupling member 50 may cause the threaded engagement between the blocking member 46 and the aperture 22 to be released. The threaded engagement between the blocking member 46 and the aperture 22 may be released, for example, due to rotation of the blocking member 46 relative to the aperture 22. Any number of releasable engagements may be used to engage the blocking member 46 with the aperture 22 such that the engagement between the blocking member 46 and the aperture 22 may be released upon securing the cap to the tube 14. Similarly, any number of features may be integrated in the sample collection device 10 which may allow containment of a solution in a part of the cap 12 or tube 14 such that the solution is not released until the cap is at least partially secured to the tube 14.

Figure 1B:
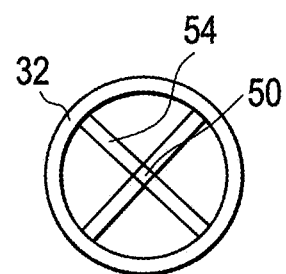
FIG. 1B is a cross section view taken along line 1B-1B of FIG. 1A and shows a coupling member centrally positioned within the tube according to some embodiments of the present disclosure.

The tube 14 in FIG. 1A is shown by way of example as having a coupling member 50 in the shape of a square peg which is complementary to a square shaped indent comprising the coupling feature 48 in the blocking member 46. Furthermore, the coupling member 50 can be centrally located within the tube 14 and the coupling feature may be centrally located on the bottom of the blocking member 46. Therefore, upon threaded engagement between the cap 12 and the tube 14, the square peg coupling member 50 may extend into and engage the square shaped indent coupling feature 48 in the blocking member 46, thus preventing the blocking member 46 from rotating relative to the coupling member 50. However, although the blocking member 46 may be prevented from rotating relative to the coupling member 50, the blocking member 46 may rotate relative to the aperture 22 and become disengaged from the aperture 22, such as from releasing the threaded engagement between the blocking member 46 and aperture 22. FIG. 1B shows an example coupling member 50 secured to an inner surface 52 of the containment wall of the tube 14 by more than one cross-member 54. The one or more cross members 54 can assist in securing the position of the coupling member 50 while allowing space for the passage of fluids or materials into the reservoir 40.

An example method of use of a sample collection device 10 can include the sample collection device 10 supplied with sample preservation fluid in the interior space 20 of the cap 12, and with the blocking member 46 threadably engaged with the aperture 22 in order to contain the sample preservation fluid in the interior space 20. Sample fluid, such as saliva or urine, may then be placed in the reservoir 40 of the tube 14 by a donor. The cap 12 can then be screwed onto the tube 14. Screwing the cap 12 onto the tube 14 may cause the coupling member 50 in the tube 14 to engage the coupling feature 48 of the blocking member 46 and unscrew the blocking member 48 from the aperture 22 and into the interior space 20 of the cap 12. Decoupling the blocking member 48 from the aperture 22 can allow the sample preservation fluid to flow into the reservoir 40 of the tube 40. After release of the sample preservation fluid into the reservoir 40 of the tube 14, the sample preservation fluid can mix with the donor's sample fluid, thereby preserving the donor's sample fluid.

While shown as a square peg in this illustration, the coupling member 50 of the tube 14 can be any shape that is complementary in shape with the coupling feature 48 of the blocking member 46 such that it allows the blocking member 46 to decouple from the aperture 22. The coupling feature 48 can be either in the blocking member 46 or the tube 14, and the complimentary coupling member 50 may be either in the tube 14 or blocking member 46, respectively. Other shapes will be evident to one skilled in the art, including, without limitation, a slot and a tab, like a regular screwdriver and screw, or a cross-shaped pair, like a Phillips screwdriver and screw.

An additional embodiment of the sample collection device 100 is shown by way of example in FIGS. 2A and 2B. The sample collection device 100 may include one or more coupling members 50 and complimentary coupling feature 48 which may be placed eccentrically from either the cap 12 or tube 14. As shown in FIG. 2B, less material and parts may be required for this embodiment to work properly, such as the coupling member 50 maintaining proper positioning by only one cross-member 54. Although the coupling member 50 is shown as being held in position by only one cross-member 54 extending from the containment wall 32 of the tube 14, any number of configurations and cross-members 54 may be used to position the coupling member 50 without departing from the scope of this disclosure.

Figure 3A:
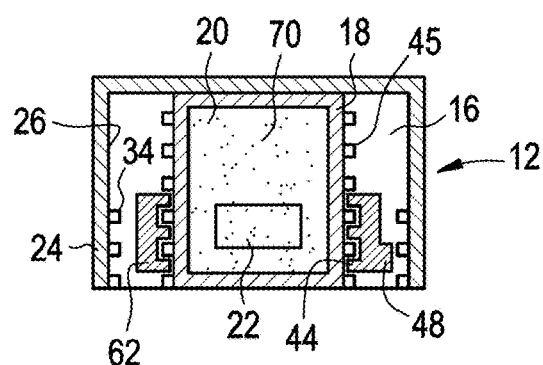
FIG. 3A shows an embodiment of the cap of the sample collection device in which the cap contains an inner chamber with a movable annular member that can cover an aperture in the inner wall according to some embodiments of the present disclosure.
Figure 3B:
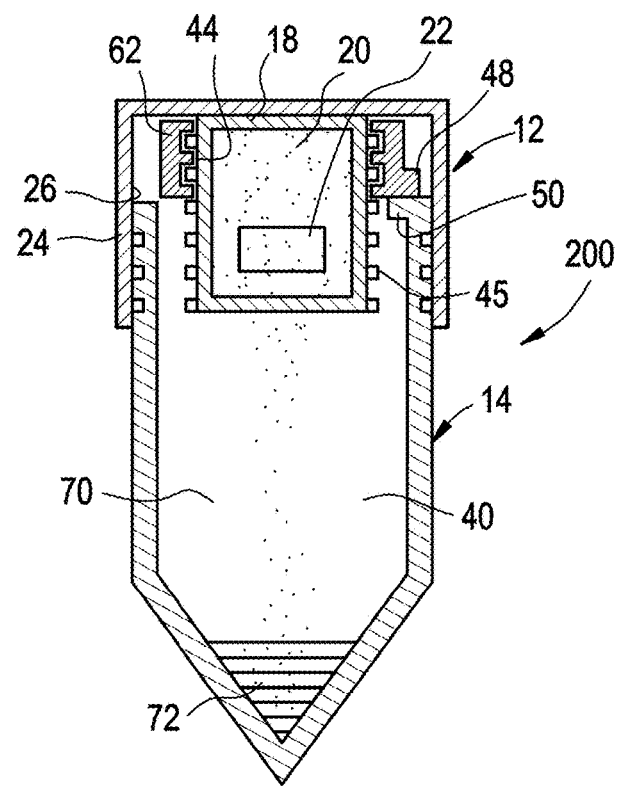
FIG. 3B shows an embodiment of the sample collection device in which the cap is coupled to the tube and the movable annular member is moved to a position where it does not cover an aperture in the inner wall according to some embodiments of the present disclosure.
Figure 3C:
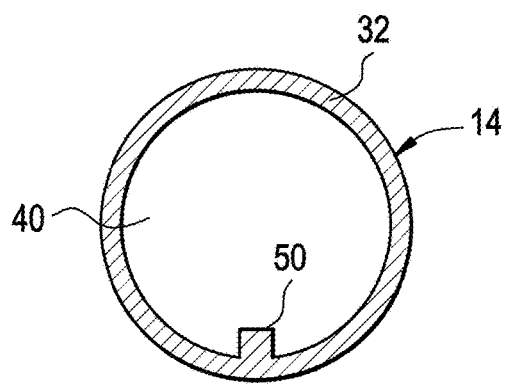
FIG. 3C is a top view of the tube shown in FIG. 2B and shows a coupling member positioned within the tube according to some embodiments of the present disclosure.

Another embodiment of the sample collection device 200 is shown by way of example in FIGS. 3A-3C. More specifically, FIG. 3A shows a cross section of the cap 12 prior to being coupled to the tube 14. The cap 12 can include an outer wall 24 and cap engaging members 34 along an inside surface 26 of the outer wall 24. The interior space 20 may be at least partially defined by at least one of an inner wall 18 or outer wall 24 of the cap 12. Furthermore, the inner wall 18 can include engagement features 60, such as threads, along a surface of the inner wall 18. The inner wall 18 may further define an aperture 22 which may be open or closed depending on the position of an annular blocking member 62 relative to the aperture 22. When the aperture 22 is closed such that the annular blocking member 62 is covering the aperture 22, fluid or material, such as sample preservation fluid or material 70, that me be contained in the interior space 20 may not be allowed to travel outside of the interior space 20, as shown in FIG. 3A. However, when the aperture 22 is open such that the annular blocking member 62 is not covering the aperture 22, the fluid or material 70 that may be contained in the interior space 20 may be allowed to travel outside of the interior space 20, such as into the reservoir 40 of the tube 14, as shown in FIG. 3B. The fluid or material 70 contained in the interior space may be beneficial for preserving sample 72, such as body fluids (i.e., saliva, urine, etc.) placed in the reservoir 40 of the tube 14, similarly as described above. Furthermore, any number of mechanisms may prevent the sample preserving fluid or material 72 from being released from the interior space 20 until the cap 12 is at least partially secured to the tube 14.

In the embodiment shown by way of example in FIGS. 3A-3C, the annular blocking member 62 may be configured to interact with one or more features, such as a coupling member 50, of the tube 14 such that as the cap 12 is being securely coupled to the tube 14, the one or more features of either the tube 14 or annular blocking member 62 can cause the annular blocking member 62 to move from a position where the annular blocking member 62 is covering the aperture 22 to a position where the annular blocking member 62 is not covering the aperture 22, thus allowing the sample preserving fluid or material 72 to release from the interior space 20 and interact with the sample 72.

FIG. 3C shows a cross section of the tube 14, having a containment wall 32 defining a reservoir 40 for sample collection. The tube 14 can include a coupling member 50 for engaging the coupling feature 48 of the annular blocking member 62.

An example method of use of a sample collection device 200 can include the sample collection device 200 supplied with sample preservation fluid 70 in the interior space 20 of the cap 12, and with the annular blocking member 62 covering the aperture 22 in order to prevent the passage of sample preservation fluid 70 through the aperture 22. In this embodiment, sample fluid 72, such as saliva or urine, can be placed in the reservoir 40 of the tube 14. The cap 12 may then be securely coupled, such as threadably engaged, onto the tube 14 causing the coupling features 48 of the annular blocking member 62 to engage the coupling member 50 of the tube 14. The annular blocking member 62 can then threadably engage the engagement features, such as threads, along the side of the inner walls. This can cause the annular blocking member 62 to move away from the aperture 22 so that it no longer covers the aperture 22. This, in turn, can release at least some of the sample preservation fluid 70 into the reservoir 40 of the tube 14, where it can mix with the sample fluid 72, thereby preserving it.

Figure 4A:
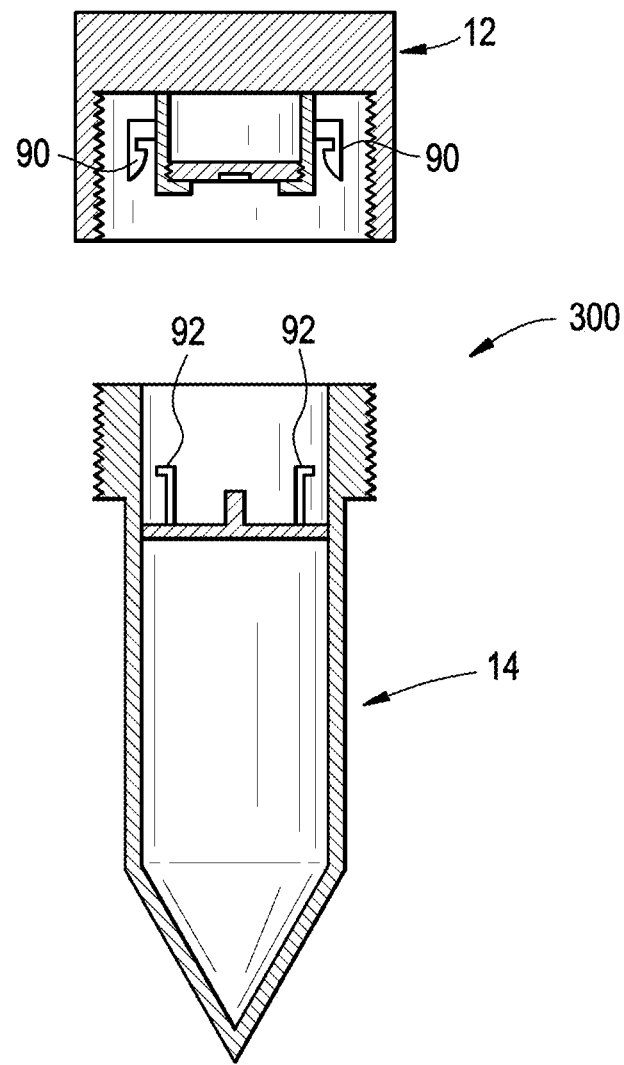
FIG. 4A shows an embodiment of the sample collection device comprising a locking mechanism disposed within the inside of the cap and the tube, which prevents the cap from being removed by at least the donor after the cap has been coupled to the tube according to some embodiments of the present disclosure.
Figure 4B:
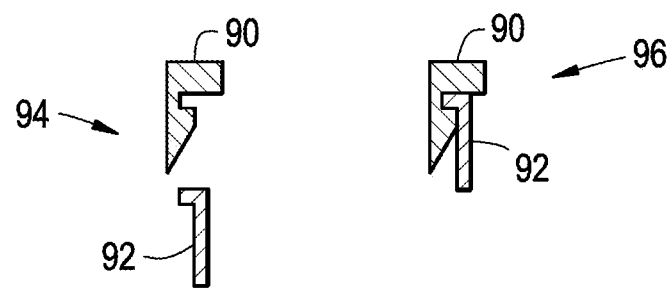
FIG. 4B shows the locking mechanism in the sample collection device shown in FIG. 4A showing a locked configuration and an unlocked configuration according to some embodiments of the present disclosure.

In some embodiments, the sample collection device 300, as shown by way of example in FIGS. 4A and 4B, cap 12 includes at least one coupling feature or a wedge 90 which is shaped and configured to interact with a complimenting coupling feature or a flange 92 of the tube 14. In this embodiment, the wedge 90 and flange 92 are extending along an inside surface of the cap 12 and tube 14. For example, when the cap 12 is coupled to the tube 14, the wedge 90 can engage the flange 92 and form a secure engagement between the cap 12 and the tube 14. Furthermore, once the wedge 90 and flange 92 have been completely engaged with each other, such as the locked configuration 96 shown by way of example in FIG. 4B, the engagement between the wedge 90 and the flange 92 may not be releasable by at least the sample donor. Therefore, once the cap 12 becomes engaged to the tube 14 such that the wedge 90 and flange 92 are securely engaged with each other, the cap 12 may no longer be disengaged from the tube 14 by at least the sample donor. This can prevent at least the sample donor from contaminating the sample body fluid that was deposited in the tube 14, as well as protect the sample donor from contact with the sample preservation solution. FIG. 4B shows sample embodiments of the unlocked configuration 94 and locked configuration 96 between the wedge 90 and flange 92.

Figure 5A:
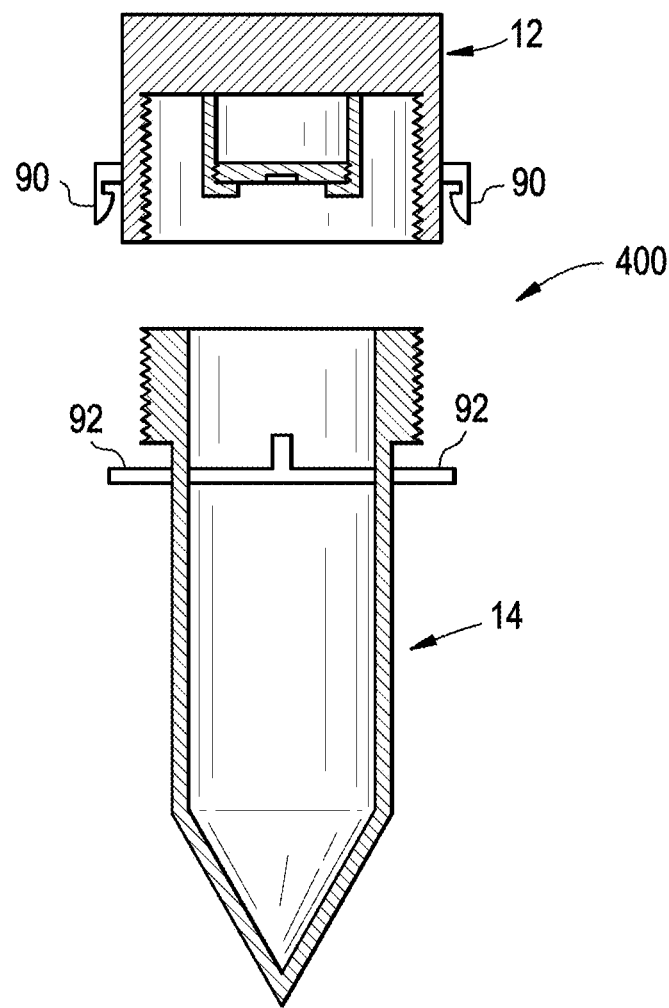
FIG. 5A shows a sample collection device comprising a locking mechanism disposed on an outer surface of the cap and tube, which prevents the cap from being removed by at least the donor after the cap has been coupled to the tube according to some embodiments of the present disclosure.
Figure 5B:
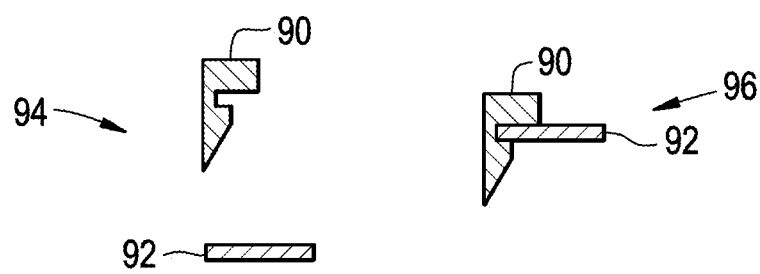
FIG. 5B shows the locking mechanism in the sample collection device shown in FIG. 5A showing a locked configuration and an unlocked configuration according to some embodiments of the present disclosure.

In some embodiments, the sample collection device 400, as shown by way of example in FIGS. 5A and 5B, the wedge 90 and flange 92 are extending along an outside surface of the cap 12 and tube 14, respectively. FIG. 5B shows sample embodiments of the unlocked configuration 94 and locked configuration 96 between the wedge 90 and flange 92.

In some embodiments, the sample collection device 500, as shown by way of example in FIG. 6, where the cap 12 includes one or more sealed cavities 110 containing a sealing substance 112, such as glue. Any one sealed cavity 110 may be either operatively associated or positioned adjacent engagement features 34, such as threads, on the cap 12 such that when the cap 12 is coupled to the tube 14 the one or more sealed cavities 110 may be broken by one or more features or end 150 of the tube 12. Once the sealed cavity 110 is broken, a sealing substance 112, such as glue, may be released from the sealed cavity 110 and cause the cap 12 to become permanently secured to the tube 14.

Any number of features may be included with the cap 12 or tube 14 which may assist in preventing unwanted decoupling of the cap 12 from the tube 14, such as to prevent contamination. Additionally or alternatively, either the cap 12 or tube 14 may include a "tamper evident" feature 160 which may become altered such that it can be known to a user or sample collector if the cap 12 has been unfavorably decoupled from the tube 14. As shown by way of example in FIGS. 7A and 7B, the cap 12 may include a tamper evident feature 160 which may be comprised of a ring that is releasably attached to the open end 162 of the cap 12 such that when the cap 12 is unfavorably decoupled from the tube 14, the tamper evident feature 160 can permanently release its attachment from the cap 12, as shown in FIG. 7B. Once the tamper evident feature 160 is permanently detached from the cap 12, any observer of the cap 12 can determine that the cap 12 had been unfavorably decoupled from the tube 12, thus providing a warning of sample contamination, for example.

Those skilled in the art will recognize that numerous equivalent embodiments can be used to obtain the benefits provided by the sample collection devices disclosed herein. For example, while this specification refers to certain elements being in the cap 12, and others in the tube 14, one skilled in the art would recognize that reversing the elements in the cap 12 to be in the tube 14 and vice-versa, would be an equivalent.

In some embodiments, a solution for preserving cells in one or more bodily fluids, such as saliva and urine, is disclosed. The solution for preserving cells may be beneficial for further separation into cell types and downstream molecular analysis that allows for storage of cells in the body fluid to retain their antigenicity and cellular architecture. The solution may contain at least one chemical fixing agent, such as but not limited to paraformaldehyde, and at least one protease inhibitor. In some embodiments, the solution may further contain one or more of at least one antimicrobial agent, and serum proteins from human and/or other animal species. The solution can be buffered at a pH from between about 6.4 to about 8.4, preferably from between about 7.2 to about 7.6.

For purposes of the disclosure, "preserving cells" means preventing the cells from having their antigens degraded, such that they can be purified or enriched based on their antigens, and preventing alterations in the cellular epigenome. The "epigenome" means the state or pattern of alteration of genomic DNA by covalent modification of the DNA or of proteins bound to the DNA. Examples of such alteration include methylation at the 5 position of cytosine in a CpG dinucleotide, acetylation of lysine residues of histones, and other heritable or non-heritable changes that do not result from changes in the underlying DNA sequence.

In some embodiments, concentrations of agents in the following description can be those of the sample preserving solution itself. Depending upon the bodily fluid, and in the case of saliva, about an equal volume of solution and body fluid can be mixed together. This preferably results in the cells from the body fluids retaining their antigenicity and DNA integrity for at least one week at room temperature.

In some embodiments of the disclosure, the volume of preservation solution held within the device and deployed may be between about 100 and about 500 ml, which is relevant, for example, for the preservation of cells in urine. As such, the preservation solution for urine may be anywhere between about ten times (10×) concentrated solution to a one-point five time (1.5×) solution for urine.

A "chemical fixing agent", according to some embodiments, is a chemical cross-linking compound used to alter cell components such that the cells resist degradation. The chemical fixing agents can also serve to cross-link histones and other DNA-binding proteins to the DNA. Such agents may be known in the art and include, without limitation, paraformaldehyde, formaldehyde, formalin, aldehydes, alcohol, oxidizing agents, Mercurials, Picrates, Hepes-glutamic acid buffer-mediated organic solvent protection effect (HOPE), fixative combinations such as Zambonis fixative, combinations of aldehydes, and synthetic cross-linking reagents. In some embodiments, the chemical fixing agent is paraformaldehyde. In some embodiments, the chemical fixing agent is present at a concentration of about 1% (v/v).

To protect the cells from degradation by proteases present in the body fluids, in some embodiments, the solution can contain at least one protease inhibitor. In some embodiments, the protease inhibitor can be selected from the group consisting of Aspartic protease inhibitors, Cysteine protease inhibitors, Metalloprotease inhibitors, Serine protease inhibitors (e.g., serpins), Threonine protease inhibitors, Trypsin inhibitors, and Kunitz STI protease inhibitor. Some specific, non-limiting, examples include sodium azide, PMSF, Aprotinin, leupeptin, pepstatin, natural or synthetic proteinase inhibitors, and cocktail mixtures of protease inhibitors. Suitable concentrations of these inhibitors can include, without limitation, PMSF (Phenylmethylsulfonyl fluoride) Serine proteases at about 0.1-1 mM, Benzamidine Serine proteases at about 1 mM, Pepstatin A Acid proteases at about 1 μg/ml, Leupeptin Thiol proteases at about 1 μg/ml, Aprotinin Serine proteases at about 5 μg/ml, and Antipain Thiol proteases at about 1 m/ml. In certain embodiments, the protease inhibitor is sodium azide at a concentration of about 0.01% (w/v).

To prevent damage to the cells from microbial contamination, some embodiments of the solution contain at least one antimicrobial agent. Suitable antimicrobial agents include, without limitation, antibacterial and antifungal antibiotics.

Preservation of cell architecture is enhanced by the presence of serum proteins, which may optionally be added to the solution in some embodiments. Additionally serum proteins may be used to neutralize osmotic difference between cells and solution. These can be from human or other animal sources. In some cases, whole serum may be used. For example, fetal bovine serum may be added, in some embodiments at about 1% (v/v).

The solution according to the disclosure may include any combination of the foregoing embodiments.

In some embodiments of the disclosure, a method for preserving cells in one or more bodily fluids is disclosed. The method for preserving the cells can comprise contacting the body fluids with the solution according to the present disclosure. The body fluids can contain a variety of cell types and the cells in the body fluids can be preserved by the solution according to the present disclosure. While not critical to the present disclosure, a ratio of solution to body fluids of from about 1 to 1 is typically used.

The following examples are intended to further illustrate some embodiments of the solutions and methods for preserving cells in body fluids and are not to be construed to limit the scope of this disclosure.

For example, a solution of PBS pH 7.4, 1% Paraformaldehyde, 1% FBS, and 0.01% NaN3 can be added at a 1:1 ration with saliva, then T-cells can be purified and DNA extracted. The results of such a process are shown in FIG. 8. These results can demonstrate that the integrity of the antigenicity and DNA of T-cells was maintained for at least one week.

In some embodiments of the present disclosure, a method is disclosed which provides a sample of one or more body fluids, such as saliva or urine, comprising chemically fixed cells, and optionally centrifuging the body fluid sample to separate DNA and other soluble material from a pellet of cells including bacteria and debris. The method can further include enriching white blood cells, including lymphocyte cells, from other contents of the pellet. Additionally, specific cells may be isolated using antibodies conjugated to magnetic beads targeted to cell specific markers.

In some embodiments, the disclosure provides a method for isolating a particular type of white blood cell, specifically including, but not limited to lymphocytes, from bodily fluids (i.e., saliva, urine, etc.), comprising, for example one or more (and in some embodiments, several or all of the steps): providing a body fluid sample comprising chemically fixed cells, optionally centrifuging the body fluid sample to obtain a pellet comprising cells, optionally resuspending the pellet in buffer, subjecting the re-supended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents can include magnetic beads coupled to antibodies specific to an epitope found on a particular type of white blood cell, and separating may comprise magnetically separating the particular type of white blood cell (including lymphocytes) from the mixture of white blood cell types, though any method (and corresponding system/device) for separating cell types from one another is within the scope of this disclosure. Magnetic separation is but one method for doing so.

The cells can be chemically fixed prior to being subjected to the method according to this disclosure. The cells can be chemically fixed by, e.g., contacting a sample of saliva with a chemical fixation solution. This is done to preserve the cells over time at ambient temperatures. This can also allow for a complete study of the epigenome as it allows histone modifications and other protein-DNA interactions to be studied from the deposited body fluid samples. Histones must be chemically fixed to the DNA in order to be studied. Without fixation, the histones generally cannot remain bound to the DNA and the proteins can degrade over time.

In some embodiments, the buffer can comprise sodium azide, the buffer can comprise phosphate buffered saline and sodium azide, In some embodiments, the buffer may further comprise fetal bovine serum. In some embodiments, the buffer is at a pH from between about 7.2 to about 7.6.

In some embodiments, the cells are washed once in buffer. This in practice removes soluble material and in the case of saliva it removes what has been classified as the "buccal" layer (Dos-Santos et al., 2009).

In some embodiments, the mixture of white blood cells is washed one or more times in buffer prior to separating. This is preferably done to remove any remaining density gradient solution from the mixture of cell types.

In the process, the antibodies may bind to the particular type of white blood cells, thus binding the particular type of white blood cells to the magnetic beads. The particular type of white blood cells can then be separated from any other cell types by placing the magnetic beads in a magnetic field and removing any remaining liquid to obtain isolated cells of the particular type of white blood cells.

In some embodiments, the particular type of white blood cells can be a lymphocyte, where the lymphocyte may be a T-cell. In such embodiments, the antibodies used may be specific to an antigen specific to T-cells (e.g., the antigen being CD4). In some embodiments, the isolated blood cells may then be frozen prior to further processing, such as prior to epigenetic analysis.

The following example is intended to further illustrate an example method embodiment of the present disclosure and is not intended to limit the scope of the disclosure.

Example: Isolating T-cells from a bodily fluid (e.g., saliva)

Saliva is collected, and the saliva is mixed with preservation solution. The cells are then pelleted by centrifugation and the processing solution is removed. The cells are then re-suspended in about 6 ml buffer (PBS, pH 7.4), 1% FBS, 0.01% NaN3), then washed once in a buffer and repelletted. The pellet are resuspended in about 6 mL PBS-15 FBS- 0.01%NaN3 and subjected to density gradient centrifugation using 1.082-1.072 g/ml of Ficoll® (GE Healthcare). The white-blood cells are spun to the interface of the polysaccharides and buffer while the bacteria, debris, and any other particulate matter were pelleted at the bottom of the tube. The cells are extracted from the tube and placed in a new tube. The cells are then washed in Hank's Balanced Salt Solution once and then washed with the PBS-NaN3-FBS buffer once to remove remaining density gradient solution that may have been taken while extracting the white blood cells from the interface.

Figure 9:
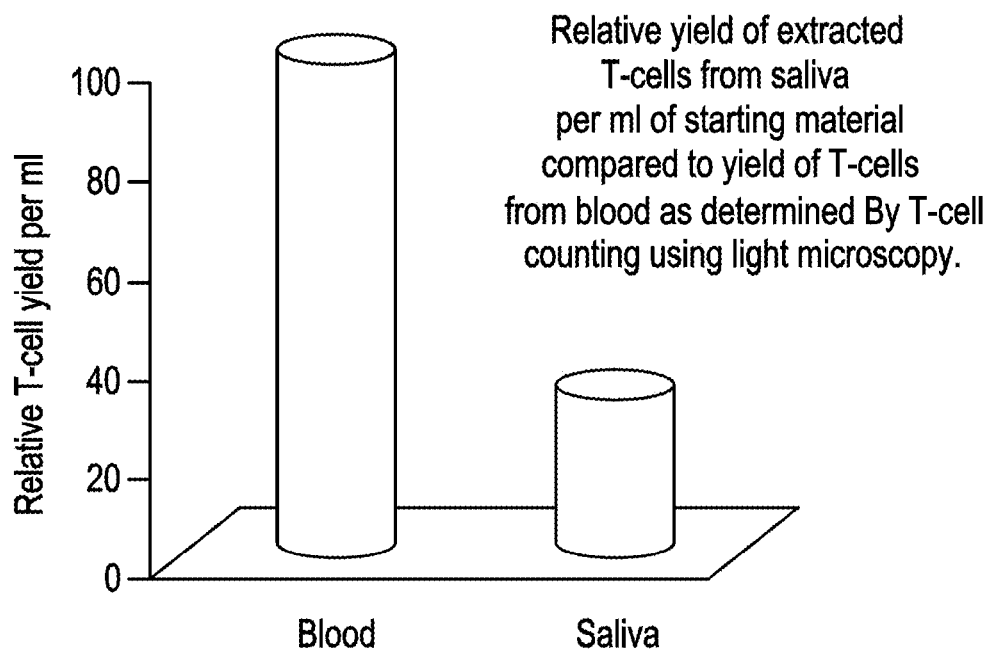
FIG. 9 is a chart illustrating the relative yield of extracted T-cells per ml of starting material (e.g., sample of bodily fluid), as compared to a yield of T-cells from blood.
Figure 10:
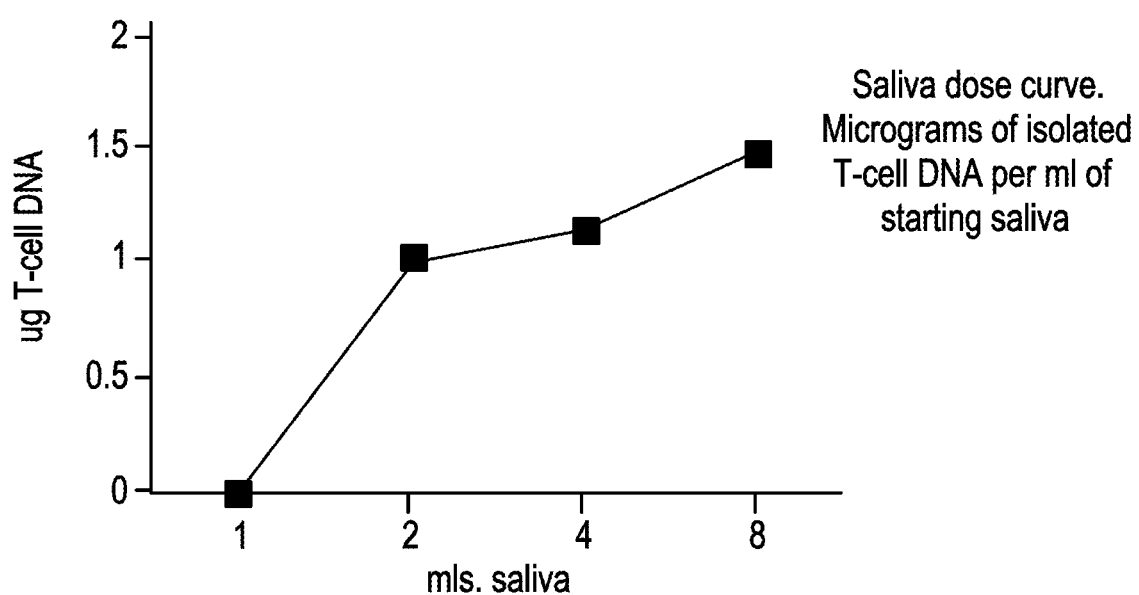
FIG. 10 shows a saliva dose curve of micrograms of isolated T-cell DNA per ml of saliva according to some embodiments of the present disclosure.

The sample now includes highly enriched white-blood cells with minimal bacteria and minimal debris. This step can also greatly decrease other cell types, such as epithelial cells. The cells can then be incubated in buffer (PBS-NaN3-FBS) with antibody targeted against CD4 conjugated to magnetic beads (Dynabeads® Invitrogen®). The samples can then be placed in a magnetic field, the beads brought to the side of the tube, and the liquid removed. The liquid may contain everything not bound to the beads through the antibody. The T-cells can be bound to the antibody and not removed due to the magnetic field. The beads and the attached cells can be washed in buffer to eliminate any non-specific or weak binding of other cells, bacteria, or other debris found in bodily fluids, such as saliva or urine. The cells can then be frozen for later downstream processing and analysis. The isolation of T-cells can be confirmed by light microscopy (T-cells are very distinct compared to epithelial cells and bacteria) (see FIG. 9). Additionally, flow cytometry and F.A.C.S. analysis using antibodies against CD3, CD4, and CD8 can confirm visual assessment of the isolated cells. The T-cells may then be tittered from the body fluid to determine the number of T-cells per unit of body fluid (ml) in order to determine the amount of body fluid, such as saliva or urine, for an adequate number of cells for downstream experimentation (see FIGS. 9 and 10). The isolated cells can be shown to have DNA devoid of degradation and appropriate for downstream use (see FIG. 8).

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, any logic flow depicted in the accompanying figures and described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to collection, preservation, separating and isolating of cells from bodily fluids (e.g., saliva, urine), as well as the collection of other substances, including toxic and/or hazardous substances/fluids (as well as the preservation, separating and isolation of components thereof). In other words, elements from one or another disclosed embodiments may be interchangeable with elements from other disclosed embodiments.

REFERENCES (HEREIN INCORPORATED BY REFERENCE)

Abdolmaleky, H. M., Thiagalingam, S., Wilcox, M. (2005). Genetics and epigenetics in major psychiatric disorders: dilemmas, achievements, applications, and future scope. American Journal of Pharmacogenomics. 5(3): 149-60.

Alika K. Maunakea, Muni Chepelev, Keji Zhao. 2010. Epigenome Mapping in Normal and Disease States. Circ. Res. 107; 327-339

BCC Research. Cell-based assays: Technolgies and global markets. 2011. market report BCC Research. Epigenomics. 2010. market report BCC Research. Life science tolls and reagents. 2011. market report BCC Research, Sample preperation in genomics, proteiomics, and epigenomic: global markets. 2011. market report Becker, M. A., & Dos-Santos, M. C. (2010). Psychological stress and its influence on salivary flow rate, total protein concentration and IgA, IgG and IgM titers. Neuroimmunomodulation. 17(6):396-404.

Bertho, A. L. 2009. Cell Phenotyping in saliva of individuals under phycological stress. Cellular immunology. 260:39-43.

Burdge, G. C., & Lillycrop, K. A. (2010). Nutrition, Epigenetics, and Developmental Plasticity: Implications for Understanding Human Disease. Annu. Rev. Nutr. 30:315-39.

Chouliarasa, L., Ruttena, B. P., Kenisa, F., Peerboomsa, O., Vissera, P. J., Verheya, F., van Osa, J., Steinbuscha, H. W., & van den Hovea, D. L. (2010). Epigenetic regulation in the pathophysiology of Alzheimer's disease. Progress in Neurobiology. 90(4): 498-510.

Costa, E., Grayson, R. D., & Guidotti, A. (2003). Epigenetic downregulation of GABAergic function in schizophrenia: Potential for pharmacological intervention. Molecular Interventions. 3(4): 220-229.

Dos-Santos M C, Matos-Gomes N, Makimoto F H, Katsurayama M, Santana L L, Becker M A, Paredes-Garcia E, Bertho A L. (2009). Cell Phenotyping in saliva of individuals under phycological stress. Cellular immunology. 260:39-43

Eaves, L., Silberg, J., Erkanli, A. (2003). Resolving multiple epigenetic pathways to adolescent depression. Journal of Child Psychology and Psychiatry. 44(7): 1006-1014.

Ho, S. (2010). Environmental epigenetics of asthma: An update. The Journal of Allergy and Clinical Immunology. 126(3):453-465.

Iwamoto, K., & Kato, T. (2009). Epigenetic Profiling in Schizophrenia and Major Mental Disorders. Neuropsychobiology. 60(1): 5-11.

Johnson L J and Tricker P J. (2010) Epigenomic Plasticity Within Populations: its evolutionary significance and potential. Heredity. 105: 113-121

Kalorama Information. Personalized medice diagnostocs. 2011. market report

Kappeler, L., & Meaney, M. J. (2010). Epigenetics and parental effects. Bioessays. 32: 818-827.

Kuratomi G, Iwamoto K, Bundo M, Kusumi I, Kato N, Iwata N, Ozaki N, Kato T. (2007). Aberrant DNA methylation associated with bipolar disorder identified from discordant monozygotic twins. Mol. Psychiatry. 13(4): 429-441.

Lal R., Edison L., and Chused T., (1987). Fixation and long-term storage of human lymphocytes for surface marker analysis by flow cytometry. Cytometry 9:213-219

Lister, L., Pellizzola, M., Dowen, R. H, Hawkins, R. D., Hon, G., Tonti-Filipinni, N., et al. (2009). Human DNA methylome at base resolution show widespread epigenetic differences. Nature. 462: 315-322.

Matos-Gomes, N., Katsurayama, M., Makimoto, F. H., Santana, L. L., Paredes-Garcia, E., Mastroeni, D., Grover, A., Delvaux, E., Whiteside, C., Coleman, P. D., & Rogers, J. (2010). Epigenetic changes in Alzheimer's disease: Decrements in DNA methylation. Neurobiology of Aging. 31(12): 2025-2037.

McGowan, P. O. & Kato, T. (2007). Epigenetics in mood disorders. Environmental Health and Preventive Medicine. 13(1): 16-24.

McGowen, P. O., Sasaki, A., D'Alessio, A. C., Dymov, S., Labonte, B., Szyf, M., Turecki, G., Meaney, M. (2009). Epigenetic regulation of the glucocorticoid receptor in human brain associated with childhood abuse. Nature Neuroscience. 12(3):342-8.

McGowan, P. O., Szyf, M. (2010). The epigenetics of social adversity in early life: Implications for mental health outcomes. Neurobiology of Disease. 39: 66-72.

Mill, J., Petronis, A. (2007). Molecular studies of major depressive disorder: the epigenetic perspective. Molecular psychiatry. 12: 799-814.

Peedicayil, J. (2007). The role of epigenetics in mental disorders. Indian J Med Res. 126: 105-111.

Petronis, A., Paterson, A. D., & Kennedy, J. (1999). Schizophrenia: An epigenetic puzzle? Schizophr Bull. 25(4): 639-655

Plazas-Mayorca M, Vrana K. (2011). Proteomic investigation of epigenetic in neuropsychiatric disorders: A missing link between genetics and behavior? J Proteome Research. 10: 58-65

Portela A, and Esteller, M. 2010. Epigenetic modifications and human disease. Nature Biotechnology. 28:10, 1057

Righini C A, Fraipont F, Timsit J F, Faure C, Brambilla E, Reyt, Favrot M C. (2007). Tumor-specific methylation in saliva: A promising biomarker for early detection of head and neck cancer recurrence. Clin. Cancer Res. 13(4): 1179-85

Rosas S L B, Koch w, Carvalho M G C, Wu L, Califano J, Westra W, Jen J, and Sidransky D. (2001). Promoter hypermethylation patterns of p16, O-methylguanine-DNA-methyltransferase, and death associated protein kinase in tumors of and saliva of head and neck cancer patients. Cancer Research. 61:939-42

Russo P, Lauria F, Siani A. (2010) Heritability of body weight: Moving beyond genetics. Nutrition, Metabolism and Cardiovascular Diseases. 20: 691-697

Teirling S, Souren N Y, Reither S, Zang K D, Meng-Henschel J, Leitner D, Oehl-Jaschkowits B, Walter J. (2010). Dna methylation studies on imprinted loci in male monozygotic twin pairs discordant for Beckwith-Wiedmann syndrome. Clinical Genetics. 79: 1399-004

Tsai S J, Hong C J, Liou Y J. (2010). Recent molecular genetic studies and methodological issues in suicide research Progress in neuro-psychopharmacology and biology psychiatry Viet C T, and Schmidt B L. (2008). Methylation Array Analysis of Preoperative and Postoperative Saliva DNA in Oral Cancer Patients. Cancer Epidemiol Biomarkers Pre. 17(12): 3603-11

Zhang F F, Cardarelli, Carroll J, Zhang S, Fulda K, Gonzales K, Vishvvanatha J. Morabia A, Santella R (2011). Physical activity and global methylation in a cancer-free population. Epigenetics. 6(3) 293-299

Vlaanderen, J, Moore, L. E., Smith, M. T., Lan, Q., Zhang, L , Skibola, C. F., Rothman, N., & Vermeulen, R (2010). Application of OMICS technologies in occupational and environmental health research, current status and projections. Occup Environ Med. 67:136-143.

What is claimed is:

1. A method for collecting and preserving a biological sample, the method comprising:
receiving a biological sample in a sample collection vessel;
threading a cap onto the sample collection vessel;
coupling an annular valve in the cap with the sample collection vessel, wherein coupling causes a first cylinder of the annular valve and a second cylinder of the annular valve to move relatively and thereby open a vent in the annular valve;
releasing a reagent from a reagent chamber in the cap, through the vent, and into a sample collection reservoir in the sample collection vessel to mix with and preserve the biological sample; and
sealing an aperture of the sample collection vessel with the cap;
wherein threading the cap onto the sample collection vessel causes coupling of the annular valve with the sample collection vessel and causes releasing of the reagent from the reagent chamber in the cap through the vent in the annular valve and into the sample collection reservoir in the sample collection vessel.

2. The method of claim 1, wherein receiving a biological sample at the sample collection vessel comprises receiving a biological sample through a funnel attached to the sample collection vessel and wherein the method further comprises detaching the funnel from the sample collection vessel.

3. The method of claim 1, wherein releasing the reagent from the reagent chamber through the vent comprises releasing the reagent through a plurality of vents.

4. The method of claim 1, wherein relatively moving the first cylinder and second cylinder comprises moving the annular valve from a closed configuration to an open configuration, and wherein the annular valve retains the reagent in the reagent chamber in the closed configuration.

5. The method of claim 1, wherein relatively moving the first cylinder and second cylinder comprises at least partially opening the vent in the annular valve.

6. The method of claim 1, wherein relatively moving the first cylinder and second cylinder comprises fully opening the vent in the annular valve.

7. The method of claim 1, wherein relatively moving the first cylinder and second cylinder comprises moving the second cylinder translationally along a longitudinal axis of the cap and through an aperture of the first cylinder.

8. The method of claim 1, wherein the vent is positioned on a sidewall of the second cylinder, and wherein relatively moving the first cylinder and second cylinder comprises moving a sidewall of the first cylinder at least partially past the vent.

9. The method of claim 1, wherein coupling the annular valve to the sample collection vessel comprises coupling a flange on the annular valve to a wall of the sample collection vessel.

10. The method of claim 1, wherein the first and second cylinders comprise generally constant exterior diameters.

11. The method of claim 10, wherein coupling the annular valve to the sample collection vessel comprises coupling a flange on the annular valve to a wall of the sample collection vessel.

12. The method of claim 1, wherein threading the cap onto the sample collection vessel comprises threadedly engaging a connection member disposed on an exterior surface of the sample collection vessel with a complementary connection member disposed on an interior surface of the cap.

13. The method of claim 1, wherein the annular valve is press fit in the cap to create a fluid-tight seal.

14. The method of claim 1, further comprising at least partially disassociating the cap from the sample collection vessel to cause the movable annular valve to obstruct the vent.

15. The method of claim 1, wherein the annular valve comprises a sliding connection between the first and second cylinders.

16. The method of claim 1, wherein the first cylinder of the annular valve moves relatively to the second cylinder by a sliding movement.

17. The method of claim 1, further comprising providing the sample collection vessel, the cap, and the annular valve as a separable two-piece sample collection system, the sample collection vessel comprising a first piece of the separable two-piece sample collection system, and the cap with movable annular valve comprising a second piece of the separable two-piece sample collection system.

18. The method of claim 1, wherein a diameter of an inner wall of the first cylinder is sufficiently equal to a diameter of an outer wall of the second cylinder to create a fluid-tight connection therebetween and allow relative movement.

19. The method of claim 1, wherein
threading the cap onto the sample collection vessel causes coupling of the annular valve with the sample collection vessel, wherein
the vent is positioned on a sidewall of the second cylinder, wherein
relatively moving the first cylinder and second cylinder comprises moving a sidewall of the first cylinder at least partially past the vent, and wherein
relatively moving the first cylinder and second cylinder comprises moving the second cylinder translationally along a longitudinal axis of the cap and through an aperture of the first cylinder.

\* \* \* \* \*